(12) United States Patent
Schenk

(10) Patent No.: US 6,890,535 B1
(45) Date of Patent: May 10, 2005

(54) PHARMACEUTICAL COMPOSITIONS AND METHODS FOR TREATMENT OF AMYLOID DISEASES

(75) Inventor: Dale B. Schenk, Burlingame, CA (US)

(73) Assignee: Neuralab Limited (BM)

( * ) Notice: Subject to any disclaimer, the term of this patent is extended or adjusted under 35 U.S.C. 154(b) by 11 days.

(21) Appl. No.: 09/724,567

(22) Filed: Nov. 28, 2000

Related U.S. Application Data

(63) Continuation of application No. 09/585,817, filed on Jun. 1, 2000, and a continuation-in-part of application No. 09/580,015, filed on May 26, 2000, which is a continuation-in-part of application No. 09/322,289, filed on May 28, 1999, which is a continuation-in-part of application No. 09/201,430, filed on Nov. 30, 1998.

(60) Provisional application No. 60/137,010, filed on Jun. 1, 1999, provisional application No. 60/080,970, filed on Apr. 7, 1998, and provisional application No. 60/067,740, filed on Dec. 2, 1997.

(51) Int. Cl.[7] .................. A61K 39/38; A61K 39/21; A61K 38/00

(52) U.S. Cl. .................. 424/184.1; 424/188.1; 514/2

(58) Field of Search .................. 424/184.1, 185.1; 514/2, 12, 14, 17; 530/300, 360

(56) References Cited

U.S. PATENT DOCUMENTS

| | | |
|---|---|---|
| 4,666,829 A | 5/1987 | Glenner et al. |
| 5,004,697 A | 4/1991 | Pardridge |
| 5,057,540 A | 10/1991 | Kensil et al. |
| 5,187,153 A | 2/1993 | Cordell et al. |
| 5,192,753 A | 3/1993 | McGeer et al. |
| 5,208,036 A | 5/1993 | Eppstein et al. |
| 5,220,013 A | 6/1993 | Ponte et al. |
| 5,231,000 A | 7/1993 | Majocha et al. |
| 5,231,170 A | 7/1993 | Averback |
| 5,270,165 A | 12/1993 | Van Nostrand et al. |
| 5,387,742 A | 2/1995 | Cordell |
| 5,434,170 A | 7/1995 | Andrulis, Jr. |
| 5,441,870 A | 8/1995 | Seubert et al. |
| 5,571,499 A | 11/1996 | Hafler et al. |
| 5,571,500 A | 11/1996 | Hafler et al. |
| 5,583,112 A | 12/1996 | Kensil et al. |
| 5,585,100 A | 12/1996 | Mond et al. |
| 5,593,846 A | 1/1997 | Schenk et al. |
| 5,605,811 A | 2/1997 | Seubert et al. |
| 5,612,486 A | 3/1997 | McConlogue et al. |
| 5,622,701 A | 4/1997 | Berg |
| 5,641,473 A | 6/1997 | Hafler et al. |
| 5,641,474 A | 6/1997 | Hafler et al. |
| 5,645,820 A | 7/1997 | Hafler et al. |
| 5,679,348 A | 10/1997 | Nesburn et al. |
| 5,688,651 A | 11/1997 | Solomon |
| 5,733,547 A | 3/1998 | Weiner et al. |
| 5,736,142 A | 4/1998 | Sette et al. |
| 5,744,368 A | 4/1998 | Goldgaber et al. |
| 5,750,349 A | 5/1998 | Suzuki et al. |

(Continued)

FOREIGN PATENT DOCUMENTS

| | | |
|---|---|---|
| EP | 451 700 A1 | 10/1991 |
| EP | 276 723 B1 | 12/1993 |
| EP | 613 007 A2 | 8/1994 |
| EP | 666 080 A1 | 8/1995 |
| EP | 359 783 B1 | 11/1995 |
| EP | 683 234 A1 | 11/1995 |
| EP | 440 619 B1 | 1/1996 |
| EP | 526 511 B1 | 5/1997 |
| EP | 762 859 A1 | 7/1997 |
| EP | 783 104 A1 | 7/1997 |
| EP | 594 607 B1 | 8/1997 |
| EP | 845 270 A1 | 6/1998 |
| EP | 863 211 A1 | 9/1998 |
| EP | 868 918 A2 | 10/1998 |
| EP | 652 962 B1 | 12/1998 |
| EP | 911 036 A2 | 4/1999 |
| EP | 561 087 B1 | 8/1999 |
| EP | 639 081 B1 | 11/1999 |
| EP | 506 785 B1 | 3/2000 |
| EP | 1 172 378 A1 | 1/2002 |

(Continued)

OTHER PUBLICATIONS

Andersen et al., "Do nonsteroidal anti–inflammatory drugs decrease the risk for Alzheimer's disease?," *Neurology*, 45:1441–1445 (1995).

Associated Press, "Immune cells may promote Alzheimer's, a study finds," *The Boston Globe* (Apr. 13, 1995).

Bard et al., "Peripherally administered antibodies against amyloid β–peptide enter the central nervous system and reduce pathology in a mouse model of Alzheimer disease," *Nature Medicine*, 6(8):916–919 (2000).

Barrow, et al., "Solution Conformations and aggregational Properties of Synthetic Amyloid Beta–Peptides of Alzheimer's Disease. Analysis of Circular Dichroism Spectra", *J. Mol. Biol.*, 225(4): 1075–1093 (1992).

Bauer et al., "Interleukin–6 and α–2–macroglobulin indicate an acute–phase state in Alzheimer's disease cortices," *FEBS Letters*, 285(1):111–114 (1991).

(Continued)

*Primary Examiner*—Gary Kunz
*Assistant Examiner*—Christopher James Nichols
(74) *Attorney, Agent, or Firm*—Townsend and Townsend and Crew LLP

(57) ABSTRACT

Disclosed are pharmaceutical compositions and methods for preventing or treating a number of amyloid diseases, including Alzheimer's disesase, prion diseases, familial amyloid neuropathies and the like. The pharmaceutical compositions include immunologically reactive amounts of amyloid fibril components, particularly fibril-forming peptides or proteins. Also disclosed are therapeutic compositions and methods which use immune reagents that react with such fibril components.

57 Claims, 16 Drawing Sheets

U.S. PATENT DOCUMENTS

| | | | |
|---|---|---|---|
| 5,753,624 A | 5/1998 | McMichael et al. | |
| 5,776,468 A | 7/1998 | Hauser et al. | |
| 5,780,587 A * | 7/1998 | Potter | 530/326 |
| 5,786,180 A | 7/1998 | Konig et al. | |
| 5,824,322 A | 10/1998 | Balasubramanian | |
| 5,837,473 A | 11/1998 | Maggio et al. | |
| 5,837,672 A | 11/1998 | Schenk et al. | |
| 5,849,298 A | 12/1998 | Weiner et al. | |
| 5,851,996 A * | 12/1998 | Kline | 514/12 |
| 5,854,204 A | 12/1998 | Findeis et al. | |
| 5,869,054 A | 2/1999 | Weiner et al. | |
| 5,869,093 A | 2/1999 | Weiner et al. | |
| 5,877,399 A | 3/1999 | Hsiao et al. | |
| 5,935,927 A | 8/1999 | Vitek et al. | |
| 5,955,079 A | 9/1999 | Mond et al. | |
| 5,955,317 A | 9/1999 | Suzuki et al. | |
| 5,958,883 A * | 9/1999 | Snow | 514/16 |
| 5,989,566 A | 11/1999 | Cobb et al. | |
| 6,057,367 A | 5/2000 | Slamler et al. | |
| 6,114,133 A | 9/2000 | Seubert et al. | |
| 6,150,091 A | 11/2000 | Pandolfo et al. | |
| 6,262,335 B1 | 7/2001 | Hsiao et al. | |
| 6,284,221 B1 | 9/2001 | Schenk et al. | |
| 6,294,171 B2 | 9/2001 | McMichael | |
| 6,417,178 B1 | 7/2002 | Klunk et al. | |
| 2001/0018053 A1 | 8/2001 | McMichael | |
| 2002/0009445 A1 | 1/2002 | Du et al. | |
| 2002/0077288 A1 | 6/2002 | Frangione | |
| 2001/0102261 | 8/2002 | Raso | |
| 2002/0136718 A1 | 9/2002 | Raso | |
| 2002/0162129 A1 | 10/2002 | Lannfell | |

FOREIGN PATENT DOCUMENTS

| | | |
|---|---|---|
| GB | 2 220 211 A | 1/1990 |
| GB | 2 335 192 A | 9/1999 |
| WO | WO 88/10120 A1 | 12/1988 |
| WO | WO 89/01343 A1 | 2/1989 |
| WO | WO 89/03687 A1 | 5/1989 |
| WO | WO 89/06242 A1 | 7/1989 |
| WO | WO 89/06689 A1 | 7/1989 |
| WO | WO 90/12870 A1 | 11/1990 |
| WO | WO 90/12871 A1 | 11/1990 |
| WO | WO 91/08780 A1 | 6/1991 |
| WO | WO 91/12818 A1 | 9/1991 |
| WO | WO 91/16819 * | 11/1991 |
| WO | WO 91/16819 A1 | 11/1991 |
| WO | WO 91/19810 A1 | 12/1991 |
| WO | WO 92/06708 A1 | 4/1992 |
| WO | WO 92/08187 A1 | 4/1992 |
| WO | WO 92/13069 A1 | 8/1992 |
| WO | WO 93/02189 A1 | 2/1993 |
| WO | WO 93/04194 A1 | 3/1993 |
| WO | WO 93/14200 A1 | 7/1993 |
| WO | WO 93/15760 A1 | 8/1993 |
| WO | WO 93/16724 A1 | 9/1993 |
| WO | WO 93/21950 A1 | 11/1993 |
| WO | WO 94/01772 A1 | 1/1994 |
| WO | WO 94/03615 A1 | 2/1994 |
| WO | WO 94/28412 A1 | 12/1994 |
| WO | WO 95/04151 A2 | 2/1995 |
| WO | WO 95/05853 A1 | 3/1995 |
| WO | WO 95/11008 A2 | 4/1995 |
| WO | WO 95/11311 A1 | 4/1995 |
| WO | WO 95/11994 A1 | 5/1995 |
| WO | WO 95/12815 A1 | 5/1995 |
| WO | WO 95/31996 A1 | 11/1995 |
| WO | WO 96/18900 A1 | 6/1996 |
| WO | WO 96/25435 A1 | 8/1996 |
| WO | WO 96/28471 A1 | 9/1996 |
| WO | WO 96/39176 A1 | 12/1996 |
| WO | WO 97/17613 A1 | 5/1997 |
| WO | WO 97/21728 A1 | 6/1997 |
| WO | WO 98/07850 A2 | 2/1998 |
| WO | WO 98/44955 A1 | 10/1998 |
| WO | WO 99/00150 A2 | 1/1999 |
| WO | WO 99/06545 * | 2/1999 |
| WO | WO 99/08066 A2 | 2/1999 |
| WO | WO 99/27911 A1 | 6/1999 |
| WO | WO 99/27944 A1 | 6/1999 |
| WO | WO 99/27949 A1 | 6/1999 |
| WO | WO 99/00021 A2 | 11/1999 |
| WO | WO 99/06545 A2 | 11/1999 |
| WO | WO 99/58564 A1 | 11/1999 |
| WO | WO 99/60024 A1 | 11/1999 |
| WO | WO 99/60024 * | 11/1999 |
| WO | WO 01/62284 A2 | 3/2000 |
| WO | WO 00/43039 A1 | 7/2000 |
| WO | WO 00/43049 A1 | 7/2000 |
| WO | WO 00/72870 A1 | 12/2000 |
| WO | WO 00/72876 A2 | 12/2000 |
| WO | WO 00/72876 A3 | 12/2000 |
| WO | WO 00/72880 A2 | 12/2000 |
| WO | WO 00/72880 A3 | 12/2000 |
| WO | WO 00/77178 A1 | 12/2000 |
| WO | WO 02/03911 A2 | 4/2001 |
| WO | WO 01/42306 A2 | 5/2001 |
| WO | WO 01/39796 A2 | 6/2001 |
| WO | WO 01/62801 A2 | 8/2001 |
| WO | WO 01/77167 A2 | 10/2001 |
| WO | WO 01/90182 A2 | 11/2001 |
| WO | WO 02/34878 A2 | 5/2002 |
| WO | WO 02/34777 A1 | 6/2002 |

OTHER PUBLICATIONS

Beasley, "Alzheimer's traced to proteins caused by aging," Reuters, Apr. 20, 2001 7:56 PM ET.

Bercovici et al., "Chronic Intravenous Injections of Antigen Induce and Maintain Tolerance in T Cell Receptor–Transgenic Mice," *Eur. J. Immunol.* 29:345–354 (1999).

Bickel et al., "Site Protected, Cationized Monoclonal Antibody Against Beta Amyloid as a Potential Diagnostic Imaging Technique for Alzheimer's Diseases," *Soc. for Neuroscience Abstracts* 18:764 (1992).

Blass, John P., "Immunologic Treatment of Alzheimer's Disease," *New England J. Medicine,* 341 (22):1694 (1999).

Bodmer et al., "Transforming Growth Factor–Beta Bound to Soluble Derivatives of the Beta Amyloid Precursor Protein of Alzheimer's Disease," *Biochem. Biophys. Res. Comm.,* 171(2):890–897 (1990).

Borchelt et al., "Accelerated Amyloid Deposition in the Brains of Transgenic Mice Coexpressing Mutant Presenilin 1 and Amyloid Precursor Proteins," *Neuron,* 19:939–945 (1997).

Boris–Lawrie et al., "Recent advances in retrovirus vector technology," *Cur. Opin. Genet Develop.,* 3: 102–109 (1993).

Brice et al., "Absense of the amyloid precursor protein gene mutation (APP717: Val–0>lle) in 85 cases of early onset Alzheimer's disease," *J. Neurology, Neurosurg. Psychiatry,* 56:112–115 (1993).

Cameron, "Recent Advances in Transgenic Technology," *Molecular Biotechnology,* 7:253–265 (1997).

Caputo et al., "Therapeutic approaches targeted at the amyloid proteins in Alzheimer's disease," *Clin. Neuropharm.,* 15:414A–414B (1992).

Chao et al., "Transforming Growth Factor–β Protects human Neurons Against β–Amyloid–Induced Injury," Soc. Neurosci. Abstracts, 19:513–7 (1993).

Chapman, Paul F., "Model behavior," Nature, 408:915–916 (2000).

Chemical Abstract database, Abstract of "Injection of Newborn Mice with Seven Chemical Adjuvants to Help Determine Their Safety in Use in Biologicals," Chemical Abstract database (Publication date unknown).

Chen, et al., "Neurodegenerative Alzheimer–like pathology in PDAPP 717V→F transgenic mice," Progress in Brain Research, Van Leeuwen et al. Eds, 117:327–337 (1998).

Chen, et al. A learning deficit related to age and beta–amyloid plaques in a mouse model of Alzheimer's disease. Nature, 408(6815):975–9 (2000).

Chen et al. "An Antibody to β Amyloid Precursor Protein Inhibits Cell–substratum Adhesion in Many Mammalian Cell Types," Neuroscience Letters 125:223–226 (1991).

Chung et al. "Uptake, Degradation, and Release of Fibrillar and Soluble Forms of Alzheimer's Amyloid β–Peptide by Microglial Cells," J. Biol. Chem., 274(45):32301–32308 (1999).

Coloma et al., "Transport Across the Primate Blood–Brain Barrier of a Genetically Engineered Chimeric Monoclonal Antibody to the Human Insulin Receptor," Pharm. Res., 17:266–274 (2000).

Conway et al., "Acceleration of oligomerization, not fibrillization, is a shared property of both α–synuclein mutations linked to early–onset Parkinson's disease: Implications for pathogenesis and therapy," PNAS, 97(2):571–576 (2000).

Cordell, B., "β–Amyloid formation as a potential therapeutic target for Alzheimer's disease," Ann. Rev. Pharmacol. Toxicol., 34:69–89 (1994).

Costa et al., "Immunoassay for transthyretin variants associated with amyloid neuropathy," Scand. J. Immunol., 38:177–182 (1993).

Daly, et al., "Detection of the membrane–retained carboxy–terminal tail containing polypeptides of the amyloid precursor protein in tissue from Alzheimer's Disease brain," Life Sci., 63:2121–2131 (1998).

Demattos et al., "Peripheral Anti Aβ Antibody Alters CNS An Plasma Aβ Clearance and Decreases Brain Aβ Burden in a Mouse Model of Alzheimer's Disease," Proc. Natl. Acad. Sci. USA, 10.1073/pnas.151261398 (2001).

Du, et al. Reduced levels of amyloid beta–peptide antibody in Alzheimer disease. Neurology. 57(5):801–5 (2001).

Duff et al., "Mouse model made," Nature, 373: 476–477 (1995).

Dumery et al., "β–Amyloid protein aggregation: its implication in the physiopathology of Alzheimer's disease," Pathol. Biol., 49:72–85 (2001).

Elan, "Elan and AHP Provide an Update on the Phase 2A Clinical Trial of AN–1792," Press Release. (Jan. 18, 2002).

Elan, "Elan and Wyeth Provide Update on Status of Alzheimer's Collaboration," Press Release (Mar. 1, 2002).

Elizan et al., "Antineurofilament antibodies in a postencephalitic and idiopathic Parkinson's disease," J. Neurol. Sciences, 59:341–347 (1983).

Esiri, "Is an effective immune Intervention for Alzheimer's disease in prospect?," Trends in Pharm. Sci., 22:2–3 (2001).

Felsenstein et al., "Processing of the β–amyloid precursor protein carrying the familial, Dutch–type, and a novel recombinant C–terminal mutation," Neuroscience Letters, 152:185–189 (1993).

Felsenstein et al., "Transgenic Rat and In–Vitro Studies of B–Amyloid Precursor Protein Processing;" Alzheimer's Parkinson's Diseases, Hanin et al. Ed., pp. 401–409, Plenum Press, New York, (1995).

Finch et al., "Evolutionary Perspectives on Amyloid and Inflammatory Features of Alzheimer Disease," Neurobiology of Aging, 17(5):809–815 (1996).

Fisher et al., "Expression of the amyloid precursor protein gene in mouse oocytes and embryos," PNAS, 88:1779–1782 (1991).

Flanders et al., "Altered expression of transforming growth factor–β in Alzheimer's disease," Neurology, 45:1561–1569 (1995).

Frenkel et al., "Generation of auto–antibodies towards Alzheimer's disease vaccination," Vaccine, 19:2615–2619 (2001).

Frenkel et al., "Immunization against Alzheimer's β–amyloid plaques via EFRH phage administration," PNAS USA, 97:11455–11459 (2000).

Frenkel et al., "N–terminal EFRH sequence of Alzheimer's β–amyloid peptide represents the epitope of its anti–aggregating antibodies," J. of Neuroimmunology, 88:85–90 (1998).

Frenkel et al., "High affinity binding of monoclonal antibodies to the sequential epitope EFRH of β–amyloid peptide is essential for modulation of fibrillar aggregation," J. of Neuroimmunology, 95:136–142 (1999).

Frenkel, et al., "Modulation of Alzheimer's β–amyloid neurotoxicity by site–directed single chain antibody," J. of Neuroimmunology, 106:23–31 (2000).

Friedland et al., "Development of an anti–Aβ monoclonal antibody for in vivo imaging of amyloid angiopathy in Alzheimer's disease," Mol. Neurology, 9:107–113 (1994).

Friedland, et al., "Neuroimaging of Vessel Amyloid in Alzheimer's Disease," in Cerebrovascular Pathology in Alzheimer's Disease, eds. de la Torre and Hachinski, New York Academy of Sciences, New York, New York (1997).

Games et al., "Alzheimer–type neuropathology in transgenic mice overexpressing V717F β–amyloid precursor protein," Nature, 373(6514): 523–527 (1995).

Games et al., "Prevention and Reduction of AD–type Pathology in PDAPP Mice Immunized with $A\beta_{1-42}$," Annals of the New York Academy of Science 920:274–84 (2000).

Gandy et al., "Amyloidogenesis in Alzheimer's disease: some possible therapeutic opportunities," TiPS, 13:108–113 (1992).

Gardella et al., "Intact Alzheimer amyloid precursor protein (APP) is present in platelet membranes and is encoded by platelet mRNA," Biochem. Biophys. Res. Comm., 173:1292–1298 (1990).

Gaskin et al., "Human antibodies reactive with beta–amyloid protein in Alzheimer's disease," J. Exp. Med., 177:1181–1186 (1993).

Geddes, "N–terminus truncated β–amyloid peptides and C–terminus truncated secreted forms of amyloid precursor protein: distinct roles in the pathogenesis of Alzheimer's disease," Neurobiology of Aging, 20:75–79 (1999).

Giulian, et al., "The HHQK Domain of B–Amyloid Provides a Structural Basis for the Immunopathology of Alzheimer's Disease," Journal of Biological Chem., 273:29719–29726 (1998).

Glenn et al., "Skin immunization made possible by cholera toxin," Nature, 391: 851 (1998).

Glenner et al., "Alzheimer's Disease and Downs Syndrome: Sharing of A Unique Cerebrovascular Amyloid Fibril Protein," *Biochemical and Biophysical Research Communications*, 122(3): 1131–1135 (1984).

Glenner et al., "Alzheimer's Disease: Initial Report of the Purification and Characterization of a Novel Cerebrovascular Amyloid Protein," *Biochemical and Biophysical Research Communications*, 120(3): 855–890 (1994).

Goate et al., "Segregation of a missense mutation in the amyloid precursor protein gene with familial Alzheimer's disease," *Nature*, 349:704–706 (1991).

Gonzales–Fernandez et al., "Low antigen dose favors selection of somatic mutants with hallmarks of antibody affinity maturation," *Immunology*, 93:149–153 (1998).

Gortner, *Outlines of Biochemistry*, pp. 322–323, John Wiley & Sons, Inc., New York (1949).

Gozes et al., "Neuroprotective strategy for Alzheimer disease: Intranasal administration of a fatty neuropeptide," *PNAS*, 93:427–432 (1996).

Gravina et al., "Amyloid β Protein (Aβ) in Alzheimer's Disease," *J. Biol. Chem.*, 270(13):7013–7016 (1995).

Grubeck–Loebenstein, et al., "Immunization with βamyloid: could T–cell activation have a harmful effect?" *TINS*, 23:114 (2000).

Gupta et al., "Differences in the immunogenicity of native and formalized cross reacting material (CRM197) of diptheria toxin in mice and guinea pigs and their implications on the development and control of diphtheria vaccine based on CRMs," *Vaccine*, 15(12/13): 1341–1343 (1997).

Haass et al.,"Amyloid beta–peptide is produced by cultured cells during normal metabolism," *Nature*, 359(6393):322–5 (1992).

Haga et al., "Synthetic Alzheimer amyloid β/A4 peptides enhance production of complement C3 component by cultured microglial cells," *Brain Research*, 601:88–94 (1993).

Hanan and Solomon, "Inhibitory effect of monoclonal antibodies on Alzherimer's β–amyloid peptide aggregation," *Int. J. Exp. Clin. Invest.*, 3:130–133 (1996).

Hanes et al., "New advances in microsphere–based single–dose vaccines," *Advanced Drug Delivery Reviews*, 28: 97–119 (1997).

Hardy, "Amyloid, the presenilins and Alzheimer's disease," *TINS*, 20(4): 154–159 (1997).

Hardy, John, "New Insights into the Genetics of Alzheimer's Disease," *Annals of Med.*, 28:255–258 (1996).

Harigaya, et al., "Modified amyloid β protein ending at 42 or 40 with different solubility accumulates in the brain of Alzheimer's disease," *Biochem. Biophys. Res. Comm.*, 211:1015–1022 (1995).

Harrington et al., "Characterisation of an epitope specific to the neuron–specific isoform of human enolase recognised by a monoclonal antibody raised against a synthetic peptide corresponding to the C–terminus of β/A4–protein," *Biochimica Biophysica Acta*, 1158:120–128 (1993).

Hazama, et al., "Intranasal Immunization Against Herpes Simplex Virus Infection by Using a Recombinant Glycoprotein D Fused With Immunomodulating Proteins, the B Subunit of *Escherichia Coli* Heat–Labile Enterotoxin and Interleukin–2" *Immunology*, vol. 78: 643–649 (1993).

Helmuth, L., "Further Progress on a β–Amyloid Vaccine," *Science*, 289:375 (2000).

Hilbich et al., :Human and rodent sequence analogs of Alzheimer's amyloid βA4 share similar properties and can be solubilized in buffers of pH 7.4, *Eur. J. Biochem.*, 201:61–69 (1991).

Hsiao et al., "Correlative Memory Deficits, Aβ Elevation, and Amyloid Plaques in Transgenic Mice," *Science*, 274: 99–102 (1996).

Huberman et al., "Correlation of cytokine secretion by mononuclear cells of Alzheimer's patients and their disease stage," *J. Neuroimmunology*, 52:147–152 (1994).

Hyman et al., "Molecular Epidemiology of Alzheimer's Disease," *N. E. J. Medicine*, 333(19):1283–1284 (1995).

Ikeda, et al., "Immunogold labeling of cerebrovascular and neuritic plaque amyloid fibrils in Alzheimer's disease with an anti–βprotein monoclonal antibody," *Lab. Invest.*, 57:446–449 (1987).

Itagaki et al., "Relationship of microglia and astrocytes to amyloid deposits of Alzheimer's disease," *J. Neuroimmunology*, 24:173–182 (1989).

Iwatsubo et al., "Visualization of Aβ42(43) and Aβ40 in Senile Plaques with End–Specific Aβ Monoclonals: Evidence That an Initially Deposited Species Is Aβ42(43)," *Neuron*, 13:45–53 (1994).

Jansen et al., "Immunotoxins: Hybrid Molecules Combining High Specificity and Potent Cytotoxicity," *Immun. Rev.*, 62: 185–216 (1982).

Janus, et al. A beta peptide immunization reduces behavioural impairment and plaques in a model of Alzheimer's diesease. Nature. 408(6815):979–82 (2000).

Jen, et al., "Preparation and purification of antisera against different regions or isoforms of b–amyloid precursor protein," *Brain Research Protocols*, 2:23–30 (1997).

Joachim et al., "Antibodies to Non–beta Regions of the Beta–amyloid Precursor Protein Detect a Subset of Senile Plaques," *Am. J. of Pathology* 138:373–378 (1991).

Jobling and Holmes, "Analysis of structure and function of the B subunit of cholera toxin by the use of site–directed mutagenesis," *Molecular Microbiology*, 5(7):1755–1767 (1991).

Jorbeck et al., "Artificial Salmonella Vaccines: *Salmonella typhimurium* O–antigen–Specific Oligosaccharide–Protein Conjugates Elicit Opsonizing Antibodies that Enhance Phagocytosis," *Infection and Immunity*, May:497–502 (1981).

Kalaria, R. N., "Serum amyloid P and related molecules associated with the acute–phase response in Alzheimer's disease," *Res. Immunology*, 143:637–641 (1992).

Katzav–Gozansky et al., "Effect of monoclonal antibodies in preventing carboxypeptidase A aggregation," *Biotechnol. Appl. Biochem.*, 23:227–230 (1996).

Kawabata et al., "Amyloid plaques, neurofibrillary tangles and neuronal loss in brains of transgenic mice overexpressing a C–terminal fragment of human amyloid precursor protein," *Nature*, 354:476–478 (1991).

Kida, et al., "Early amyloid–β deposits show different immunoreactivity to the amino– and carboxy–terminal regions of b–peptide in Alzheimer's disease and Down's syndrome brain," *Neuroscience Letters*, 193:105–108 (1995).

Konig et al., "Development and Characterization of a Monoclonal Antibody 369.2B Specific for the Carboxyl–Terminus of the βA4 Peptide," *Annals of NY Acad Sci.*, 777:344–355 (1996).

Lampert–Etchells et al., "Regional Localization of Cells Containing Complement C1q and C4 mRNAs in the Frontal Cortex During Alzheimer's Disease," *Neurodegeneration,* 2:111–121 (1993).

Langer, "New Methods of Drug Delivery," *Science,* 249: 1527–1532 (1990).

Lannfelt et al., "Alzheimer's disease: molecular genetics and transgenic animal models," *Behavioural Brain Res.,* 57:207–213 (1993).

Lansbury, Peter T., "Inhibition of amyloid formation: a strategy to delay the onset of Alzheimer's disease," *Curr. Ops. in Chemical Biology,* 1:260–267 (1997).

Lemere et al., "Mucosal Administration of Aβ Peptide Decreases Cerebral Amyloid Burden In Pd–App Transgenic Mice," *Society for Neuroscience Abstracts,* vol. 25, part I, Abstract 519.6, 29th Annual Meeting, (Oct. 23–28, 1999).

Lemere, et al., "Nasal Aβ treatment induces anti–Aβ antibody production and decreases cerebral amyloid burden in PD–APP mice," *Annals of the NY Acad. Sci.,* 920:328–331 (2000).

Li and Solomon, "Thermal Stabilization of Carboxypeptidease A as a Function of PH and Ionic Milleu," *Biochem. Mol. Biol. Int.,* 43(3):601–611 (1997).

Livingston et al., "The Hepatitis B Virus–Specific CTL Responses Induced in Humans by Lipopeptide Vaccination Are Comparable to Those Elicited by Acute Viral Infection," *J. Immunol.,* 159: 1383–1392 (1997).

Lopez et al., "Serum auto–antibodies in Alzheimer's disease," *Acta. Neurol. Scand.,* 84:441–444 (1991).

Majocha et al., "Development of a Monoclonal Antibody Specific for β/A4 Amyloid in Alzheimer's Disease Brain for Application to In Vitro Imaging of Amyloid Angiopathy," *The J. of Nuclear Med.* 33:2184–2189 (1992).

Mak, et al., "Polyclonals to b–amyloid (1–42) identify most plaque and vascular deposits in Alzheimer cortex, but not striatum, " *Brain Research,* 667:138–142 (1994).

Mann, et al., "Amyloid β protein (Aβ) depostion in chromosome 14–linked Alzheimer's disease. Predominance of $A\beta_{42(43)}$," *Annals of Neurology,* 40:149–156 (1996).

Mann, et al., "The extent of amyloid deposition in brain in patients with Down's syndrome does not depend upon the apolipoprotein E genotype," *Neuroscience Letters,* 196:105–108 (1995).

Masliah et al., "β–Amyloid peptides enhance α–synuclein accumulation and neuronal deficits in a transgenic mouse model linking Alzheimer's disease and Parkinson's disease," *PNAS,* 98(21):12245–12250 (2001).

Masters et al., "Amyloid Plaque core protein in Alzheimer Disease and Down Syndrome," *Proc. Natl. Acad. Sci. USA,* 82:4245–4249 (1985).

Mattson, MP. Cellular actions of beta–amyloid precursor protein and its soluble and fibrillogenic derivatives. Physiol Rev. 77(4):1081–132 (1997).

McGee et al., "The encapsulation of a model protein in poly (D, L lactide–co–glycolide) microparticles of various sizes: an evaluation of process reproducibility," *J. Micro. Encap.,* 14(2): 197–210 (1997).

McGeer, et al., "Immunohistochemical localization of beta–amyloid precursor protein sequences in Alzheimer and normal brain tissue by light and electron microscopy," *J. of Neuroscience Res.,* 31:428–442 (1992).

McNeal et al., "Stimulation of local immunity and protection in mice intramuscular immunization with triple– or double–layered rotavirus particles and QS–21," *Virology,* 243:158–166 (1998).

Meda et al., "Activation of microglial cells by β–amyloid protein and interferon–γ," *Nature,* 374:647–650 (1995).

Mena, et al., "Monitoring pathological assembly of tau and β–amyloid proteins in Alzheimer's disease," *Acta Neuropathol.,* 89:50–56 (1995).

Merluzzi, et al. Humanized antibodies as potential drugs for therapeutic use. Adv Clin Path. 4(2):77–85 (2000).

Miller et al., "Antigen–driven Bystander Suppression after Oral Administration of Antigens," *J. Exp. Med.,* 174:791–798 (1991).

Morgan, et al. A beta peptide vaccination prevents memory loss in an animal model of Alzheimer's disease. Nature. 408(6815):982–5 (2000).

Mori et al., "Mass Spectrometry of Purified Amyloid β Protein in Alzheimer's Disease," *J. Biol. Chem.,* 267(24):17082–17088 (1992).

Morris, et al., "The Consortium to Establish a registry for Alzheimer's Disease (CERAD)," *Neurology,* 39:1159–65 (1989).

Munch et al., "Potential neurotoxic inflammatory response to Aβ vaccination in humans," (2002) *J. Neural Transm.,* 109:1081–1087.

Munson ed., "Principals of Pharmacology: Basic Concepts & Clinical Applications," (1995), 47–48, Chapman & Hall, New York, New York.

Murphy et al., "Development of a Monoclonal Antibody Specific for the COOH–Terminal of β–Amyloid 1–42 and Its Immunohistochemical Reactivity in Alzheimer's Disease and Related Disorders," *Am. J. Pathology,* 144(5):1082–1088 (1994).

Mutschler et al., "Drug Actions: Basic Principles and Therapeutic Aspects," (1995) 7, 11–12, *medpharm* Scientific Publishers, Stuttgart, Germany.

Nakamura et al., "Histopathological studies on senile plaques and cerebral amyloid angiopathy in aged cynomologus monkeys," *Exp. Anim.,* 43:711–718 (1995).

Nakamura, et al., "Carboxyl end–specific monoclonal antibodies to amyloid β protein (Aβ) subtypes (Aβ40 and Aβ42(43)) differentiate Ab in senile plaques and amyloid angiopathy in brains of aged cynomolgus monkeys," *Neuroscience Letters,* 201:151–154 (1995).

Nakayama et al., "Histopathological studies of senile plaques and cerebral amyloidosis in cynomolgus monkeys," *J. of Med. Primatology,* 27:244–252 (1998).

Nathanson et al., "Bovine Spongiform Encephalopathy (BSE): Causes and Consequences of a Common Source Epidemic," *Am. J. Epidemiol.,* 145(11):959–969 (Jun. 1, 1997).

New York Times National, "Anti–Inflammatory Drugs May Impede Alzheimer's," (Feb. 20, 1994).

Newcombe and Cohen, "Solubility characteristics of isolated amyloid fibrils," *Biochim. Biophys. Acta,* 104:480–486 (1965).

Niemann, "Transgenic farm animals get off the ground;" *Transgenic Research* 7:73–75 (1998).

Pardridge et al., "Chimeric peptides as a vehicle for peptide pharmaceutical delivery through the blood–brain barrier," *Biochem. Biophys. Res. Comm.,* 146:307–313 (1987).

Paresce et al., "Microglial cells influence aggregates of the Alzheimer's disease amyloid beta–protein via a scavenger receptor," *Neuron*, 17:553–565 (Sep. 1996).

Paul et al., "Transdermal immunization with large proteins by means of ultradeformable drug carriers," *Eur. J. Immunol.*, 25:3521–3524 (1995).

Perutz et al., "Amyloid fibers are water–filed nanotubes," *PNAS*, 99(8):5591–5595 (2002).

Peterson, et al., "Recombinant Antibodies: Alternative Strategies for Developing and Manipulating Murine–Derived Monoclonal Antibodies," *Laboratory Animal Science*, 46(1):8–14 (1996).

Phillippe, et al. "Generation of monoclonal antibody to the carboxy–terminal domain of tau by Immunization with the amino–terminal domain of the amyloid precursor protein," *J. of Neuroscience Res.*, 46:709–719 (1996).

Prieels et al., "Synergistic adjuvants for vaccines," *Chemical Abstracts*, 120(8); p. 652, column 1, abstract 86406t (1994).

Quon et al., "Formation of β–Amyloid protein deposits in brains of transgenic mice," *Nature*, 352:239–241 (1991).

Raso, "Immunotherapy of Alzheimer's Disease," *Immunotherapy Weekly*, Abstract (Apr. 2, 1998).

Rogers et al., "Complement activation by β–amyloid in Alzheimer Disease," *PNAS*, 89:1–5 (1992).

Rossor et al., "Alzheimer's Disease Families with Amyloid Precursor Protein Mutations," *Annals of New York Academy of Sciences*, 695:198–202 (1993).

Rudinger, "Characteristics of the Amino Acids as Components of a Peptide Hormone Sequence," in *Peptide Hormones*, J.A. Parson, ed. University Park Press, Baltimore, pp. 1–7 (1976).

Saido et al., "Spatial Resolution of Fodrin Proteolysis in Postischemic Brain," *J. Biol. Chem.*, 268(33):25239–25243 (1993).

Saido et al., "Spatial Resolution of the Primary β–Amyloidogenic Process Induced in Postischemic Hippocampus," *J. Biol. Chem.*, 269(21):15253–15257 (1994).

Saito et al., "Vector–mediated delivery of $^{125}$I–labeled β–amyloid peptide $Ab^{1-40}$ through the blood–brain barrier and binding to Alzheimer disease amyloid of the $A\beta^{1-40}$ vector complex," *PNAS USA*, 92:10227–10231 (1995).

Saitoh, N. and K. Imai, "Immunological analysis of Alzheimer's disease using anti–β–protein monoclonal antibodies," *Sapporo Med. J.*, 60:309–320 (1991).

Sasaki et al., "Human choroid plexus is an uniquely involved area of the brain in amyloidosis: a histochemical, immunohistochemical and ultrastructural study," *Brain Res.*, 755:193–201 (1997).

Schenk et al., "Immunization with amyloid–β attenuates Alzheimer–disease–like pathology in the PDAPP mouse," *Nature*, 400:173–177 (1999).

Schenk, et al. Immunotherapy with beta–amyloid for Alzheimer's disease: a new frontier. DNA Cell Biol. 20(11):679–81 (2001).

Schenk et al., "Therapeutic Approaches Related to Amyloid–β Peptide and Alzheimer's Disease," *J. Med. Chem.*, 38(21):4141–4154 (1995).

Schenk, et al., "β–peptide immunization," *Arch. Nuerol.*, 57:934–936 (2000).

Selkoe, "Alzheimer's Disease: A Central Role for Amyloid," *J. Neuropathol. Exp. Neurol.*, 53(5): 438–447 (1994).

Selkoe, "Physiological production of the β–amyloid protein and the mechanism of Alzheimer's disease," *Trends in Neurosciences*, 16(10): 403–409 (1993).

Selkoe, D.J., "Imaging Alzheimer's Amyloid," *Nat. Biotech.*, 18:823–824 (2000).

Selkoe, Dennis J., "Alzheimer's Disease: Genotypes, Phenotype, and Treatments," *Science*, 275:630–631 (1997).

Selkoe, Dennis J., "Amyloid Protein and Alzheimer's Disease . . . ," *Scientific American*, pp. 68–78 (Nov., 1991).

Selkoe, Dennis J., "In the Beginning . . . ," *Nature*, 354:432–433 (1991).

Selkoe, The cell biology of beta–amyloid precursor protein and presenilin in Alzheimer's disease. Trends Cell Biol. 8(11):447–43 (1998).

Selkoe, Dennis J., "The Molecular pathology of Alzheimer's Disease," *Neuron*, 6:487–498 (1991).

Seubert et al., "Isolation and quantification of soluble Alzheimer's β–peptide from biological fluids," *Nature*, 359: 325–327 (1992).

Shiosaka, S., "Attempts to make models for Alzheimer's disease," *Neuroscience Res.*, 13:237–255 (1992).

Sigmund, "Viewpoint: Are Studies in Genetically Altered Mice Out of Control," *Arterioscler Thromb Vasc Biol.*, 20:1425–1429 (2000).

Sigurdsson, et al. In vivo rversal of amyloid–beta lesions in rat brain. J Neuropathol Exp Neurol. 59(1):11–17 (2000).

Sinha, et al. Recent advances in the understanding of the processing of APP to beta amyloid peptide. Ann N Y Acad Sci. 920:206–8 (2000).

Skolnick and Fetrow, "From genes to protein structure and function: novel applications of computational approaches in the genomic era," *Trends in Biotech*, 18(1):34–39 (2000).

Small, et al. Alzheimer's disease and Abeta toxicity: from top to bottom. Nat Rev Neurosci. 2(8):595–8 (2001).

Smits et al., "Prion Protein and Scraple Susceptibility," *Vet. Quart.*, 19(3): 101–105 (1997).

Solomon and Goldstein, "Modulation of The Catalytic Pathway of Carboxypeptidase A by Conjugation with Polyvinly Alcohols," *Adv. Mol. Cell Biology*, 15A:33–45 (1996).

Solomon et al., "Dissaggregation of Alzheimer β–amyloid by site–directed mAb," *PNAS*, 94:4109–4112 (1997).

Solomon et al., "Monoclonal antibodies inhibit in vitro fibrillar aggregation of the Alzheimer β–amyloid peptide," *PNAS*, 93:452–455 (1996).

Soto, et al. Beta sheet breaker peptides inhibit fribrillogenesis in a rat brain model of amyloidosis: implications for Alzheimer's therapy. Nat Med. 4(7):822–6 (1998).

Southwick et al., "Assessment of Amyloid β protein in Cerebrospinal fluid as an Aid in the Diagnosis of Alzheimer's Disease," *J. Neurochemistry*, 66:259–265 (1996).

St. George–Hysop, Peter H. and David A. Westaway, Antibody clears senile plaques, *Nature*, 40:116–117 (1999).

Stein and Johnson, "Lack of Neurodegeneration in Transgenic Mice Overexpressing Mutant Amyloid Precursor Protein is Associated with Increased Levels of Transthyretin and Activation of Cell Survival Pathways," *The Journal of Neuroscience*, 22(17):7380–7388 (Sep. 1, 2002).

Stoute et al., "A Preliminary Evaluation of a Recombinant Circumsporozoite Protein Vaccine Against *Plasmodium Falciparum* Malaria", *N. Engl. J. Med.*, 336(2):88–91 (1997).

Sturchler–Pierrat et al., "Two amyloid precursor protein transgenic mouse models with Alzheimer disease–like pathology," *PNAS*, 94: 13287–13292 (1997).

Szendrei, et al., "The effects of aspartic acid–bond isomerization on in vitro properties of the amyloid β–peptide as modeled with N–terminal decapeptide fragments," *Int. J. Peptide Protein Res.*, 47:289–296 (1996).

Tanaka et al., "NC-1900, and active fragment analog of arginine vasopressin, improves learning and memory deficits induced by beta–amyloid protein in rats," *European J. Pharmacology*, 352:135–142 (1998).

Tennent et al., "Serum amyloid P component prevents proteolysis of the amyloid fibrils of Alzheimer's disease and systemic amyloidosis," *PNAS*, 92:4299–4303 (1995).

Thorsett, E.D. and L.H. Latimer, "Therapeutic aproaches to Alzheimer's disease," *Curr. Op. in Chem. Biology*, 4:377–382 (2000).

Tjernberg et al., "Arrest of β–amyloid fibril formation by a pentapeptide ligand," *Journal of Biological Chemistry*, 271:8545–8548 (1996).

Trieb et al., "Is Alzheimer beta amyloid precursor protein (APP) an autoantigen? Peptides corresponding to parts of the APP sequence stimulate T lymphocytes in normals but not in patients with Alzheimer's disease," *Immunobiology* 191(2–3):114–115 Abstract C.37, (1994).

Van Gool et al., "Concentrations of amyloid–β protein in cerebrospinal fluid increase with age in patients free from neurodegenerative disease," *Neuroscience Letters*, 172:122–124 (1994).

Vehmas, et al. beta–Amyloid peptide vaccination results in marked changes in serum and brain Abeta levels in APPswe/PS1 DeltaE9 mice, as detected by SELDI–TOF–based ProteinChip® technology. DNA Cell Biol. (11):713 21 (2001).

Verbeek et al., "Accumulation of Intercellular Adhesion Molecule–1 in Senile Plaques in Brain Tissue of patients with Alzheimer's Disease," *Amer. Journ. Pathology*, 144(1):104–116 (1994).

Walker et al., "Labeling of Cerebral Amyloid In Vivo with a Monoclonal Antibody," *J. Neuropath. Exp. Neurology*, 53(4):377–383 (1994).

Weiner et al., "Nasal administration of amyloid–β peptide decreases cerebral amyloid burden in a mouse model of Alzheimer's disease," *Annals of Neurology*, 48:567–579 (2000).

Weiner et al., "Oral Tolerance: Immunologic Mechanisms and Treatment of Animal and Human Organ–Specific Autoimmune Diseases by Oral Administration of Autoantigens," *Annu. Rev. Immunol.*, 12:809–837 (1994).

Weissmann et al., "Bovine spongiform encephalopathy and early onset variant Creutzfeldt–Jakob disease," *Curr. Opin. Neurobiol.*, 7:695–700 (1997).

Wen, G.Y., "Alzheimer's Disease and Risk Factors," *J. Food Drug Analysis*, 6(2):465–476 (1998).

Wengenack et al., "Targeting Alzheimer amyloid plaques in vivo," *Nature Biotech.*, 18:868–824 (2000).

Wong et al., "Neuritic Plaques and Cerebrovascular Amyloid in Alzheimer Disease are Antigenically Related," *Proc. Natl. Acad. Sci. USA*, 82:8729–8732 (1985).

Wood et al., "Amyloid precursor protein processing and Aβ42 deposition in a transgenic mouse model of Alzheimer disease," *PNAS*, 94: 1550–1555 (1997).

Wu, et al., "Drug targeting of peptide readiopharmaceutical through the primate blood–brain barrier in vivo with a monoclonal antibody to the human insulin receptor," *J. Clin. Invest.*, 100:1804–1812 (1997).

Yamaguchi et al., Diffuse plaques associated with astroglial amyloid β protein, possibly showing a disappearing stage of senile plaques, *Acta Neuropathol.*, 95:217–222 (1998).

Younkin, "Amyloid β vaccination; reduced plaques and improved cognition," *Nature Medicine*, 7:18–19 (2001).

Check, "Battle of the Mind," *Nature* 422:370–372 (Mar. 2003).

Nicoll et al., "Neuropathology of human Alzheimer's disease after immunization with amyloid–β peptide: a case report," *Nature Medicine*, 9(4):448–452 (Apr. 2003).

* cited by examiner

CORTEX

| PBS CONTROL | | UNTREATED CONTROL | |
|---|---|---|---|
| 624-165 | 272 | 764-181 | 3470 |
| 625-166 | 1802 | 785-182 | 171 |
| 626-167 | 62 | 766-183 | 91 |
| 633-168 | 4696 | 767-184 | 6692 |
| 634-169 | 3090 | 768-185 | 1353 |
| 671-170 | 2417 | 771-186 | 1153 |
| 672-171 | 2840 | 772-187 | 3800 |
| 829-172 | 3320 | 780-188 | 3740 |
| 830-173 | 1833 | 843-189 | 163 |
| 831-174 | 416 | 844-190 | 122 |
| 792-175 | 126 | 845-191 | 427 |
| 793-176 | 2559 | 846-192 | 2674 |
| 794-177 | 289 | 887-193 | 453 |
| 732-178 | 179 | 888-194 | 2996 |
| 733-179 | 1329 | 889-195 | 1075 |
| 734-180 | 5665 | | |
| MEDIAN p VALUE (M-W) | 1817 | MEDIAN p VALUE (M-W) | 1153 |
| MEAN | 1931 | MEAN | 1825 |
| ST. DEV. | 1718 | ST. DEV. | 1769 |
| % CV | 89 | % CV | 97 |
| p VALUE (t TEST) | n=16 | p VALUE (t TEST) | n=15 |

*FIG. 15A*

CORTEX

| 2 mg ALUM 100 μg AN1528 | | 50 μg MPL 100 μg AN1528 | |
|---|---|---|---|
| 660-083 | 295 | 643-105 | 385 |
| 661-084 | 3180 | 644-106 | 2640 |
| 662-085 | 2480 | 645-107 | 2403 |
| 663-086 | 3014 | 654-108 | 1741 |
| 664-087 | 5870 | 655-109 | 3053 |
| 665-088 | 5978 | 656-110 | 5990 |
| 693-089 | 1620 | 678-111 | 3360 |
| 694-090 | 35 | 679-112 | 1230 |
| 695-091 | 3400 | 704-114 | 2680 |
| 697-092 | 2630 | 705-115 | 78 |
| 698-093 | 983 | 706-116 | 1290 |
| 699-094 | 5327 | 729-117 | 3180 |
| 701-095 | 1862 | 730-118 | 1833 |
| 702-096 | 1849 | 731-119 | 4590 |
| 703-097 | 2239 | 736-120 | 1112 |
| 739-098 | 806 | 737-121 | 1653 |
| 740-099 | 5303 | 757-122 | 992 |
| 741-100 | 459 | 758-123 | 4692 |
| 800-103 | 154 | 808-124 | 785 |
| 801-104 | 852 | 809-125 | 244 |
|  |  | 810-126 | 32 |
| MEDIAN p VALUE (M-W) | 2051 | MEDIAN p VALUE (M-W) | 1741 |
| MEAN ST. DEV. % CV p VALUE (t TEST) | 2407 1913 79 n=20 | MEAN ST. DEV. % CV p VALUE (t TEST) | 2140 1659 78 n=21 |

*FIG. 15B*

CORTEX

| 25 μg QS21<br>100 μg AN1528 | | CFA/IFA<br>100 μg AN1792 | |
|---|---|---|---|
| 615-128 | 1257 | 539-068 | 693 |
| 616-129 | 361 | 640-069 | 508 |
| 617-130 | 1008 | 641-070 | 440 |
| 536-131 | 3290 | 642-071 | 467 |
| 637-132 | 2520 | 690-072 | 42 |
| 638-133 | 3880 | 691-073 | 2491 |
| 744-134 | 627 | 692-074 | 121 |
| 745-135 | 58 | 795-075 | 137 |
| 746-136 | 2610 | 796-076 | 822 |
| 747-137 | 1509 | 797-077 | 475 |
| 769-138 | 1788 | 748-087 | 600 |
| 770-139 | 988 | 749-079 | 78 |
| 773-140 | 1199 | 750-080 | 1267 |
| 774-141 | 339 | 751-081 | 1351 |
| 775-142 | 402 | 761-082 | 69 |
| 776-143 | 537 | | |
| 840-144 | 1119 | | |
| 841-145 | 194 | | |
| 821-146 | 1259 | | |
| 822-147 | 5413 | | |
| 823-148 | 2233 | | |
| MEDIAN<br>p VALUE (M-W) | 1199 | MEDIAN<br>p VALUE (M-W) | 475<br>0.0481 |
| MEAN<br>ST. DEV.<br>% CV<br>p VALUE (t TEST) | 1552<br>1364<br>88<br>n=21 | MEAN<br>ST. DEV.<br>% CV<br>p VALUE (t TEST) | 637<br>655<br>103<br>0.0106<br>n=15 |

FIG. 15C

CORTEX

| 5 μg THIMEROSAL/PBS 10 μg AN1792 | | 2 mg ALUM 100 μg AN1792 | |
|---|---|---|---|
| 635-149 | 1337 | 610-001 | 432 |
| 669-150 | 4644 | 611-002 | 1012 |
| 670-151 | 6335 | 612-003 | 3607 |
| 673-152 | 3700 | 613-004 | 508 |
| 674-153 | 2750 | 620-005 | 465 |
| 676-154 | 1687 | 621-006 | 16 |
| 681-156 | 185 | 622-007 | 28 |
| 682-157 | 8031 | 623-008 | 217 |
| 683-158 | 3450 | 708-009 | 2738 |
| 754-159 | 157 | 709-010 | 927 |
| 755-160 | 6857 | 710-011 | 1609 |
| 756-161 | 482 | 716-012 | 1608 |
| 805-162 | 524 | 784-014 | 3890 |
| 806-163 | 397 | 785-015 | 1614 |
| 807-164 | 234 | 786-018 | 285 |
| | | 787-017 | 3102 |
| | | 788-018 | 1617 |
| | | 789-019 | 1474 |
| | | 815-020 | 424 |
| | | 816-021 | 1375 |
| | | 817-022 | 2323 |
| MEDIAN p VALUE (M-W) | 1687 | MEDIAN p VALUE (M-W) | 1375 0.5000 |
| MEAN ST. DEV. % CV p VALUE (t TEST) | 2718 2685 99 n=15 | MEAN ST. DEV. % CV p VALUE (t TEST) | 1394 1166 84 0.2650 n=21 |

FIG. 15D

CORTEX

| 50 µg MPL 100 µg AN1792 | | 25 µg QS21 100 µg AN1792 | |
|---|---|---|---|
| 646-023 | 2002 | 627-045 | 91 |
| 647-024 | 147 | 628-046 | 3397 |
| 648-025 | 1304 | 631-049 | 3702 |
| 649-026 | 34 | 632-050 | 1776 |
| 650-027 | 980 | 667-052 | 1832 |
| 724-028 | 1282 | 668-053 | 3023 |
| 726-030 | 1966 | 686-054 | 189 |
| 727-031 | 733 | 687-055 | 891 |
| 720-032 | 2563 | 688-056 | 240 |
| 721-033 | 5563 | 689-057 | 110 |
| 802-034 | 113 | 712-059 | 3311 |
| 803-035 | 671 | 825-061 | 1009 |
| 804-036 | 51 | 826-082 | 18165 |
| 811-037 | 613 | 827-063 | 73 |
| 812-038 | 332 | 828-064 | 78 |
| 813-039 | 1454 | 837-065 | 1051 |
| 814-040 | 2441 | 838-066 | 270 |
| 833-014 | 742 | 839-067 | 371 |
| 834-042 | 40 | | |
| 836-044 | 807 | | |
| MEDIAN p VALUE (M-W) | 774 0.1710 | MEDIAN p VALUE (M-W) | 950 0.4076 |
| MEAN ST. DEV. % CV p VALUE (t TEST) | 1192 1299 109 0.1506 n=21 | MEAN ST. DEV. % CV p VALUE (t TEST) | 2199 4187 190 0.8131 n=18 |

*FIG. 15E*

SEQUENCE LISTING

```
<160> NUMBER OF SEQ ID NOS: 34

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:influenza
      hemagglutinin HA 307-319  universal T-cell epitope

<400> SEQUENCE: 1

Pro Lys Tyr Val Lys Gln Asn Thr Leu Lys Leu Ala Thr
  1               5                  10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence:PADRE
      universal T-cell epitope
<220> FEATURE:
<221> NAME/KEY: MOD_RES
<222> LOCATION: (3)
<223> OTHER INFORMATION: Xaa = any amino acid

<400> SEQUENCE: 2

Ala Lys Xaa Val Ala Ala Trp Thr Leu Lys Ala Ala Ala
  1               5                  10

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence:malaria CS
      T3 epitope universal T-cell epitope
```

-continued

```
<400> SEQUENCE: 3

Glu Lys Lys Ile Ala Lys Met Glu Lys Ala Ser Ser Val Phe Asn Val
  1               5                  10                  15

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:Hepatitis B
      surface antigen HBsAg 19-28 universal T-cell
      epitope

<400> SEQUENCE: 4

Phe Phe Leu Leu Thr Arg Ile Leu Thr Ile
  1               5                  10

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence:heat shock
      protein 65 hsp65 153-171 universal T-cell epitope

<400> SEQUENCE: 5

Asp Gln Ser Ile Gly Asp Leu Ile Ala Glu Ala Met Asp Lys Val Gly
  1               5                  10                  15

Asn Glu Gly

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence:bacillus
      Calmette-Guerin universal T-cell epitope

<400> SEQUENCE: 6

Gln Val His Phe Gln Pro Leu Pro Pro Ala Val Val Lys Leu
  1               5                  10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence:tetanus
      toxoid TT 830-844 universal T-cell epitope

<400> SEQUENCE: 7

Gln Tyr Ile Lys Ala Asn Ser Lys Phe Ile Gly Ile Thr Glu Leu
  1               5                  10                  15

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence:tetanus
      toxoid TT 947-967 universal T-cell epitope

```
<400> SEQUENCE: 8

Phe Asn Asn Phe Thr Val Ser Phe Trp Leu Arg Val Pro Lys Val Ser
 1               5                  10                  15
Ala Ser His Leu Glu
            20

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence:HIV gp120 T1
      universal T-cell epitope

<400> SEQUENCE

```
<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence:AN 90576
      (Abeta 3-9/tetanus toxoid 830-844 in a MAP4 configuration)

<400> SEQUENCE: 13

Glu Phe Arg His Asp Ser Gly Gln Tyr Ile Lys Ala Asn Ser Lys Phe
 1               5                  10                  15

Ile Gly Ile Thr Glu Leu
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence:AN90562
      (Abeta 1-7/peptide on linear confornmation)
<220> FEATURE:
<221> NAME/KEY: MOD_RES
<222> LOCATION: (3)
<223> OTHER INFORMATION: Xaa = any amino acid

<400> SEQUENCE: 14

Ala Lys Xaa Val Ala Ala Trp Thr Leu Lys Ala Ala Ala Asp Ala Glu
 1               5                  10                  15

Phe Arg His Asp
            20

<210> SEQ ID NO 15
<211> LENGTH: 34
<212> TYPE: PRT
<213> ORGANISM: Artificial Sequence
<220> FEATURE:
<223> OTHER INFORMATION: Description of Artificial Sequence:AN90543
      (Abeta 1-7 X 3/peptide in linear conformation)
<220> FEATURE:
<221> NAME/KEY: MOD_RES
<222> LOCATION: (24)
<223> OTHER INFORMATION: Xaa = any amino acid

<400> SEQUENCE: 15

Asp Ala Glu Phe Arg His Asp Asp Ala Glu Phe Arg His Asp Ala
 1               5                  10                  15

Glu Phe Arg His Asp Ala Lys Xaa Val Ala Ala Trp Thr Leu Lys Ala
            20                  25                  30

Ala Ala

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence:fusion
      protein with Abeta immunogenic epitope
<220> FEATURE:
<221> NAME/KEY: MOD_RES
<222> LOCATION: (3)
<223> OTHER INFORMATION: Xaa = any amino acid
```

```
<400> SEQUENCE: 16

Ala Lys Xaa Val Ala Ala Trp Thr Leu Lys Ala Ala Ala Asp Ala Glu
 1               5                  10                  15

Phe Arg His Asp Asp Ala Glu Phe Arg His Asp Asp Ala Glu Phe Arg
             20                  25                  30

His Asp

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence:fusion
      protein with Abeta immunogenic epitope
<220> FEATURE:
<221> NAME/KEY: MOD_RES
<222> LOCATION: (10)
<223> OTHER INFORMATION: Xaa = any amino acid

<400> SEQUENCE: 17

Asp Ala Glu Phe Arg His Asp Ala Lys Xaa Val Ala Ala Trp Thr Leu
 1               5                  10                  15

Lys Ala Ala Ala
             20

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence:fusion
      protein with Abeta immunogenic epitope

<400> SEQUENCE: 18

Asp Ala Glu Phe Arg His Asp Ile Ser Gln Ala Val His Ala Ala His
 1               5                  10                  15

Ala Glu Ile Asn Glu Ala Gly Arg
             20

<210> SEQ ID NO 19
<211> LENGTH: 24
<212> TYPE: PRT
<213> ORGANISM: Artificial Sequence
<220> FEATURE:
<223> OTHER INFORMATION: Description of Artificial Sequence:fusion
      protein with Abeta immunogenic epitope

<400> SEQUENCE: 19

Phe Arg His Asp Ser Gly Tyr Ile Ser Gln Ala Val His Ala Ala His
 1               5                  10                  15

Ala Glu Ile Asn Glu Ala Gly Arg
             20

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence:fusion
      protein with Abeta immunogenic epitope
```

```
<400> SEQUENCE: 20

Glu Phe Arg His Asp Ser Gly Ile Ser Gln Ala Val His Ala Ala His
 1               5                  10                  15

Ala Glu Ile Asn Glu Ala Gly Arg
            20

<210> SEQ ID NO 21
<211> LENGTH: 34
<212> TYPE: PRT
<213> ORGANISM: Artificial Sequence
<220> FEATURE:
<223> OTHER INFORMATION: Description of Artificial Sequence:fusion
      protein with Abeta immunogenic epitope

<400> SEQUENCE: 21

Pro Lys Tyr Val Lys Gln Asn Thr Leu Lys Leu Ala Thr Asp Ala Glu
 1               5                  10                  15

Phe Arg His Asp Asp Ala Glu Phe Arg His Asp Asp Ala Glu Phe Arg
                20                  25                  30

His Asp

<210> SEQ ID NO 22
<211> LENGTH: 27
<212> TYPE: PRT
<213> ORGANISM: Artificial Sequence
<220> FEATURE:
<223> OTHER INFORMATION: Description of Artificial Sequence:fusion
      protein with Abeta immunogenic epitope

<400> SEQUENCE: 22

Asp Ala Glu Phe Arg His Asp Pro Lys Tyr Val Lys Gln Asn Thr Leu
 1               5                  10                  15

Lys Leu Ala Thr Asp Ala Glu Phe Arg His Asp
                20                  25

<210> SEQ ID NO 23
<211> LENGTH: 34
<212> TYPE: PRT
<213> ORGANISM: Artificial Sequence
<220> FEATURE:
<223> OTHER INFORMATION: Description of Artificial Sequence:fusion
      protein with Abeta immunogenic epitope

<400> SEQUENCE: 23

Asp Ala Glu Phe Arg His Asp Ala Glu Phe Arg His Asp Ala
 1               5                  10                  15

Glu Phe Arg His Asp Pro Lys Tyr Val Lys Gln Asn Thr Leu Lys Leu
                20                  25                  30

Ala Thr

<210> SEQ ID NO 24
<211> LENGTH: 27
<212> TYPE: PRT
<213> ORGANISM: Artificial Sequence
<220> FEATURE:
<223> OTHER INFORMATION: Description of Artificial Sequence:fusion
      protein with Abeta immunogenic epitope

<400> SEQUENCE: 24

Asp Ala Glu Phe Arg His Asp Ala Glu Phe Arg His Asp Pro Lys
 1               5                  10                  15

Tyr Val Lys Gln Asn Thr Leu Lys Leu Ala Thr
                20                  25
```

```
<210> SEQ ID NO 25
<211> LENGTH: 136
<212> TYPE: PRT
<213> ORGANISM: Artificial Sequence
<220> FEATURE:
<223> OTHER INFORMATION: Description of Artificial Sequence:fusion
      protein with Abeta immunogenic epitope

<400> SEQUENCE: 25

Asp Ala Glu Phe Arg His Asp Pro Lys Tyr Val Lys Gln Asn Thr Leu
1               5                   10                  15

Lys Leu Ala Thr Glu Lys Lys Ile Ala Lys Met Glu Lys Ala Ser Ser
            20                  25                  30

Val Phe Asn Val Gln Tyr Ile Lys Ala Asn Ser Lys Phe Ile Gly Ile
        35                  40                  45

Thr Glu Leu Phe Asn Asn Phe Thr Val Ser Phe Trp Leu Arg Val Pro
    50                  55                  60

Lys Val Ser Ala Ser His Leu Glu Asp Ala Glu Phe Arg His Asp Asp
65                  70                  75                  80

Ala Glu Phe Arg His Asp Asp Ala Glu Phe Arg His Asp Ala Glu
                85                  90                  95

Phe Arg His Asp Gln Tyr Ile Lys Ala Asn Ser Lys Phe Ile Gly Ile
            100                 105                 110

Thr Glu Leu Phe Asn Asn Phe Thr Val Ser Phe Trp Leu Arg Val Pro
        115                 120                 125

Lys Val Ser Ala Ser His Leu Glu
    130                 135

<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence:fusion
      protein with Abeta immunogenic epitope

<400> SEQUENCE: 26

Asp Ala Glu Phe Arg His Asp Gln Tyr Ile Lys Ala Asn Ser Lys Phe
1               5                   10                  15

Ile Gly Ile Thr Glu Leu Cys Phe Asn Asn Phe Thr Val Ser Phe Trp
            20                  25                  30

Leu Arg Val Pro Lys Val Ser Ala Ser His Leu Glu
            35                  40

<210> SEQ ID NO 27
<211> LENGTH: 51
<212> TYPE: PRT
<213> ORGANISM: Artificial Sequence
<220> FEATURE:
<223> OTHER INFORMATION: Description of Artificial Sequence:fusion
      protein with Abeta immunogenic epitope

<400> SEQUENCE: 27

Asp Ala Glu Phe Arg His Asp Gln Tyr Ile Lys Ala Asn Ser Lys Phe
1               5                   10                  15

Ile Gly Ile Thr Glu Leu Cys Phe Asn Asn Phe Thr Val Ser Phe Trp
            20                  25                  30

Leu Arg Val Pro Lys Val Ser Ala Ser His Leu Glu Asp Ala Glu Phe
            35                  40                  45

Arg His Asp
    50
```

```
<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence:fusion
      protein with Abeta immunogenic epitope on a 2 branched
      resin of Lys-Gly-Cys

<400> SEQUENCE: 28

Asp Ala Glu Phe Arg His Asp Gln Tyr Ile Lys Ala Asn Ser Lys Phe
 1               5                  10                  15

Ile Gly Ile Thr Glu Leu
            20

<210> SEQ ID NO 29
<211> LENGTH: 26
<212> TYPE: PRT
<213> ORGANISM: Artificial Sequence
<220> FEATURE:
<223> OTHER INFORMATION: Description of Artificial Sequence:synuclein
      fusion protein in MAP-4 configuration

<400> SEQUENCE: 29

Glu Gln Val Thr Asn Val Gly Gly Ala Ile Ser Gln Ala Val His Ala
 1               5                  10                  15

Ala His Ala Glu Ile Asn Glu Ala Gly Arg
            20                  25

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence:Abeta 1-12
      peptide with Cys added

<400> SEQUENCE: 30

Asp Ala Glu Phe Arg His Asp Ser Gly Tyr Glu Val Cys
 1               5                  10

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence:Abeta 1-5
      peptide with Cys added

<400> SEQUENCE: 31

Asp Ala Glu Phe Arg Cys
 1               5

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence:Abeta 33-42
      peptide with Cys added
<220> FEATURE:
<221> NAME/KEY: MOD_RES
<222> LOCATION: (2)
<223> OTHER INFORMATION: Xaa = amino-heptanoic acid

<400> SEQUENCE: 32

Cys Xaa Gly Leu Met Val Gly Gly Val Val Ile Ala
 1               5                  10
```

```
<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence:Abeta 13-28
      peptide with Cys added
<220> FEATURE:
<221> NAME/KEY: MOD_RES
<222> LOCATION: (1)
<223> OTHER INFORMATION: Xaa = acetyl-asparagine

<400> SEQUENCE: 33

Xaa His His Gln Lys Leu Val Phe Phe Ala Glu Asp Val Gly Ser
 1               5                  10                  15

Asn Lys Gly Gly Cys
                 20

<210> SEQ ID NO 34
<211> LENGTH: 42
<212> TYPE: PRT
<213> ORGANISM: Artificial Sequence
<220> FEATURE:
<223> OTHER INFORMATION: Description of Artificial Sequence:Abeta 42

<400> SEQUENCE: 34

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40
```

PHARMACEUTICAL COMPOSITIONS AND METHODS FOR TREATMENT OF AMYLOID DISEASES

This application is a continuation of U.S. application Ser. No. 09/585,817, filed Jun. 1, 2000, which claims the benefit under 35 U.S.C. 119(e) of U.S. application Ser. No. 60/137,010, filed Jun. 1, 1999, which is hereby incorporated herein in its entirety. U.S. application Ser. No. 09/585,817 filed Jun. 1, 2000 is also a continuation-in-part of U.S. application Ser. No. 09/580,015, filed May 26, 2000.

FIELD OF THE INVENTION

The invention relates to compositions and methods of treatment of amyloid-related conditions in humans and other mammalian vertebrates.

BACKGROUND OF THE INVENTION

Amyloidosis is a general term that describes a number of diseases characterized by extracellular deposition of protein fibrils, which form numerous "amyloid deposits," which may occur in localized sites or systemically. The fibrillar composition of these deposits is an identifying characteristic for the various forms of amyloid disease. For example, intracerebral and cerebrovascular deposits composed primarily of fibrils of beta amyloid peptide (β-AP) are characteristic of Alzheimer's disease (both familial and sporadic forms), islet amyloid protein peptide (IAPP; amylin) is characteristic of the fibrils in pancreatic islet cell amyloid deposits associated with type II diabetes, and β2-microglobulin is a major component of amyloid deposits which form as a consequence of long term hemodialysis treatment. More recently, prion-associated diseases, such as Creutzfeld-Jacob disease, have also been recognized as amyloid diseases.

The various forms of disease have been divided into classes, mostly on the basis of whether or not the amyloidosis is associated with an underlying systemic illness. Thus, certain disorders are considered to be primary amyloidoses, in which there is no evidence for preexisting or coexisting disease. In general, primary amyloidoses of the disease are characterized by the presence of "amyloid light chain-type" (AL-type) protein fibrils, so named for the homology of the N-terminal region of the AL fibrils to the variable fragment of immunoglobulin light chain (kappa or lambda).

Secondary or "reactive" amyloidosis is characterized by deposition of AA type fibrils derived from serum amyloid A protein (ApoSSA). These forms of amyloidosis are characterized by an underlying chronic inflammatory or infectious disease state (e.g., rheumatoid arthritis, osteomyelitis, *tuberculosis*, leprosy).

Heredofamilial amyloidoses may have associated neuropathic, renal, or cardiovascular deposits of the ATUR transthyretin type. Other Heredofamilial amyloidoses include other syndromes and may have different amyloid components (e.g., familial Mediterranean fever which is characterized by AA fibrils). Other forms of amyloidosis include local forms, characterized by focal, often tumor-like deposits that occur in isolated organs. Other amyloidoses are associated with aging, and are commonly characterized by plaque formation in the heart or brain. Also common are amyloid deposits associated with long term hemodialysis. These and other forms of amyloid disease are summarized in Table 1. (Tan, S. Y. and Pepys, Histopathology 25:403–414, 1994; Harrison's Handbook of Internal Medicine, 13th Ed., Isselbacher, K. J., et al, eds, McGraw-Hill, San Francisco, 1995).

TABLE 1

Classification of Amyloid Diseases

| Amyloid Protein/ Peptide | Protein Precursor | Protein Variants | Clinical |
|---|---|---|---|
| AA | Serum Amyloid A Protein (ApoSSA) | | Reactive (secondary) Amyloidosis: Familial Mediterranean fever Familial amyloid nephropathy with urticaria and deafness (Muckle-Wells syndrome) |
| AA | Serum amyloid A protein (ApoSSA) | | Reactive systemic amyloidosis associated with systemic inflammatory diseases |
| AL | Monoclonal immunoglobulin light chains (kappa, lambda) | Ak, A, (e.g., AkIII) | Idiopathic (primary) Amyloidosis: myeloma or macroglobulinemia-associated; systemic amyloidosis associated with immunocyte dyscrasia; monoclonal gammopathy; occult dyscrasia; local nodular amyloidosis associated with chronic inflammatory diseases |
| AH | IgG (1(γ1)) | Aγ1 | Heavy chain amyloidosis associated with several immunocyte dyscrasias |
| ATTR | Transthyretin (TTR) | At least 30 known point mutations | Familial amyloid polyneuropathy (e.g., Met 30, Portuguese) |
| ATTR | Transthyretin (TTR) | e.g., Met 111 | Familial amyloid cardiomyopathy (Danish) |
| ATTR | Transthyretin (TTR) | Wild-type TTR or Ile 122 | Systemic senile amyloidosis |
| AapoAI | ApoAI | Arg 26 | Familial amyloid polyneuropathy |
| Agel | Gelsolin | Asn 187 | Familial amyloidosis (Finnish) |
| Acys | Cystatin C | Gln 68 | Hereditary cerebral hemorrhage with amyloidosis (Icelandic) |
| Aβ | Amyloid β protein precursor (e.g. β-APP$_{695}$) | Various: Gln 618, | Alzheimer's disease Down's syndrome Hereditary cerebral hemorrhage amyloidosis (Dutch) Sporadic cerebral amyloid angiopathy Inclusion body myositis |
| AB$_2$M | Beta$_2$ microglobulin | | Associated with chronic hemodialysis |
| Acal | (Pro)calcitonin | (Pro)calcitonin | Medullary carcinoma of thyroid |
| AANF | Atrial natriuretic factor | | Focal Senile Amyloidoses: Isolated atrial amyloid |
| Aβ SVEP[a] | β-amyloid precursor protein | | Brain Seminal vesicles |
| AB$_2$M | — Beta$_2$ microglobulin Keratin | | Prostate Primary localized cutaneous amyloid (macular, papular) |

TABLE 1-continued

Classification of Amyloid Diseases

| Amyloid Protein/ Peptide | Protein Precursor | Protein Variants | Clinical |
|---|---|---|---|
| PrP | Prion precursor protein (33–35 kDa cellular form) | Scrapie protein 27–30 kDa | Sporadic Creutzfeldt-Jacob Disease Kuru (transmissible spongiform encephalopathies, prion diseases) |
| AIAPP | Islet amyloid polypeptide (IAPP) | | Islets of Langerhans Diabetes type II, Insulinoma |
| Peptide hormones, fragments | e.g., precalcitonin | | Exocrine amyloidosis, associated with APUDomas |

[a]Seminal vesicle exocrine protein

Often, fibrils forming the bulk of an amyloid deposit are derived from one or more primary precursor proteins or peptides, and are usually associated with sulfated glycosaminoglycans. In addition, amyloid deposits may include minor proteins and peptides of various types, along with other components, such as proteoglycans, gangliosides and other sugars, as described in more detail in the sections that follow.

Currently, there are no specific, amyloid-directed treatments for any of the amyloid diseases. Where there is an underlying or associated disease state, therapy is directed towards decreasing the production of amyloidogenic protein by treating the underlying disease. This is exemplified by the treatment of *tuberculosis* with antibiotics, thereby reducing the mycobacterial load, resulting in a reduction of inflammation and in associated reduction of SSA protein. In the case of AL amyloid due to multiple myeloma, chemotherapy is administered to patients, causing a reduction in plasma cells and a lowering of myeloma immunoglobulin levels. As these levels decline, the AL amyloid may clear. Co-owned U.S. patent applications U.S. Ser. No. 09/201,430, filed Nov. 30, 1998 and U.S. Ser. No. 09/322,289, filed May 28, 1999 reveal that amyloid plaque burden associated with Alzheimer's disease can be greatly reduced (and prevented) by administration of agents which produce or confer an immune response directed at β-amyloid peptide (Aβ, and fragments thereof. It is the discovery of the present invention that induction of an immune response to various amyloid plaque components is effective in treating a broad range of amyloid diseases.

SUMMARY OF THE INVENTION

The present invention is directed to pharmaceutical compositions and methods for treating a number of amyloid diseases. According to one aspect, the invention includes pharmaceutical compositions that include, as an active ingredient, an agent that is effective to induce an immune response against an amyloid component in a patient. Such compositions will generally also include excipients and in preferred embodiments may include adjuvants. In further preferred embodiments, the adjuvants include, for example, aluminum hydroxide, aluminum phosphate, MPL™, QS-21 (Stimulon™) or incomplete Freund's adjuvant. According to a related embodiment, such pharmaceutical compositions may include a plurality of agents effective to induce an immune response against more than one amyloid component in the patient.

In a related embodiment, the agent is effective to produce an immune response directed against a fibril peptide or protein amyloid component. Preferably, such a fibril peptide or protein is derived from a fibril precursor protein known to be associated with certain forms of amyloid diseases, as described herein. Such precursor proteins include, but are not limited to, Serum Amyloid A protein (ApoSSA), immunoglobulin light chain, immunoglobulin heavy chain, ApoAI, transthyretin, lysozyme, fibrogen a chain, gelsolin, cystatin C, Amyloid β protein precursor (β-APP), Beta$_2$ microglobulin, prion precursor protein (PrP), atrial natriuretic factor, keratin, islet amyloid polypeptide, a peptide hormone, and synuclein. Such precursors also include mutant proteins, protein fragments and proteolytic peptides of such precursors. In a preferred embodiment, the agent is effective to induce an immune response directed against a neoepitope formed by a fibril protein or peptide, with respect to a fibril precursor protein. That is, as described in more detail herein, many fibril-forming peptides or proteins are fragments of such precursor proteins, such as those listed above. When such fragments are formed, such as by proteolytic cleavage, epitopes may be revealed that are not present on the precursor and are therefore not immunologically available to the immune system when the fragment is a part of the precursor protein. Agents directed to such epitopes may be preferred therapeutic agents, since they may be less likely to induce an autoimmune response in the patient.

According to a related embodiment, pharmaceutical compositions of the invention include agents directed to amyloid components, such as those selected from the group including, but not limited to the following fibril peptides or proteins: AA, AL, ATTIR AApoA1, Alys, Agel, Acys, Aβ, AB$_2$M, AScr, Acal, AIAPP and synuclein-NAC fragment. The full names and compositions of these peptides are described herein. Such peptides can be made according to methods well known in the art, as described herein.

According to a further related embodiment, agents included in such pharmaceutical compositions also include certain to sulfated proteoglycans. In a related embodiment, the proteoglycan is a heparin sulfate glycosaminoglycan, preferably perlecan, dermatan sulfate, chondroitin-4-sulfate, or pentosan polysulfate.

According to another related aspect, the invention includes a method of preventing or treating a disorder characterized by amyloid deposition in a mammalian subject. In accordance with this aspect of the invention, the subject is given a dosage of an agent effective to produce an immune response against an amyloid component characteristic of the amyloid disorder from which the subject suffers. Essentially, the methods include administering pharmaceutical compositions containing immunogenic amyloid components specific to the disorder, such as those described above. Such methods are further characterized by their effectiveness in inducing immunogenic responses in the subject. According to a preferred embodiment, the method is effective to produce an immunological response that is characterized by a serum titer of at least 1:1000 with respect to the amyloid component against which the immunogenic agent is directed. In yet a further preferred embodiment, the serum titer is at least 1:5000 with respect to the fibril component. According to a related embodiment, the immune response is characterized by a serum amount of immunoreactivity corresponding to greater than about four times higher than a serum level of immunoreactivity measured in a pre-treatment control serum sample. This latter characterization is particularly appropriate when serum immunoreactivity is measured by ELISA techniques, but can apply to any relative or absolute measurement of serum immunoreactivity. According to a preferred embodiment, the immunoreactivity is measured at a serum dilution of about 1:100.

According to a still further related aspect, the invention includes a method of determining the prognosis of a patient undergoing treatment for an amyloid disorder. Here, patient serum amount of immunoreactivity against an amyloid component characteristic of the selected disorder is measured, and a patient serum amount of immunoreactivity of at least four times a baseline control level of serum immunoreactivity is indicative of a prognosis of improved status with respect to the particular amyloid disorder. According to preferred embodiments, the amount of immunoreactivity against the selected amyloid component present in the patient serum is characterized by a serum titer of at least about 1:1000, or at least 1:5000, with respect to the amyloid component According to a still related aspect, the invention also includes so-called "passive immunization" methods and pharmaceutical compositions for preventing or treating amyloid diseases. According to this aspect of the invention, patients are given an effective dosage of an antibody that specifically binds to a selected amyloid component, preferably a fibril component present in amyloid deposits characteristic of the disease to be treated. In general, such antibodies are selected for their abilities to specifically bind the various proteins, peptides, and components described with respect to the pharmaceutical compositions and methods described in the preceding paragraphs of this section. According to a related embodiment, such methods and compositions may include combinations of antibodies that bind at least two amyloid fibril components. In general, pharmaceutical compositions are administered to provide a serum amount of immunoreactivity against the target amyloid component that is at least about four times higher than a serum level of immunoreactivity against the component measured in a control serum sample. The antibodies may also be administered with a carrier, as described herein. In general, in accordance with this aspect of the invention, such antibodies, will be administered (or formulated for administration) peritoneally, orally, intranasally, subcutaneously, intramuscularly, topically or intravenously, but can be administered or formulated for administration by any pharmaceutically effective route (i.e., effective to produce the indicated therapeutic levels, as set forth above and herein).

According to a related embodiment, therapeutic antibodies may be administered by administering a polynucleotide encoding at least one antibody chain to the patient. According to this aspect of the invention, the polynucleotide is expressed in the patient to produce the antibody chain in a pharmaceutically effective amount in the patient. Such a polynucleotide may encode heavy and light chains of the antibody, thereby producing the heavy and light chains in the patient.

According to preferred embodiments, the immunization regimens described above may include administration of agents, including antibodies, in multiple dosages, such as over a 6 month period, such as an initial immunization followed by booster injections at time intervals, such as 6 week intervals, according to methods known in the art, or according to patient need, as assessed by immunological response. Alternatively, or in addition, such regiments may include the use of "sustained release" formulations, such as are known in the art.

These and other objects and features of the invention will become more fully apparent when the following detailed description of the invention is read in conjunction with the accompanying drawings.

BRIEF DESCRIPTION OF THE FIGURES

FIGS. 15A–E: Aβ levels in the cortex of 12-month old PDAPP mice treated with AN1792 or AN1528 in combination with different adjuvants. The Aβ level for individual mice in each treatment group, and the median, mean, and p values for each treatment group are shown.

FIG. 15A: The values for mice for the PBS-treated control group and the untreated control group.

FIG. 15B: The values for mice in the AN1528/alum and AN1528/MPL-treatment groups.

FIG. 15C: The values for mice in the AN1528/QS21 and AN1792/Freund's adjuvant treatment groups.

FIG. 15D: The values for mice in the AN1792/Thimerosol and AN1792/alum treatment groups.

FIG. 15E: The values for mice in the AN1792/MPL and AN1792/QS21 treatment groups.

DETAILED DESCRIPTION OF THE INVENTION

A. Definitions

Figure 1:
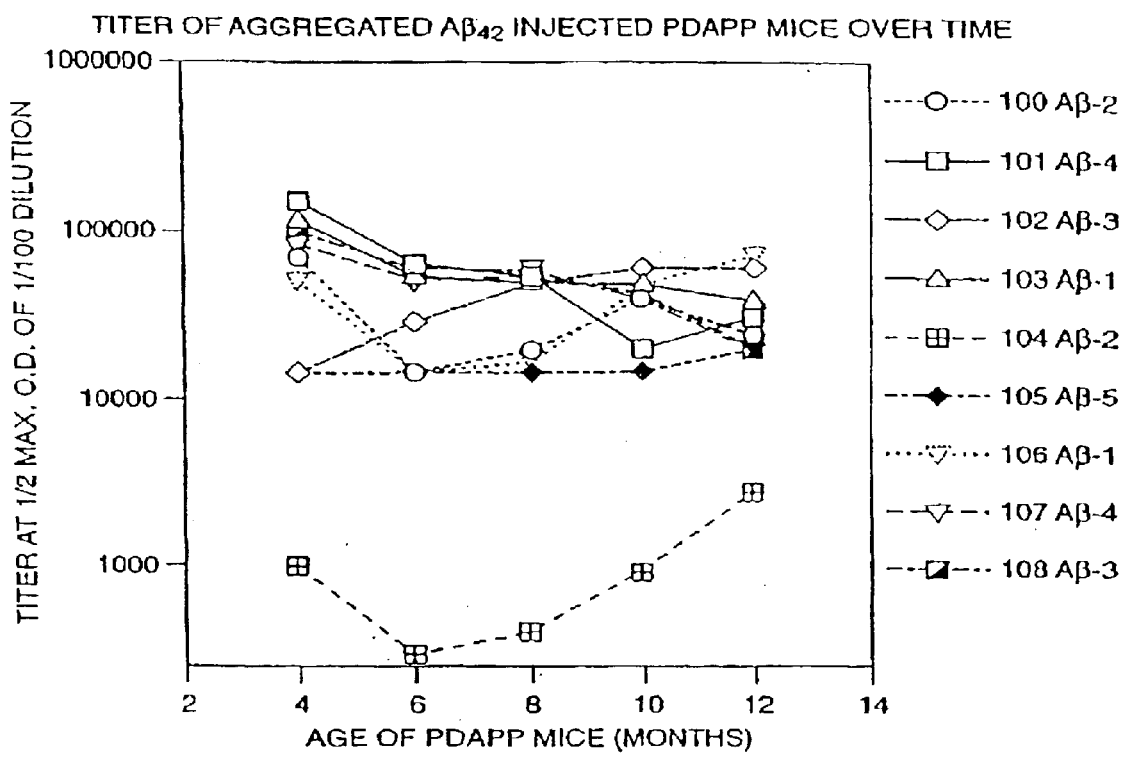
FIG. 1: Antibody titer in transgenic mice after injection with Aβ1–42.

Unless otherwise indicated, all terms used herein have the same meaning as they would to one skilled in the art of the present invention. Practitioners are particularly directed to Sambrook, et al. (1989) Molecular Cloning: A Laboratory Manual (Second Edition), Cold Spring Harbor Press, Plainview, N.Y. and Ausubel, F. M., et al. (1998) Current Protocols in Molecular Biology, John Wiley & Sons, New York, N.Y., for definitions, terms of art and standard methods known in the art of biochemistry and molecular biology. It is understood that this invention is not limited to the particular methodology, protocols, and reagents described, as these may be varied to produce the same result.

The term "adjuvant" refers to a compound that, when administered in conjunction with an antigen, augments the immune response to the antigen, but when administered alone does not generate an immune response to the antigen. Adjuvants can augment an immune response by several mechanisms including lymphocyte recruitment, stimulation of B and/or T cells, and stimulation of macrophages.

"Amyloid disease" or "amyloidosis" refers to any of a number of disorders which have as a symptom or as part of its pathology the accumulation or formation of amyloid plaques.

An "amyloid plaque" is an extracellular deposit composed mainly of proteinaceous fibrils. Generally, the fibrils are composed of a dominant protein or peptide; however, the plaque may also include additional components that are peptide or non-peptide molecules, as described herein.

An "amyloid component" is any molecular entity that is present in an amyloid plaque including antigenic portions of such molecules. Amyloid components include but are not limited to proteins, peptides, proteoglycans, and carbohydrates. A "specific amyloid component" refers to a molecular entity that is found primarily or exclusively in the amyloid plaque of interest.

An "agent" is a chemical molecule of synthetic or biological origin. In the context of the present invention, an agent is generally a molecule that can be used in a pharmaceutical composition.

An "anti-amyloid agent" is an agent which is capable of producing an immune response against an amyloid plaque component in a vertebrate subject, when administered by active or passive immunization techniques.

The terms "polynucleotide" and "nucleic acid," as used interchangeably herein refer to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA) Such bases are typically inosine, adenosine, guanosine, cytosine, uracil and thymidine. Polymeric molecules include double and single stranded RNA and DNA, and backbone modifications thereof, for example, methylphosphonate linkages.

The term "polypeptide" as used herein refers to a compound made up of a single chain of amino acid residues linked by peptide bonds. The term "protein" may be synonymous with the term "polypeptide" or may refer to a complex of two or more polypeptides.

The term "peptide" also refers to a compound composed of amino acid residues linked by peptide bonds. Generally peptides are composed of 100 or fewer amino acids, while polypeptides or proteins have more than 100 amino acids. As used herein, the term "protein fragment" may also be read to mean a peptide.

A "fibril peptide" or "fibril protein" refers to a monomeric or aggregated form of a protein or peptide that forms fibrils present in amyloid plaques. Examples of such peptides and proteins are provided herein.

A "pharmaceutical composition" refers to a chemical or biological composition suitable for administration to a mammalian individual. Such compositions may be specifically formulated for adminstration via one or more of a number of routes, including but not limited to, oral, parenteral, intravenous, intraarterial, subcutaneous, intranasal, sublingual, intraspinal, intracerebroventricular, and the like.

A "pharmaceutical excipient" or a "pharmaceutically acceptable excipient" is a carrier, usually a liquid, in which an active therapeutic agent is formulated. The excipient generally does not provide any pharmacological activity to the formulation, though it may provide chemical and/or biological stability, release characteristcs, and the like. Exemplary formulations can be found, for example, in Remington's Pharmaceutical Sciences, 19th Ed., Grennaro, A., Ed., 1995.

A "glycoprotein" is protein to which at least one carbohydrate chain (oligopolysaccharide) is covalently attached.

A "proteoglycan" is a glycoprotein where at least one of the carbohydrate chains is a glycosaminoglycan, which is a long linear polymer of repeating disaccharides in which one member of the pair usually is a sugar acid (uronic acid) and the other is an amino sugar.

The term "immunological" or "immune" or "immunogenic" response refers to the development of a humoral (antibody mediated) and/or a cellular (mediated by antigen-specific T cells or their secretion products) response directed against an antigen in a vertebrate individual. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by standard proliferation assays (CD4$^+$ T cells) or CTL (cytotoxic T lymphocyte) assays known in the art. The relative contributions of humoral and cellular responses to the protective or therapeutic effect of an immunogen can be distinguished by separately isolating immunoglobulin (IgG) and T-cell fractions from an immunized syngeneic animal and measuring protective or therapeutic effect in a second subject.

An "immunogenic agent" or "immunogen" or "antigen is a molecule that is capable of inducing an immunological response against itself upon administration to a patient, either in conjunction with, or in the absence of, an adjuvant. Such molecules include, for example, amyloid fibril peptides or fragments thereof conjugated to a carrier protein, such keyhole limpet hemocyanin, Cd3 or tetanus toxin.

An "epitope" or "antigenic determinate" is the part of an antigen that binds to the antigen-binding region of an antibody.

The term "A$\beta$," "A$\beta$ peptide" and "Amyloid $\beta$" peptide are synonymous, and refer to one or more peptide compositions of about 38–43 amino acids derived from Beta Amyloid Precursor Protein ($\beta$-APP), as described herein. "A$\beta$xx" refers to amyloid $\beta$ peptide $\beta$-xx, where xx is a number indicating the number of amino acids in the peptide; e.g., A$\beta$42 is the same as A$\beta$1–42, which is also referred to herein as "AN1792," and A1340 is the same as A$\beta$11–40, which is also referred to herein as "AN1578."

Disaggregated or monomeric A$\beta$ means soluble, monomeric peptide units of A$\beta$. One method to prepare monomeric A$\beta$ is to dissolve lyophilized peptide in neat DMSO with sonication. The resulting solution is centrifuged to remove any insoluble particulates. Aggregated A$\beta$ is a mixture of oligomers in which the monomeric units are held together by noncovalent bonds.

The term "naked polynucleotide" refers to a polynucleotide not complexed with colloidal materials. Naked polynucleotides are sometimes cloned in a plasmid vector.

The term "patient" includes human and other mammalian subjects that receive either prophylactic or therapeutic treatment.

The terms "significantly different than," "statistically significant," "significantly higher (or lower) than," and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests kenown in the art). Compositions or methods "comprising" one or more recited elements may include other elements not specifically recited. For example, a composition that comprises a fibril component peptide encompasses both the isolated peptide and the peptide as a component of a larger polypeptide sequence. By way of further example, a composition that comprises elements A and B also encompasses a composition consisting of A, B and C.

B. Amyloid Diseases

1. Overview and Pathogenesis

Amyloid diseases or amyloidoses include a number of disease states having a wide variety of outward symptoms. These disorders have in common the presence of abnormal extracellular deposits of protein fibrils, known as "amyloid deposits" or "amyloid plaques" that are usually about 10–100 $\mu$m in diameter and are localized to specific organs or tissue regions. Such plaques are composed primarily of a naturally occurring soluble protein or peptide. These insoluble deposits are composed of generally lateral aggregates of fibrils that are approximately 10–15 nm in diameter. Amyloid fibrils produce a characteristic apple green birefringence in polarized light, when stained with Congo Red dye. The disorders are classified on the basis of the major fibril components forming the plaque deposits, as discussed below.

The peptides or proteins forming the plaque deposits are often produced from a larger precursor protein. More specifically, the pathogenesis of amyloid fibril deposits generally involves proteolytic cleavage of an "abnormal" precursor protein into fragments. These fragments generally aggregate into anti-parallel $\beta$ pleated sheets; however, certain undegraded forms of precursor protein have been reported to aggregate and form fibrils in familial amyloid polyneuropathy (variant transthyretin fibrils) and dialysis-related amyloidosis ($\beta_2$ microglobulin fibrils) (Tan, et al., 1994, supra).

2. Clinical Syndromes

This section provides descriptions of major types of amyloidoses, including their characteristic plaque fibril compositions. It is a general discovery of the present invention that amyloid diseases can be treated by administering agents that serve to stimulate an immune response against a component or components of the various disease-specific amyloid deposits. As discussed in more detail in Section C below, such components are preferably constituents of the fibrils that form the plaques. The sections below serve to exemplify major forms of amyloidosis and are not intended to limit the invention.

a. AA (Reactive) Amyloidosis

Generally, AA amyloidosis is a manifestation of a number of diseases that provoke a sustained acute phase response. Such diseases include chronic inflammatory disorders, chronic local or systemic microbial infections, and malignant neoplasms.

AA fibrils are generally composed of 8000 dalton fragments (AA peptide or protein) formed by proteolytic cleavage of serum amyloid A protein (apoSSA), a circulating apolipoprotein which is present in HDL particles and which is synthesized in hepatocytes in response to such cytokines as IL-1, IL-6 and TNF. Deposition can be widespread in the body, with a preference for parenchymal organs. The spleen is usually a deposition site, and the kidneys may also be affected. Deposition is also common in the heart and gastrointestinal tract.

AA amyloid diseases include, but are not limited to inflammatory diseases, such as rheumatoid arthritis, juvenile chronic arthritis, ankylosing spondylitis, psoriasis, psoriatic arthropathy, Reiter's syndrome, Adult Still's disease, Behcet's syndrome, and Crohn's disease. AA deposits are also produced as a result of chronic microbial infections, such as leprosy, *tuberculosis*, bronchiectasis, decubitus ulcers, chronic pyelonephritis, osteomyelitis, and Whipple's disease. Certain malignant neoplasms can also result in AA fibril amyloid deposits. These include such conditions as Hodgkin's lymphoma, renal carcinoma, carcinomas of gut, lung and urogenital tract, basal cell carcinoma, and hairy cell leukemia.

b. AL Amyloidoses

AL amyloid deposition is generally associated with almost any dyscrasia of the B lymphocyte lineage, ranging from malignancy of plasma cells (multiple myeloma) to benign monoclonal gammopathy. At times, the presence of amyloid deposits may be a primary indicator of the underlying dyscrasia.

Fibrils of AL amyloid deposits are composed of monoclonal immunoglobulin light chains or fragments thereof.

More specifically, the fragments are derived from the N-terminal region of the light chain (kappa or lambda) and contain all or part of the variable ($V_L$) domain thereof. Deposits generally occur in the mesenchymal tissues, causing peripheral and autonomic neuropathy, carpal tunnel syndrome, macroglossia, restrictive cardiomyopathy, arthropathy of large joints, immune dyscrasias, myelomas, as well as occult dyscrasias. However, it should be noted that almost any tissue, particularly visceral organs such as the heart, may be involved.

c. Hereditary Systemic Amyloidoses

There are many forms of hereditary systemic amyloidoses. Although they are relatively rare conditions, adult onset of symptoms and their inheritance patterns (usually autosomal dominant) lead to persistence of such disorders in the general population. Generally, the syndromes are attributable to point mutations in the precursor protein leading to production of variant amyloidogenic peptides or proteins. Table 2 summarizes the fibril composition of exemplary forms of these disorders.

TABLE 2

Hereditary Amyloidoses[a]

| Fibril Peptide/Protein | Genetic variant | Clinical Syndrome |
| --- | --- | --- |
| Transthyretin and fragments (ATTR) | Met30, many others | Familial amyloid polyneuropathy (FAP), (mainly peripheral nerves) |
| Transthyretin and fragments (ATTR) | Thr45, Ala60, Ser84, Met111, Ile122 | Cardiac involvement predominant without neuropathy |
| N-terminal fragment of Apolipoprotein A1 (apoAI) | Arg 26 | Familial amyloid polyneuropathy (FAP), (mainly peripheral nerves) |
| N-terminal fragment of Apolipoprotein A1 (AapoAI) | Arg26, Arg50, Arg60, others | Ostertag-type, non-neuropathic (predominantly visceral involvement) |
| Lysozyme (Alys) | Thr56, His67 | Ostertag-type, non-neuropathic (predominantly visceral involvement) |
| Fibrogen α chain fragment | Leu554, Val 526 | Ostertag-type, non-neuropathic (predominantly visceral involvement) |
| Gelsolin fragment (Agel) | Asn187, Tyr187 | Cranial neuropathy with lattice corneal dystrophy |
| Cystatin C fragment | Glu68 | Hereditary cerebral hemorrhage (cerebral amyloid angiopathy)-Icelandic type |
| β-amyloid protein (Aβ) derived from Amyloid Precursor Protein (APP) | Gln693 | Hereditary cerebral hemorrhage (cerebral amyloid angiopathy)-Dutch type |
| β-amyloid protein (Aβ) derived from Amyloid Precursor Protein (APP) | Ile717, Phe717, Gly717 | Familial Alzheimer's Disease |
| β-amyloid protein (Aβ) derived from Amyloid Precursor Protein (APP) | Asn670, Leu671 | Familial Dementia-probable Alzheimer's Disease |
| Prion Protein (PrP) derived from PrP precursor protein 51–91 insert | Leu102, Val167, Asn178, Lys200 | Famical Creutzfeldt-Jakob disease; Gerstmann-Sträussler-Scheinker syndrome (hereditary spongiform encephalopathies, prion diseases) |
| AA derived from Serum amyloid A protein (ApoSSA) | | Famical Mediterranean fever, predominant renal involvement (autosomal recessive) |
| AA derived from Serum amyloid A protein (ApoSSA) | | Muckle-Well's syndrome, nephropathy, deafness, urticaria, limb pain |
| Unknown | | Cardiomyopathy with persistent atrial standstill |
| Unknown | | Cutaneous deposits (bullous, papular, pustulodermal) |

[a]Data derived from Tan & Pepys, 1994, supra.

The data provided in Table 2 are exemplary and are not intended to limit the scope of the invention. For example, more than 40 separate point mutations in the transthyretin gene have been described, all of which give rise to clinically similar forms of familial amyloid polyneuropathy.

Transtbyretin (TR) is a 14 kilodalton protein that is also sometimes referred to as prealbumin. It is produced by the liver and choroid plexus, and it functions in transporting thyroid hormuones and vitamin A. At least 50 variant forms of the protein, each characterized by a single amino acid change, are responsible for various forms of familial amyloid polyneuropathy. For example, substitution of proline for leucine at position 55 results in a particularly progressive form of neuropathy; substitution of methionine for leucine at position 111 resulted in a severe cardiopathy in Danish patients. Amyloid deposits isolated from heart tissue of patients with systemic amyloidosis have revealed that the deposits are composed of a heterogeneous mixture of TTR and fragments thereof, collectively referred to as ATTR, the full length sequences of which have been characterized. ATTR fibril components can be extracted from such plaques and their structure and sequence determined according to the methods known in the art (e.g., Gustavsson, A., et al., Laboratory Invest. 73: 703–708, 1995; Kametani, F., et al., Biochem. Biophys. Res. Commun. 125: 622–628, 1984; Pras, M., et al., PNAS 80: 539–42, 1983).

Persons having point mutations in the molecule apolipoprotein AI (e.g., Gly→Arg26; Trp→Arg50; Leu→Arg60) exhibit a form of amyloidosis ("Ostertag type") characterized by deposits of the protein apolipoprotein AI or fragments thereof (AApoAI). These patients have low levels of high density lipoprotein (HDL) and present with a peripheral neuropathy or renal failure.

A mutation in the alpha chain of the enzyme lysozyme (e.g., Ile→Thr56 or Asp→His57) is the basis of another form of Östertag-type non-neuropathic hereditary amyloid reported in English families. Here, fibrils of the mutant lysozyme protein (Alys) are deposited, and patients generally exhibit impaired renal function. This protein, unlike most of the fibril-forming proteins described herein, is usually present in whole (unfragmented) form (Benson, M. D., et al. CIBA Fdn. Symp. 199:104–131, 1996).

β-amyloid peptide (Aβ) is a 39–43 amino acid peptide derived by proteolysis from a large protein known as beta amyloid precursor protein (βAPP). Mutations in βAPP result in familial forms of Alzheimer's disease, Down's syndrome and/or senile dementia, characterized by cerebral deposition of plaques composed of Aβ fibrils and other components, which are described in further detail below. Known mutations in APP associated with Alzheimer's disease occur proximate to the cleavage sites of β or γ secretase, or within Aβ. For example, position 717 is proximate to the site of γ-secretase cleavage of APP in its processing to Aβ, and positions 670/671 are proximate to the site of β-secretase cleavage. Mutations at any of these residues may result in Alzheimer's disease, presumably by causing an increase the amount of the 42/43 amino acid form of Aβ generated from APP. The structure and sequence of Aβ peptides of various lengths are well known in the art. Such peptides can be made according to methods known in the art (e.g., Glenner and Wong, Biochem Biophys. Res. Comm. 129: 885–890, 1984; Glenner and Wong, Biochem Biophys. Res. Comm. 122:1131–1135, 1984). In addition, various forms of the peptides are commercially available.

Synuclein is a synapse-associated protein that resembles an alipoprotein and is abundant in neuronal cytosol and presynaptic terminals. A peptide fragment derived from α-synuclein, termed NAC, is also a component of amyloid plaques of Alzheimer's disease. (Clayton, et al., 1998). This component also serves as a target for immunologically-based treatments of the present invention, as detailed below.

Gelsolin is a calcium binding protein that binds to and-fragments actin filaments. Mutations at position 187 (e.g., Asp→Asn; Asp→Tyr) of the protein result in a form of hereditary systemic amyloidosis, usually found in patients from Finland, as well as persons of Dutch or Japanese origin. In afflicted individuals, fibrils formed from gelsolin fragments (Agel), usually consist of amino acids 173–243 (68 kDa carboxyterminal fragment) and are deposited in blood vessels and basement membranes, resulting in corneal dystrophy and cranial neuropathy which progresses to peripheral neuropathy, dystrophic skin changes and deposition in other organs. (Kangas, H., et al Human Mol. Genet. 5(9): 1237–1243, 1996).

Other mutated proteins, such as mutant alpha chain of fibrinogen (AfibA) and mutant cystatin C (Acys) also form fibrils and produce characteristic hereditary disorders. AfibA fibrils form deposits characteristic of a nonneuropathic hereditary amyloid with renal disease; Acys deposits are characteristic of a hereditary cerebral amyloid angiopathy reported in Iceland. (Isselbacher, et al., Harrison's Principles of Internal Medicine, McGraw-Hill, San Francisco, 1995; Benson, et al., supra.). In at least some cases, patients with cerebral amyloid angiopathy (CAA) have been shown to have amyloid fibrils containing a non-mutant form of cystatin C in conjunction with beta protein. (Nagai, A., et al. Molec. Chem. Neuropathol. 33: 63–78, 1998).

Certain forms of prion disease are now considered to be heritable, accounting for up to 15% of cases, which were previously thought to be predominantly infectious in nature. (Baldwin, et al., in *Research Advances in Alzheimer's Disease and Related Disorders*, John Wiley and Sons, New York, 1995). In such prion disorders, patients develop plaques composed of abnormal isoforms of the normal prion protein ($PrP^c$). A predominant mutant isoform, $PrP^{Sc-}$, also referred to as AScr, differs from the normal cellular protein in its resistance to protease degradation, insolubility after detergent extraction, deposition in secondary lysosomes, post-translational synthesis, and high β-pleated sheet content. Genetic linkage has been established for at least five mutations resulting in Creutzfeldt-Jacob disease (CJD), Gerstmann-Sträussler-Scheinker syndrome (GSS), and fatal familial insomnia (FFI). (Baldwin) Methods for extracting fibril peptides from scrapie fibrils, determining sequences and making such peptides are known in the art. (e.g., Beekes, M., et al. J. Gen. Virol. 76: 2567–76, 1995).

For example, one form of GSS has been linked to a PrP mutation at codon 102, while telencephalic GSS segregates with a mutation at codon 117. Mutations at codons 198 and 217 result in a form of GSS in which neuritic plaques characteristic of Alzheimer's disease contain PrP instead of Aβ peptide. Certain forms of familial CJD have been associated with mutations at codons 200 and 210; mutations at codons 129 and 178 have been found in both familial CJD and FFI. (Baldwin, supra).

d. Senile Systemic Amyloidosis

Amyloid deposition, either systemic or focal, increases with age. For example, fibrils of wild type transthyretin (TIR) are commonly found in the heart tissue of elderly individuals. These may be asymptomatic, clinically silent, or may result in heart failure. Asymptomatic fibrillar focal deposits may also occur in the brain (Aβ), corpora amylacea of the prostate ($Aβ_2$ microglobulin), joints and seminal vesicles.

e. Cerebral Amyloidosis

Local deposition of amyloid is common in the brain, particularly in elderly individuals. The most frequent type of amyloid in the brain is composed primarily of Aβ peptide fibrils, resulting in dementia or sporadic (non-hereditary) Alzheimer's disease. In fact, the incidence of sporadic Alzheimer's disease greatly exceeds forms shown to be hereditary. Fibril peptides forming these plaques are very similar to those described above, with reference to hereditary forms of Alzheimer's disease (AD).

f. Dialysis-related Amyloidosis

Plaques composed of 2 microglobulin ($Aβ_2M$) fibrils commonly develop in patients receiving long term hemodialysis or peritoneal dialysis. $β_2$ microglobulin is a 11.8 kilodalton polypeptide and is the light chain of Class I MHC antigens, which are present on all nucleated cells. Under normal circumstances, it is continuously shed from cell membranes and is normally filtered by the kidney. Failure of clearance, such as in the case of impaired renal function, leads to deposition in the kidney and other sites (primarily in collagen-rich tissues of the joints). Unlike other fibril proteins, $Aβ_2M$ molecules are generally present in unfragmented form in the fibrils. (Benson, supra).

g. Hormone-derived Amyloidoses

Endocrine organs may harbor amyloid deposits, particularly in aged individuals. Hormone-secreting tumors may also contain hormone-derived amyloid plaques, the fibrils of which are made up of polypeptide hormones such as calcitonin (medullary carcinoma of the thyroid), islet amyloid polypeptide (amylin; occurring in most patients with Type II diabetes), and atrial natriuretic peptide (isolated atrial amyloidosis). Sequences and structures of these proteins are well known in the art.

h. Miscellaneous Amyloidoses

There are a variety of other forms of amyloid disease that are normally manifest as localized deposits of amyloid. In general, these diseases are probably the result of the localized production and/or lack of catabolism of specific fibril precursors or a predisposition of a particular tissue (such as the joint) for fibril deposition. Examples of such idiopathic deposition include nodular AL amyloid, cutaneous amyloid, endocrine amyloid, and tumor-related amyloid.

C. Pharmaceutical Compositions

It is the discovery of the present invention that compositions capable of eliciting or providing an immune response directed to certain components of amyloid plaques are effective to treat or prevent development of amyloid diseases. In particular, according to the invention provided herein, it is possible to prevent progression of, ameliorate the symptoms of, and/or reduce amyloid plaque burden in afflicted individuals, when an immunostimulatory dose of an anti-amyloid agent, or corresponding anti-amyloid immune reagent, is administered to the patient. This section describes exemplary anti-amyloid agents that produce active, as well as passive, immune responses to amyloid plaques and provides exemplary data showing the effect treatment using such compositions on amyloid plaque burden.

Generally, anti-amyloid agents of the invention are composed of a specific plaque component, preferably a fibril forming component, which is usually a characteristic protein, peptide, or fragment thereof, as described in the previous section and exemplified below. More generally, therapeutic agents for use in the present invention produce or induce an immune response against a plaque, or more specifically, a fibril component thereof. Such agents therefore include, but are not limited to, the component itself and variants thereof, analogs and mimetics of the component that induce and/or cross-react with antibodies to the component, as well as antibodies or T-cells that are specifically reactive with the amyloid component. According to an important feature, pharmaceutical compositions are not selected from non-specific components—that is, from those components that are generally circulating or that are ubiquitous throughout the body. By way of example, Serum Amyloid Protein (SAP) is a circulating plasma glycoprotein that is produced in the liver and binds to most known forms of amyloid deposits. Therapeutic compositions are preferably directed to this component.

Induction of an immune response can be active, as when an immunogen is administered to induce antibodies or T-cells reactive with the component in a patient, or passive, as when an antibody is administered that itself binds to the amyloid component in the patient. Exemplary agents for inducing or producing an immune response against amyloid plaques are described in the sections below.

Pharmaceutical compositions of the present invention may include, in addition to the immunogenic agent(s), an effective amount of an adjuvant and/or an excipient. Pharmaceutically effective an useful adjuvants and excipients are well known in the art, and are described in more detail in the Sections that follow.

1. Immunostimulatory Agents (Active Immune Response)
a. Anti-fibril Compositions One general class of preferred anti-amyloid agents consists of agents that are derived from amyloid fibril proteins. As mentioned above, the hallmark of amyloid diseases is the deposition in an organ or organ of amyloid plaques consisting mainly of fibrils, which, in turn, are composed of characteristic fibril proteins or peptides. According to the present invention, such a fibril protein or peptide component is a useful agent for inducing an anti-amyloid immune response.

Tables 1 and 2 summarize exemplary fibril-forming proteins that are characteristic of various amyloid diseases. In accordance with this aspect of the present invention, administration to an afflicted or susceptible individual of an immunostimulatory composition which includes the appropriate fibril protein or peptide, including homologs or fragments thereof, provides therapeutic or prophylaxis with respect to the amyloid disease.

By way of example, A$\beta$, also known as $\beta$-amyloid peptide, or A4 peptide (see U.S. Pat. No. 4,666,829; Glenner & Wong, Biochem. Biophys. Res. Commun. 120, 1131 (1984)), is a peptide of 39–43 amino acids, which is the principal component of characteristic plaques of Alzheimer's disease. A$\beta$ is generated by processing of a larger protein APP by two enzymes, termed $\beta$ and gamma secretases (see Hardy, TINS 20, 154 (1997)).

Figure 2:
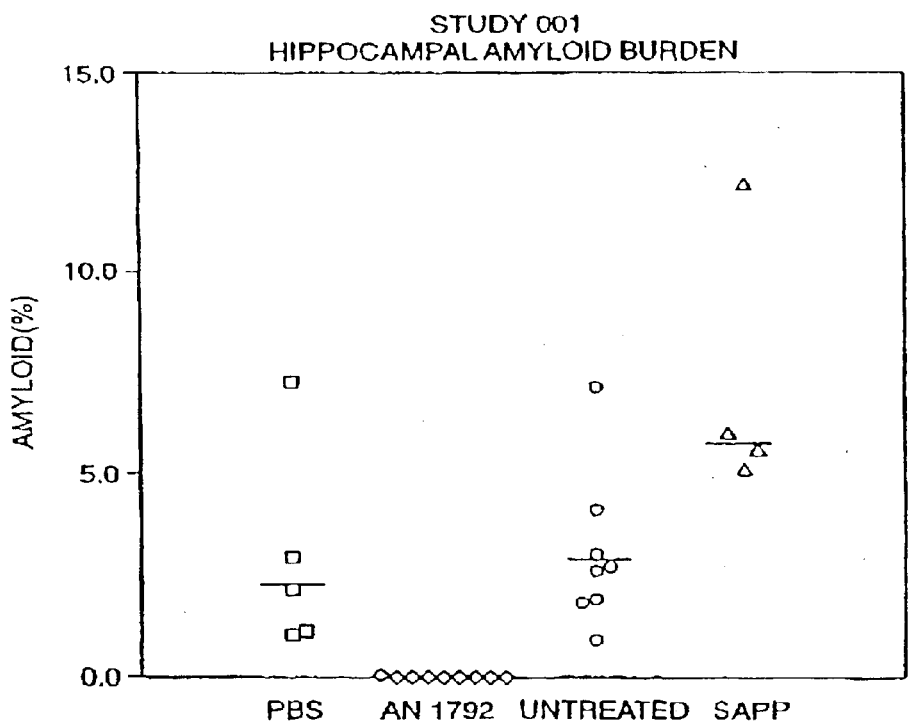
FIG. 2: Amyloid burden in the hippocampus. The percentage of the area of the hippocampal region occupied by amyloid plaques, defined by reactivity with the Aβ-specific monoclonal antibody 3D6, was determined by computer-assisted quantitative image analysis of immunoreacted brain sections. The values for individual mice are shown sorted by treatment group. The horizontal line for each grouping indicates the median value of the distribution.
Figure 3:
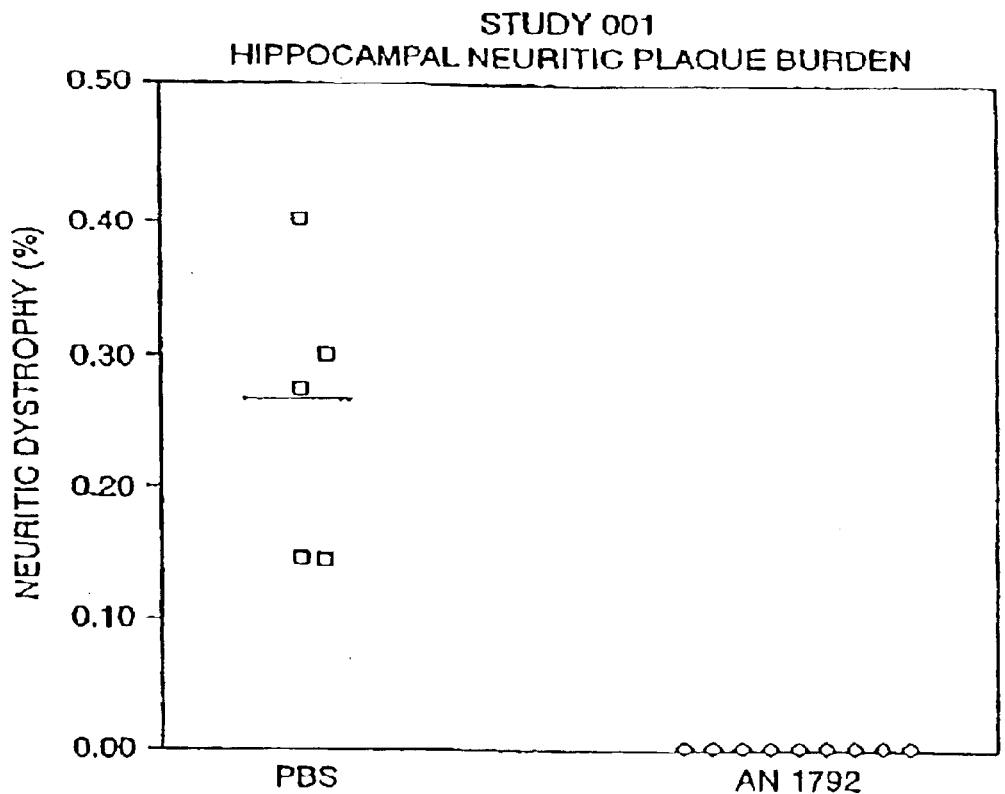
FIG. 3: Neuritic dystrophy in the hippocampus. The percentage of the area of the hippocampal region occupied by dystrophic neurites, defined by their reactivity with the human APP-specific monoclonal 8E5, was determined by quantitative computer-assisted image analysis of immunoreacted brain sections. The values for individual mice are shown for the AN1792-treated group and the PBS-treated control group. The horizontal line for each grouping indicates the median value of the distribution.

Example I describes the results of experiments carried out in support of the present invention, in which A$\beta$42 peptide was administered to heterozygote transgenic mice that overexpress human APP with a mutation at position 717. These mice, known as "PDAPP mice" exhibit Alzheimer's-like pathology and are considered to be an animal model for Alzheimer's disease (Games, et al., Nature 373: 523–7, 1995). As detailed in the Example, these mice exhibit detectable A$\beta$ plaque neuropathology in their brains beginning at about 6 months of age, with plaque deposition progressing over time. In the experiments described herein, aggregated A$\beta$42 (AN1792) was administered to the mice. Most of the treated mice (7/9) had no detectable amyloid in their brains at 13 months of age, in contrast to control mice (saline-injected or untreated), all of which showed significant brain amyloid burden at this age (FIG. 2). These differences were even more pronounced in the hippocampus (FIG. 3). Treated mice also exhibited significant serum antibody titers against A$\beta$ (all greater than 1:1000, 8/9 greater than 1/10,000; FIG. 1, Table 3A). Generally, saline-treated mice exhibited less than 4–5 times background levels of antibodies against A$\beta$ at a dilution of 1:100 at all times tested, and were therefore deemed to have no significant response relative to control (Table 3B). These studies demonstrated that injection with the specific fibril forming peptide A$\beta$ provides protection against deposition of A$\beta$ amyloid plaques.

Serum Amyloid Protein (SAP), is a circulating plasma glycoprotein that is produced in the liver and binds in a calcium-dependent manner to all forms of amyloid fibril, including fibrils of cerebral amyloid plaques in Alzheimer's disease. As part of the foregoing experiments, a group of mice was injected with SAP; these mice developed significant serum titers to SAP (1:1000–1:30000), but did not develop detectable serum titers to A$\beta$ peptide and developed cerebral plaque neuropathology (FIG. 2).

Figure 5:
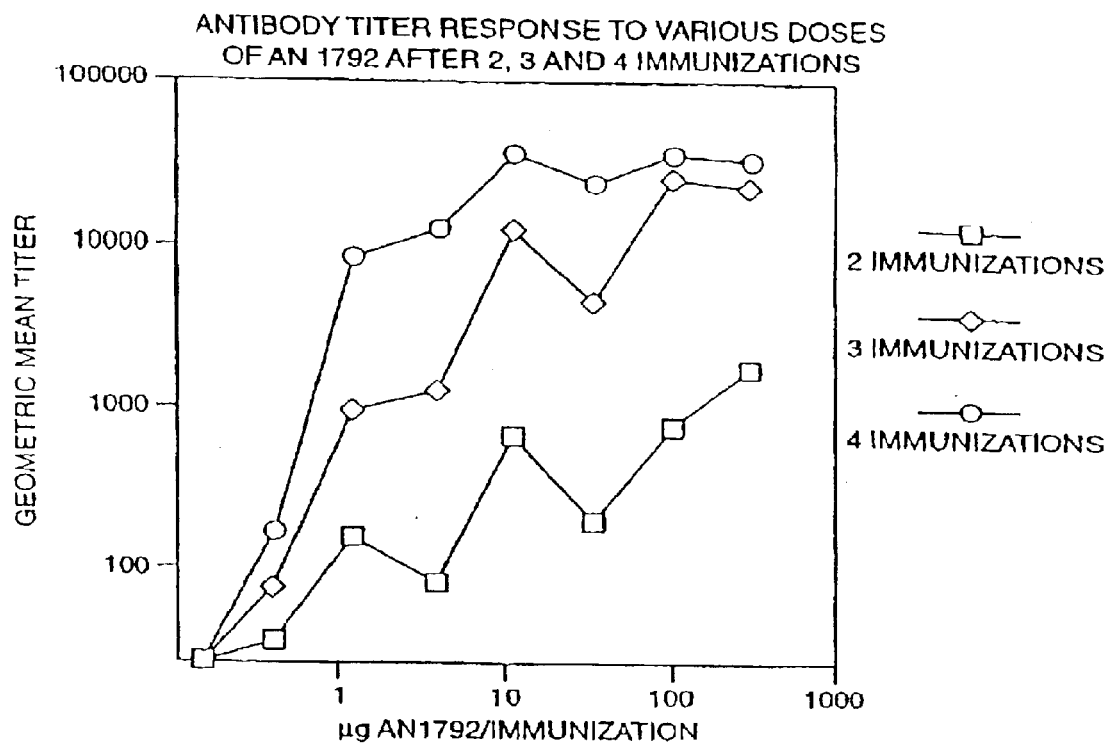
FIG. 5. Geometric mean antibody titers to Aβ42 following immunization with a range of eight doses of Aβ42 ("AN1792") containing 0.14, 0.4, 1.2, 3.7, 11, 33, 100, or 300 µg.

Further experiments, detailed in Example II, demonstrate dose dependence of the immunogenic effect of A$\beta$ injections in mice treated between 5 weeks and about 8 months of age. In these mice, mean serum titers of anti-A$\beta$ peptide antibodies increased with the number of immunizations and with increasing dosages; however, after four immunizations, serum titers measured five days following the immunization leveled off over the higher doses (1–300 $\mu$g) at levels around 1:10000 (FIG. 5).

Figure 7:
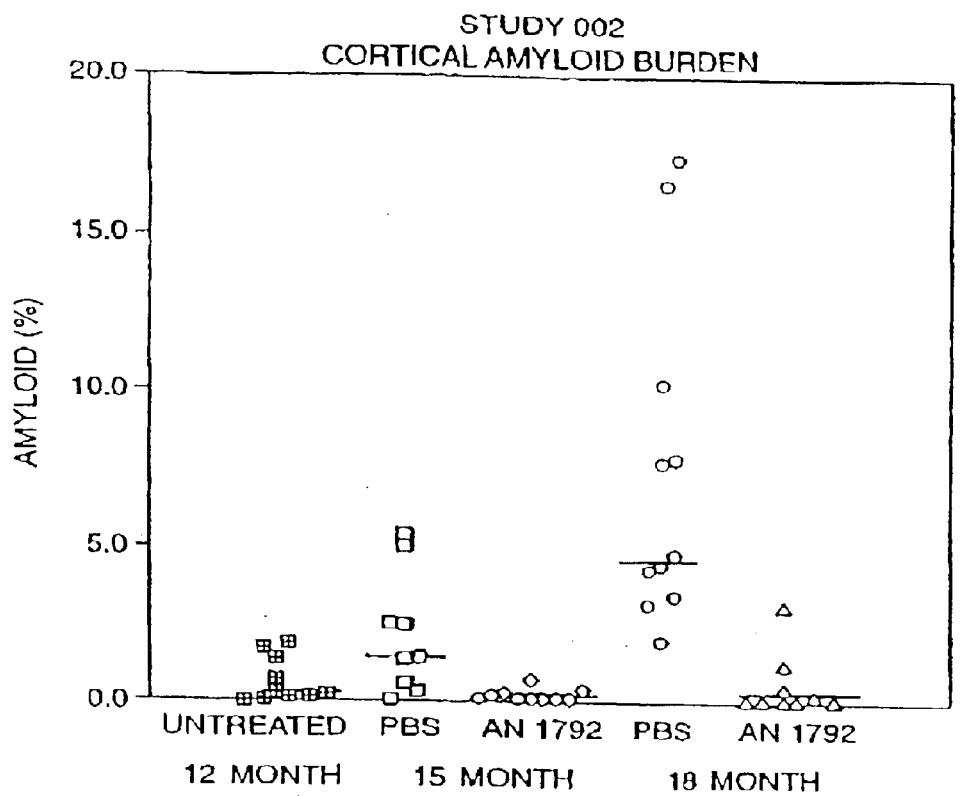
FIG. 7: Quantitative image analysis of the cortical amyloid burden in PBS-and AN1792-treated mice.

Additional experiments in support of the present invention are described in Example III, in which PDAPP model mice were treated with A$\beta$42 commencing at a time point (about 11-months of age) after amyloid plaques were already present in their brains. In these studies, the animals were immunized with A$\beta$42 or saline, and were sacrificed for amyloid burden testing at age 15 or 18 months. As illustrated in FIG. 7, at 18 months of age, A$\beta$42-treated mice exhibited a significantly lower mean amyloid plaque burden (plaque burden, 0.01%) than either PBS-treated 18-month old controls (plaque burden, 4.7%) or 12 month untreated animals (0.28%), where plaque burden is measured by image analysis, as detailed in Example XIII, part 8. These experiments demonstrate the efficacy of the treatment methods of the present invention in reducing existing plaque burden and preventing progression of plaque burden in diseased individuals.

According to this aspect of the invention, therapeutic agents are derived from fibril peptides or proteins which comprise the plaques that are characteristic of the disease of interest. Alternatively, such agents are antigenically similar enough to such components to induce an immune response that also cross-reacts with the fibril component. Tables 1 and 2 provide examples of such fibril peptides and proteins, the compositions and sequences of which are known in the art or can be easily determined according to methods known in the art. (See references cited below and in Section B2 for references that specifically teach methods for extraction and/or compositions of various fibril peptide components; further exemplary fibril components are described below.) Thus, in accordance with the present invention, where a diagnosis of an amyloid disease is made, based on clinical and/or biopsy determinations, the skilled practitioner will be able to ascertain the fibril composition of the amyloid deposits and provide an agent that induces an immune response directed to the fibrillar peptides or proteins.

By way of example, as described above, the therapeutic agent used in treating Alzheimer's disease or other amyloid diseases characterized by Aβ fibril deposition can be any of the naturally occurring forms of Aβ peptide, and particularly the human forms (i.e., Aβ39, Aβ40, Aβ41, Aβ42 or Aβ43). The sequences of these peptides and their relationship to the APP precursor are known in the art and are well known in the art (e.g., Hardy et al., TINS 20, 155–158 (1997)). For example, Aβ42 has the sequence:

H2N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Gly-Leu-Met-Val-Gly-Gly-Val-Val-Ile-Ala-OH. (SEQ ID NO: 34).

Aβ41, Aβ40 and Aβ39 differ from Aβ42 by the omission of Ala, Ala-Ile, and Ala-Ile-Val respectively from the C-terminal end of the peptide. Aβ43 differs from Aβ42 by the presence of a threonine residue at the C-terminus. According to a preferred embodiment of the invention, therapeutic agents will induce an immune response against all or a portion of the fibril component of the disease of interest. For example, a preferred Aβ immunogenic composition is an agent that induces an antibody specific to the free N-terminus of Aβ. Such a composition has the advantage that it would not recognize the precursor protein, β-APP, thereby rendering it less likely to produce autoimmunity.

By way of further example, it is appreciated that patients afflicted with diseases characterized by the deposition of AA fibrils, for example, certain chronic inflammatory disorders, chronic local or systemic microbial infections, and malignant neoplasms, as described above, can be treated with AA peptide, a known 8 kilodalton fragment of serum amyloid A protein (ApoSSA). Exemplary AA amyloid disorders include, but are not limited to inflammatory diseases such as rheumatoid arthritis, juvenile chronic arthritis, anklylosing spondylitis, psoriasis, psoriatic arthropathy, Reiter's syndrome, Adult Still's disease, Behget's syndrome, Crohn's disease, chronic microbial infections such as leprosy, *tuberculosis*, bronchiectasis, decubitus ulcers, chronic pyelonephritis, osteomyelitis, and Whipple's disease, as well as malignant neoplasms such as Hodgkin's lymphoma, renal carcinoma, carcinomas of gut, lung and urogenital tract, basal cell carcinoma, and hairy cell leukemia.

AA peptide refers to one or more of a heterogeneous group of peptides derived from the N-terminus of precursor protein serum amyloid A (ApoSSA), commencing at residue 1, 2 or 3 of the precursor protein and ending at any point between residues 58 and 84; commonly AA fibrils are composed of residues 1–76 of ApoSSA. Precise structures and compositions can be determined, and appropriate peptides synthesized according to methods well known in the art (Lieprieks, J. J., et al. Biochem. Biophys Acta 1270: 81–86, 1995).

By way of further example, fragments derived from the N-terminal region which contain all or part of the variable ($V_L$) domain of immunoglobulin light chains (kappa or lambda chain) generally comprise amyloid deposits in mesenchymal tissues, causing peripheral and autonomic neuropathy, carpal tunnel syndrome, macroglossia, restrictive cardiomyopathy, arthropathy of large joints, immune dyscrasias, myelomas, as well as occult dyscrasias. Compositions of the invention will preferably induce an immune response against a portion of the light chain, preferably against a "neoepitope"—an epitope that is formed as a result of fragmentation of the parent molecule—to reduce possible autoimmune effects.

Various hereditary amyloid diseases are also amenable to the treatment methods of the present invention. Such diseases are described in Section B.2, above. For example, various forms of familial amyloid polyneuropathy are the result of at least fifty mutant forms of transthyretin (TTR), a 14 kilodalton protein produced by the liver, each characterized by a single amino acid change. While many of these forms of this disesase are distinguishable on the basis of their particular pathologies and/or demographic origins, it is appreciated that therapeutic compositions may also be composed of agents that induce an immune response against more than one form of TTR, such as a mixture of two or more forms of ATTR, including wildtype TTR, to provide a generally useful therapeutic composition.

AapoAI-containing amyloid deposits are found in persons having point mutations in the molecule apolipoprotein AI. Patients with this form of disease generally present with peripheral neuropathy or renal failure. According to the present invention, therapeutic compositions are made up one or more of the various forms of AapoAI described herein or known in the art.

Certain familial forms of Alzheimer's disease, as well as Down's syndrome, are the result of mutations in beta amyloid precursor protein, resulting in deposition of plaques having fibrils composed mainly of β-amyloid peptide (Aβ). The use of Aβ peptide in therapeutic compositions of the present invention is described above and exemplified herein.

Other formulations for treating hereditary forms of amyloidosis, discussed above, include compositions that produce immune responses against gelsolin fragments for treatment of hereditary systeric amyloidosis, mutant lysozyme protein (Alys), for treatment of a hereditary neuropathy, mutant alpha chain of fibrinogen (AfibA) for a non-neuropathic form of amyloidosis manifest as renal disease, mutant cystatin C (Acys) for treatment of a form of hereditary cerebral angiopathy reported in Iceland. In addition, certain hereditary forms of prion disease (e.g., Creutzfeldt-Jacob disease (CJD), Gerstmann-Sträussler-Scheinker syndrome (GSS), and fatal familial insomnia (FFI)) are characterized by a mutant isoform of prion protein, $PrP^{Sc}$. This protein can be used in therapeutic compositions for treatment and prevention of deposition of PrP plaques, in accordance with the present invention.

As discussed above, amyloid deposition, either systemic or focal, is also associated with aging. It is a further aspect of the present invention that such deposition can be prevented or treated by administering to susceptible individuals compositions consisting of one or more proteins associated with such aging. Thus, plaques composed of ATTR derived from wild type TTR are frequently found in heart tissue of the elderly. Similarly, certain elderly individuals may develop asymptomatic fibrillar focal deposits of Aβ in their brains; Aβ peptide treatment, as detailed herein may be warranted in such individuals. $β_2$ microglobulin is a frequent component of corpora amylacea of the prostate, and is therefore a further candidate agent in accordance with the present invention.

By way of further example, but not limitation, there are a number of additional, non-hereditary forms amyloid disease that are candidates for treatment methods of the present invention. $\beta_2$ microglobulin fibrillar plaques commonly develop in patients receiving long term hemodialysis or peritoneal dialysis. Such patients may be treated by treatment with therapeutic compositions directed to $\beta_2$ microglobulin or, more preferably, immunogenic epitopes thereof, in accordance with the present invention.

Hormone-secreting tumors may also contain hormone-derived amyloid plaques, the composition of which are generally characteristic of the particular endocrine organ affected. Thus such fibrils may be made up of polypeptide hormones such as calcitonin (medullary carcinoma of the thyroid), islet amyloid polypeptide (occurring in most patients with Type II diabetes), and atrial natriuretic peptide (isolated atrial amyloidosis). Compositions directed at amyloid deposits which form in the aortic intima in atherosclerosis are also contemplated by the present invention. For example, Westermark, et al. describe a 69 amino acid N-terminal fragment of Apolipoprotein A which forms such plaques (Westermark, et al. Am. J. Path. 147:1186–92, 1995); therapeutic compositions of the present invention include immunological reagents directed to such a fragment, as well as the fragment itself.

The foregoing discussion has focused on amyloid fibril components that may be used as therapeutic agents in treating or preventing various forms of amyloid disease. The therapeutic agent can also be an active fragment or analog of a naturally occurring or mutant fibril peptide or protein that contains an epitope that induces a similar protective or therapeutic immune response on administration to a human. Immunogenic fragments typically have a sequence of at least 3, 5, 6, 10 or 20 contiguous amino acids from a natural peptide. Exemplary A$\beta$ peptide immunogenic fragments include A$\beta$1–5, 1–6, 1–7, 1–10, 3–7, 1–3, 1–4, 1–12, 13–28, 17–28, 1–28, 25–35, 35–40 and 35–42. Fragments lacking at least one, and sometimes at least 5 or 10 C-terminal amino acid present in a naturally occurring forms of the fibril component are used in some methods For example, a fragment lacking 5 amino acids from the C-terminal end of A$\beta$43 includes the first 38 amino acids from the N-terminal end of AB. Fragments from the N-terminal half of A$\beta$ are preferred in some methods. Analogs include allelic, species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are $\alpha,\alpha$-disubstituted amino acids, N-alkyl amino acids, lactic acid, 4-hydroxyproline, $\gamma$-carboxyglutamate, $\gamma$-N,N,N-trimethyllysine, $\gamma$-N-acetyllysine, O-phosphoserine, N-acetylserine, N-formylmethionine, 3-methylhistidine, 5-hydroxylysine, $\omega$-N-methylarginine.

Generally, persons skilled in the art will appreciate that fragments and analogs designed in accordance with this aspect of the invention can be screened for cross-reactivity with the naturally occurring fibril components and/or prophylactic or therapeutic efficacy in transgenic animal models as described below. Such fragments or analogs may be used in therapeutic compositions of the present invention, if their immunoreactivity and animal model efficacy is roughly equivalent to or greater than the corresponding parameters measured for the amyloid fibril components.

Such peptides, proteins, or fragments, analogs and other amyloidogenic peptides can be synthesized by solid phase peptide synthesis or recombinant expression, according to standard methods well known in the art, or can be obtained from natural sources. Exemplary fibril compositions, methods of extraction of fibrils, sequences of fibril peptide or protein components are provided by many of the references cited in conjunction with the descriptions of the specific fibril components provided herein. Additionally, other compositions, methods of extracting and determining sequences are known in the art available to persons desiring to make and use such compositions. Automatic peptide synthesizers may be used to make such compositions and are commercially available from numerous manufacturers, such as Applied Biosystems (Perkin Elmer; Foster City, Calif.), and procedures for preparing synthetic peptides are known in the art. Recombinant expression can be in bacteria, such as *E. coli*, yeast, insect cells or mammalian cells; alternatively, proteins can be produced using cell free in vitro translation systems known in the art. Procedures for recombinant expression are described by Sambrook et al., *Molecular Cloning: A Laboratory Manual* (C.S.H.P. Press, NY 2d ed., 1989). Certain peptides and proteins are also available commercially; for example, some forms of A$\beta$ peptide are available from suppliers such as American Peptides Company, Inc., Sunnyvale, Calif., and California Peptide Research, Inc. Napa, Calif.

Therapeutic agents may also be composed of longer polypeptides that include, for example, the active peptide fibril fragment or analog, together with other amino acids. For example, A$\beta$ peptide can be present as intact APP protein or a segment thereof, such as the C-100 fragment that begins at the N-terminus of A$\beta$ and continues to the end of APP. Such polypeptides can be screened for prophylactic or therapeutic efficacy in animal models as described below. The A$\beta$ peptide, analog, active fragment or other polypeptide can be administered in associated form (i.e., as an amyloid peptide) or in dissociated form. Therapeutic agents may also include multimers of monomeric immunogenic agents or conjugates or carrier proteins, and/or, as mentioned above, may be added to other fibril components, in order to provide a broader range of anti-amyloid plaque activity.

In a further variation, an immunogenic peptide, such as a fragment of A$\beta$, can be presented by a virus or a bacteria as part of an immunogenic composition. A nucleic acid encoding the immunogenic peptide is incorporated into a genome or episome of the virus or bacteria. Optionally, the nucleic acid is incorporated in such a manner that the immunogenic peptide is expressed as a secreted protein or as a fusion protein with an outer surface protein of a virus or a transmembrane protein of a bacteria so that the peptide is displayed. Viruses or bacteria used in such methods should be nonpathogenic or attenuated. Suitable viruses include adenovirus, HSV, Venezuelan equine encephalitis virus and other alpha viruses, vesicular stomatitis virus, and other rhabdo viruses, vaccinia and fowl pox. Suitable bacteria include Salmonella and Shigella. Fusion of an immunogenic peptide to HBsAg of HBV is particularly suitable. Therapeutic agents also include peptides and other compounds that do not necessarily have a significant amino acid sequence similarity with A$\beta$ but nevertheless serve as mimetics of A$\beta$ and induce a similar immune response. For example, any peptides and proteins forming $\beta$-pleated sheets can be screened for suitability. Anti-idiotypic antibodies against monoclonal antibodies to A$\beta$ or other amyloidogenic peptides can also be used. Such anti-Id antibodies mimic the antigen and generate an immune response to it (see *Essential Immunology* (Roit ed., Blackwell Scientific Publications, Palo Alto, 6th ed.), p. 181). Agents other than A$\beta$ peptides should induce an immunogenic response against one or more of the preferred segments of Aβ listed above (e.g., 1–10, 1–7, 1–3, and 3–7). Preferably, such agents induce an immunogenic response that is specifically directed to one of these segments without being directed to other segments of Aβ.

Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbanates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980.

Combinatorial libraries and other compounds are initially screened for suitability by determining their capacity to bind to antibodies or lymphocytes (B or T) known to be specific for Aβ or other amyloidogenic peptides such as ATTR. For example, initial screens can be performed with any polyclonal sera or monoclonal antibody to Aβ or any other amyloidogenic peptide of interest. Compounds identified by such screens are then further analyzed for capacity to induce antibodies or reactive lymphocytes to Aβ or other amyloidogenic peptide. For example, multiple dilutions of sera can be tested on microtiter plates that have been precoated with fibril peptide, and a standard ELISA can be performed to test for reactive antibodies to Aβ. Compounds can then be tested for prophylactic and therapeutic efficacy in transgenic animals predisposed to an amyloidogenic disease, as described in the Examples. Such animals include, for example, mice bearing a 717-mutation of APP described by Games et al., supra, and mice bearing a 670/671 Swedish mutation of APP such as described by McConlogue et al., U.S. Pat. No. 5,612,486 and Hsiao et al., Science 274, 99 (1996); Staufenbiel et al., Proc. Natl. Acad. Sci. USA 94, 13287–13292 (1997); Sturchier-Pierrat et al., Proc. Natl. Acad. Sci. USA 94, 13287–13292 (1997); Borchelt et al., Neuron 19, 939–945 (1997)). The same screening approach can be used on other potential agents such as fragments of Aβ, analogs of Aβ and longer peptides including Aβ, described above.

b. Other Plaque Components

It is appreciated that immunological responses directed at other amyloid plaque components can also be effective in preventing, retarding or reducing plaque deposition in amyloid diseases. Such components may be minor components of fibrils or associated with fibrils or fibril formation in the plaques, with the caveat that components that are ubiquitous throughout the body, or relatively non-specific to the amyloid deposit, are generally less suitable for use as therapeutic targets.

It is therefore a further discovery of the present invention that agents that induce an immune response to specific plaque components are useful in treating or preventing progression of amyloid diseases. This section provides background on several exemplary amyloid plaque-associated molecules. Induction of an immune response against any of these molecules, alone or in combination with immunogenic therapeutic compositions against the fibril components described above or against any of the other non-fibril forming components described below, provides an additional anti-amyloid treatment regimen, in accordance with the present invention. Also forming part of the present invention are passive immunization regimens based on such plaque components, as described herein.

By way of example, synuclein is a protein that is structurally similar to apolipoproteins but is found in neuronal cytosol, particularly in the vicinity of presynaptic terminals. There are at least three forms of the protein, termed α, β and γ synuclein. Recently, it has been shown that a and 0 synuclein are involved in nucleation of amyloid deposits in certain amyloid diseases, particularly Alzheimer's disease. (Clayton, D. F., et al., TINS 21(6): 249–255, 1998). More specifically, a fragment of the NAC domain of α and β synuclein (residues 61–95) has been isolated from amyloid plaques in Alzheimer's patients; in fact this fragment comprises about 10% of the plaque that remains insoluble after solubilization with sodium dodecyl sulfate (SDS). (George, J. M., et al. Neurosci. News 1:1 2–17, 1995). Further, both the full length at synuclein and the NAC fragment thereof have been reported to accelerate the aggregation of β-amyloid peptide into insoluble amyloid in vitro. (Clayton, supra).

Additional components associated with amyloid plaques include non-peptide components. For example, perlecan and perlecan-derived glycosaminoglycans are large heparin sulfate proteoglycans that are present in Aβ-containing amyloid plaques of Alzheimer's disease and other CNS and systemic amyloidoses, including amylin plaques associated with diabetes. These compounds have been shown to enhance Aβ fibril formation. Both the core protein and glycosaminoglycan chains of perlecan have been shown to participate in binding to Aβ. Additional glycosaminoglycans, specifically, dermatan sulfate, chondroitin-4-sulfate, and pentosan polysulfate, are commonly found in amyloid plaques of various types and have also been shown to enhance fibril formation. Dextran sulfate also has this property. This enhancement is significantly reduced when the molecules are de-sulfated. Immunogenic therapeutics directed against the sulfated forms of glycosaminoglycans, including the specific glycosaminoglycans themselves, form an additional embodiment of the present invention, either as a primary or secondary treatment. Production of such molecules, as well as appropriate therapeutic compositions containing such molecules, is within the skill of the ordinary practitioner in the art.

2. Agents Inducing Passive Immune Response

Therapeutic agents of the invention also include immune reagents, such as antibodies, that specifically bind to fibril peptides or other components of amyloid plaques. Such antibodies can be monoclonal or polyclonal, and have binding specificities that are consonant with the type of amyloid disease to be targeted. Therapeutic compositions and treatment regimens may include a antibodies directed to a single binding domain or epitope on a particular fibril or non-fibril component of a plaque, or may include antibodies directed to two or more epitopes on the same component or antibodies directed to epitopes on multiple components of the plaque.

For example, in experiments carried out in support of the present invention, 8½ to 10½ month old PDAPP mice were given intraperitoneal (i.p.) injections of polyclonal anti-Aβ42 or monoclonal anti-Aβ antibodies prepared against specific epitopes of Aβ peptide, or saline, as detailed in Example XI herein. In these experiments, circulating antibody concentrations were monitored, and booster injections were given as needed to maintain a circulating antibody concentration of greater than 1:1000 with respect to the specific antigen to which the antibody was made. Reductions in total Aβ levels were observed, compared to control, in the cortex, hippocampus and cerebellum brain regions of antibody-treated mice; highest reductions were exhibited in mice treated with polyclonal antibodies in these studies.

In further experiments carried out in support of the invention, a predictive ex vivo assay (Example XIV) was used to test clearing of an antibody against a fragment of synuclein referred to as NAC. Synuclein has been shown to be an amyloid plaque-associated protein. An antibody to NAC was contacted with a brain tissue sample containing amyloid plaques and microglial cells. Rabbit serum was used as a control. Subsequent monitoring showed a marked reduction in the number and size of plaques indicative of clearing activity of the antibody.

From these data, it is apparent that amyloid plaque load associated with Alzheimer's disease and other amyloid diseases can be greatly diminished by administration of immune reagents directed against epitopes of Aβ peptide or against the NAC fragment of synuclein, which are effective to reduce amyloid plaque load. It is further understood that a wide variety of antibodies can be used in such compositions. Antibodies that bind specifically to the aggregated form of Aβ without binding to the dissociated form are suitable for use in the invention, as are antibodies that bind specifically to the dissociated form without binding to the aggregated form. Other suitable antibodies bind to both aggregated and dissociated forms. Some such antibodies bind to a naturally occurring short form of Aβ (i.e., Aβ39, 40 or 41) without binding to a naturally occurring long form of Aβ (i.e., Aβ42 and Aβ43). Some antibodies bind to a long form without binding to a short form. Some antibodies bind to Aβ without binding to full-length amyloid precursor protein. Some antibodies bind to Aβ with a binding affinity greater than or equal to about $10^6$, $10^7$, $10^8$, $10^9$, or $10^1$ $M^{-1}$.

Polyclonal sera typically contain mixed populations of antibodies binding to several epitopes along the length of Aβ. Monoclonal antibodies bind to a specific epitope within Aβ that can be a conformational or nonconformational epitope. Some monoclonal antibodies bind to an epitope within residues 1–28 of Aβ (with the first N terminal residue of natural Aβ designated 1). Other monoclonal antibodies bind to an epitope with residues 1–10 of Aβ. There are also monoclonal antibodies that bind to an epitope with residues 1–16 of Aβ. Other monoclonal antibodies bind to an epitope with residues 1–25 of Aβ. Some monoclonal antibodies bind to an epitope within amino acids 1–5, 5–10, 10–15, 15–20, 25–30, 10–20, 20, 30, or 10–25 of Aβ. Prophylactic and therapeutic efficacy of antibodies can be tested using the transgenic animal model procedures described in the Examples.

More generally, from the teachings provided herein, practitioners can design, produce and test antibodies directed to fibril proteins or peptides characteristic of other amyloid diseases, such as the diseases described in Section 2 herein, using compositions described herein, as well as antibodies against other amyloid components.

a. General Characteristics of Immunoglobulins

The basic antibody structural unit is known to comprise a tetramer of subunits. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y., 1989), Ch. 7 (incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901–917 (1987); Chothia et al., *Nature* 342:878–883 (1989).

b. Production of Non-human Antibodies

The production of non-human monoclonal antibodies, e.g., murne, guinea pig, rabbit or rat, can be accomplished by, for example, immunizing the animal with a plaque component, such as Aβ or other fibril components. A longer polypeptide comprising AP or an immunogenic fragment of Aβ or anti-idiotypic antibodies to an antibody to Aβ can also be used. See e.g., Harlow & Lane, Antibodies, A Laboratory Manual(CSHP NY, 1988) (incorporated by reference for all purposes). Such an immunogen can be obtained from a natural source, by peptide synthesis or by recombinant expression. Optionally, the immunogen can be administered fused or otherwise complexed with a carrier protein, as described below. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to the immunogen. Optionally, antibodies are further screened for binding to a specific region of the immunogen. For example, in the case of Aβ peptide as immunogen, screening can be accomplished by determining binding of an antibody to a collection of deletion mutants of an Aβ peptide and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to the component. If the test and reference antibodies compete, then they bind to the same epitope or epitopes sufficiently proximal that binding of one antibody interferes with binding of the other.

c. Chimeric and Humanized Antibodies

Chimeric and humanized antibodies have the same or similar binding specificity and affinity as a mouse or other nonhuman antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a mouse-antibody, (referred to as the donor immunoglobulin). See, Queen et al., *Proc. Natl. Acad. Sci. USA* 86:10029–10033 (1989) and WO 90/07861, U.S. Pat. No. 5,693,762, U.S. Pat. No. 5,693,761, U.S. Pat. No. 5,585,089, U.S. Pat. No. 5,530,101 and Winter, U.S. Pat. No. 5,225,539 (incorporated by reference in their entirety for all purposes). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid:
(1) noncovalently binds antigen directly,
(2) adjacent to a CDR region,
(3) otherwise interacts with a CDR region (e.g. is within about 6 A of a CDR region), or
(4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

d. Human Antibodies

Human antibodies against Aβ are provided by a variety of techniques described below. Some human antibodies are selected by competitive binding experiments, or otherwise, to have the same epitope specificity as a particular mouse antibody, such as one of the mouse monoclonals described in Example XI. Human antibodies can also be screened for a particular epitope specificity by using only a fragment of Aβ as the immunogen, and/or by screening antibodies against a collection of deletion mutants of Aβ.

(1) Trioma Methodology

The basic approach and an exemplary cell fusion partner, SPAZ-4, for use in this approach have been described by Oestberg et al., *Hybridoma* 2:361–367 (1983); Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells-two human and one mouse. Initially, a mouse myeloma line is fused with a human B-lymphocyte to obtain a non-antibody-producing xenogeneic hybrid cell, such as the SPAZ4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

The immunized B-lymphocytes are obtained from the blood, spleen, lymph nodes or bone marrow of a human donor. If antibodies against a specific antigen or epitope are desired, it is preferable to use that antigen or epitope thereof for immunization. Immunization can be either in vivo or in vitro. For in vivo immunization, B cells are typically isolated from a human immunized with Aβ, a fragment thereof, larger polypeptide containing Aβ or fragment, or an anti-idiotypic antibody to an antibody to Aβ. In some methods, B cells are isolated from the same patient who is ultimately to be administered antibody therapy. For in vitro immunization, B-lymphocytes are typically exposed to antigen for a period of 7–14 days in a media such as RPMI-1640 (see Engleman, supra) supplemented with 10% human plasma.

The immunized B-lymphocytes are fused to a xenogeneic hybrid cell such as SPAZ-4 by well known methods. For example, the cells are treated with 40–50% polyethylene glycol of MW 1000–4000, at about 37 degrees C., for about 5–10 min. Cells are separated from the fusion mixture and propagated in media selective for the desired hybrids (e.g., HAT or AH). Clones secreting antibodies having the required binding specificity are identified by assaying the trioma culture medium for the ability to bind to Aβ or a fragment thereof. Triomas producing human antibodies having the desired specificity are subcloned by the limiting dilution technique and grown in vitro in culture medium. The trioma cell lines obtained are then tested for the ability to bind Aβ or a fragment thereof.

Although triomas are genetically stable they do not produce antibodies at very high levels. Expression levels can be increased by cloning antibody genes from the trioma into one or more expression vectors, and transforming the vector into standard mammalian, bacterial or yeast cell lines, according to methods well known in the art.

(2) Transgenic Non-human Mammals

Human antibodies against Aβ can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heady and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148, 1547–1553 (1994), *Nature Biotechnology* 14, 826 (1996), Kucherlapati, WO 91/10741 (1991) (each of which is incorporated by reference in its entirety for all purposes). Transgenic mice are particularly suitable in this regard. Anti-Aβ antibodies are obtained by immunizing a transgenic nonhuman mammal, such as described by Lonberg or Kucherlapati, supra, with Aβ or a fragment thereof Monoclonal antibodies are prepared by, e.g., fusing B-cells from such mammals to suitable myeloma cell lines using conventional Kohler-Milstein technology. Human polyclonal antibodies can also be provided in the form of serum from humans immunized with an immunogenic agent. Optionally, such polyclonal antibodies can be concentrated by affinity purification using Aβ or other immunogen amyloid peptide as an affinity reagent.

(3) Phage Display Methods

A further approach for obtaining human anti-Aβ antibodies is to screen a DNA library from human B cells according to the general protocol outlined by Huse et al., *Science* 246:1275–1281 (1989). For example, as described for trioma methodology, such B cells can be obtained from a human immunized with Aβ, fragments, longer polypeptides containing Aβ or fragments or anti-idiotypic antibodies. Optionally, such B cells are obtained from a patient who is ultimately to receive antibody treatment. Antibodies binding to an epitope of the amyloid component of interest, such as Aβ or a fragment thereof are selected. Sequences encoding such antibodies (or a binding fragments) are then cloned and amplified. The protocol described by Huse is rendered more efficient in combination with phage-display technology. See, e.g., Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332 (each of which is incorporated by reference in its entirety for all purposes). In these methods, libraries of phage are produced in which members display different antibodies on their outer surfaces. Antibodies are usually displayed as Fv or Fab fragments. Phage displaying antibodies with a desired specificity are selected by affinity enrichment to an Aβ peptide or fragment thereof.

In a variation of the phage-display method, human antibodies having the binding specificity of a selected murine antibody can be produced. See Winter, WO 92/20791. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. A phage showing strong specific binding for the component of interest (e.g., at least $10^8$ and preferably at least $10^9$ M$^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for amyloid peptide component are selected. These phage display the variable regions of completely human anti-amyloid peptide antibodies. These antibodies usually have the same or similar epitope specificity as the murine starting material.

e. Selection of Constant Region

The heavy and light chain variable regions of chimeric, humanized, or human antibodies can be linked to at least a portion of a human constant region. The choice of constant region depends, in part, whether antibody-dependent complement and/or cellular mediated toxicity is desired. For example, isotopes IgG1 and IgG3 have complement activity and isotypes IgG2 and IgG4 do not. Choice of isotype can also affect passage of antibody into the brain. Light chain constant regions can be lambda or kappa. Antibodies can be expressed as tetramers containing two light and two heavy chains, as separate heavy chains, light chains, as Fab, Fab'F(ab')$_2$ and Fv, or as single chain antibodies in which heavy and light chain variable domains are linked through a spacer.

f. Expression of Recombinant Antibodies

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly usefull for cloning the DNA sequences of the present invention. Microbes, such as yeast are also useful for expression. Saccharomyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines, various COS cell lines, HeLa cells, L cells and myeloma cell lines. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (e.g., according to methods described in U.S. Pat. No. 5,741,957, U.S. Pat. No. 5,304,489, U.S. Pat. No. 5,849,992, all incorporated by reference herein in their entireties). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, gel electrophoresis and the like (see generally, Scopes, Protein Purification (Springer-Verlag, NY, 1982)).

4. Other Therapeutic Agents

Therapeutic agents for use in the present methods also include T-cells that bind to a plaque component, such as Aβ peptide. For example, T-cells can be activated against Aβ peptide by expressing a human MHC class I gene and a human β-2-microglobulin gene from an insect cell line, whereby an empty complex is formed on the surface of the cells and can bind to Aβ peptide. T-cells contacted with the cell line become specifically activated against the peptide. See Peterson et al., U.S. Pat. No. 5,314,81. Insect cell lines expressing an MHC class II antigen can similarly be used to activate CD4 T cells.

5. Carrier Proteins

Some agents for inducing an immune response contain the appropriate epitope for inducing an immune response against amyloid deposits but are too small to be immunogenic. In this situation, a peptide immunogen can be linked to a suitable carrier to help elicit an immune response. Suitable carriers include serum albumins, keyhole limpet hemocyanin, immunoglobulin molecules, thyroglobulin, ovalburnin, tetanus toxoid, or a toxoid from other pathogenic bacteria, such as diphtheria, *E. coli, cholera*, or *H. pylori*, or an attenuated toxin derivative. Other carriers include T-cell epitopes that bind to multiple MHC alleles, e.g., at least 75% of all human MHC alleles. Such carriers are sometimes known in the art as "universal T-cell epitopes." Examples of universal T-cell epitopes include:

Influenza Hemagluttinin: $HA_{307-319}$ PKYVKQNTLKLAT (SEQ ID NO: 1)

PADRE (common residues bolded) AKXVAAWTLKAAA (SEQ ID NO: 2)

Malaria CS: T3 epitope EKKIAKMEKASSVFNV (SEQ ID NO: 3)

Hepatitis B surface antigen: $HBsAg_{19-28}$ FFLLTRILTI (SEQ ID NO: 4)

Heat Shock Protein 65: $hsp65_{153-171}$ DQSIGDLIAEAMDKVGNEG (SEQ ID NO: 5)

bacille Calmette-Guerin QVHFQPLPPAVVKL (SEQ ID NO: 6)

Tetanus toxoid: $TT_{830-844}$ QYIKANSKFIGITEL (SEQ ID NO: 7)

Tetanus toxoid: $TT_{947-967}$ FNNFTVSFWLRVPKVSASHLE (SEQ ID NO: 8)

HIV gp120 T1: KQIINMWQEVGKAMYA. (SEQ ID NO: 9)

Other carriers for stimulating or enhancing an immune response include cytokines such as IL-1, IL-1α and β peptides, IL-2, γINF, IL-10, GM-CSF, and chemokines, such as MIP1α and β and RANTES. Immunogenic agents can also be linked to peptides that enhance transport across tissues, as described in O'Mahony, WO 97/17613 and WO 97/17614.

Immunogenic agents can be linked to carriers by chemical crosslinking. Techniques for linking an immunogen to a carrier include the formation of disulfide linkages using N-succinimidyl-3-(2-pyridyl-thio)propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the ε-amino on a lysine, or other amino group in other amino acids. A variety of such disulfide/amide-forming agents are described by *Immun. Rev.* 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimidomethyl)cyclohexane-1-carboxylic acid. The carboxyl groups can be activated by combining them with succinimide or 1-hydroxyl-2-nitro-4-sulfonic acid, sodium salt.

Immunogenic peptides can also be expressed as fusion proteins with carriers (i.e., heterologous peptides). The immunogenic peptide can be linked at its amino terminus, its carboxyl terminus, or both to a carrier. Optionally, multiple repeats of the immunogenic peptide can be present in the fusion protein. Optionally, an immunogenic peptide can be linked to multiple copies of a heterologous peptide, for example, at both the N and C termini of the peptide. Some carrier peptides serve to induce a helper T-cell response against the carrier peptide. The induced helper T-cells in turn induce a B-cell response against the immunogenic peptide linked to the carrier peptide.

Some agents of the invention comprise a fusion protein in which an N-terminal fragment of Aβ is linked at its C-terminus to a carrier peptide. In such agents, the N-terminal residue of the fragment of Aβ constitutes the N-terminal residue of the fusion protein. Accordingly, such fusion proteins are effective in inducing antibodies that bind to an epitope that requires the N-terminal residue of Aβ to be in free form. Some agents of the invention comprises a plurality of repeats of an N-terminal segment of Aβ linked at the C-terminus to one or more copy of a carrier peptide. The N-terminal fragment of Aβ incorporated into such fusion proteins sometimes begins at Aβ1–3 and ends at Aβ7–11. Aβ1–7, Aβ1–3, 1–4, 1–5, and 3–7 are preferred N-terminal fragment of Aβ. Some fusion proteins comprise different N-terminal segments of Aβ in tandem. For example, a fusion protein can comprise Aβ1–7 followed by Aβ1–3 followed by a heterologous peptide.

In some fusion proteins, an N-terminal segment of Aβ is fused at its N-terminal end to a heterologous carrier peptide. The same variety of N-terminal segments of Aβ can be used as with C-terminal fusions. Some fusion proteins comprise a heterologous peptide linked to the N-terminus of an N-terminal segment of Aβ, which is in turn linked to one or more additional N-terminal segments of Aβ in tandem.

Some examples of fusion proteins suitable for use in the invention are shown below. Some of these fusion proteins comprise segments of Aβ linked to tetanus toxoid epitopes such as described in U.S. Pat. No. 5,196,512, EP 378,881 and EP 427,347. Some fusion proteins comprises segments of Aβ linked to carrier peptides described in U.S. Pat. No. 5,736,142. Some heterologous peptides are universal T-cell epitopes. In some methods, the agent for administration is simply a single fusion protein with an Aβ segment linked to a heterologous segment in linear configuration. In some methods, the agent is multimer of fusion proteins represented by the formula $2^x$, in which x is an integer from 1–5. Preferably x is 1, 2 or 3, with 2 being most preferred. When x is two, such a multimer has four fusion proteins linked in a preferred configuration referred to as MAP4 (see U.S. Pat. No. 5,229,490). Epitopes of Aβ are underlined.

The MAP4 configuration is shown below, where branched structures are produced by initiating peptide synthesis at both the N terminal and side chain amines of lysine. Depending upon the number of times lysine is incorporated into the sequence and allowed to branch, the resulting structure will present multiple N termini. In this example, four identical N termini have been produced on the branched lysine-containing core. Such multiplicity greatly enhances the responsiveness of cognate B cells.

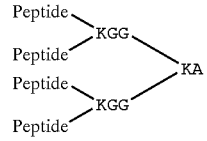

AN90549 (Aβ1–7/Tetanus toxoid 830–844 in a MAP4 configuration):
DAEFRHDQYIKANSKFIGITEL (SEQ ID NO: 10)
AN90550 (Aβ1–7/Tetanus toxoid 947–967 in a MAP4 configuration):
DAEFRHDFNNFTVSFWLRVPKVSASHLE (SEQ ID NO: 11)
AN90542 (Aβ1–7/Tetanus toxoid 830–844+947–967 in a linear configuration):
DAEFRHDQYIKANSKFIGITELFNNFTVSFWLR-VPKVSASHLE (SEQ ID NO: 12)
AN90576: (Aβ3–9)/Tetanus toxoid 830844 in a MAP4 configuration):
EFRHDSGQYIKANSKFIGITEL (SEQ ID NO: 13)
Peptide described in U.S. Pat. No. 5,736,142 (all in linear configurations).
AN90562 (Aβ1–7/peptide) AKXVAAWTLKAAA DAEFRHD (SEQ ID NO: 14)
AN90543 (Aβ1–7×3/peptide): DAEFRHDDAEFRHDDAEFRHDAKXVAAWTL-KAAA (SEQ ID NO: 15)

Other examples of fusion proteins (immunogenic epitope of Aβ bolded) include
AKXVAAWTLKAAA-DAEFRHD-DAEFRHHD-DAEFRIID (SEQ ID NO: 16)
DAEFRHD-AKXVAAWTLKAAA (SEQ ID NO: 17)
DAEFRHD-ISQAVHAAHAEINEAGR (SEQ ID NO: 18)
FRIIDSGY-ISQAVHAAHAEINEAGR (SEQ ID NO: 19)
EFRHDSG-ISQAVHAAHAEINMAGR (SEQ ID NO: 20)
PKYVKQNTLKLAT-DAEFRHD-DAEFRHD-DAEFRHD (SEQ ID NO: 21)
DAEFRHD-PKYVKQNTLKLAT-DAEFRHD (SEQ ID NO: 22)
DAEFRHD-DAEFRHD-DAEFRHD-PKYVKQNTLKLAT (SEQ ID NO: 23)
DAEFRHD-DAEFRHD-PKYVKQNTLKLAT (SEQ ID NO: 24)
DAEFRH D-PKYVKQNTLKLAT-EKKIAKMEKASSVFNV-QYIKANSKFIGITEL-FNNFTVSFWLRVPKVSASHLE-DEFRIRD DAEFRHD-DAEFRHD-DAEFRHD-QYIKANSKFIGITEL-FNNFTVSFWLRVPKVSASHLE (SEQ ID NO: 25)
DAEFRHD-QYIKANSKFIGITELCFNNFTVSFWL-RVPKVSASHLE (SEQ ID NO: 26)
DAEFRIID-QYIKNSKFIGITELCFNNFTVSFWLR-VPKVSASHLE-DAEFRHD (SEQ ID NO: 27)
DAEFRHD-QYIKANSKFIGITEL (SEQ ID NO: 28)on a 2 branched resin

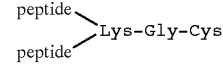

EQVTNVGGAISQAVHAAHAEINEAGR (Synuclein fusion protein in MAP-4 configuration; SEQ ID NO: 29)

The same or similar carrier proteins and methods of linkage can be used for generating immunogens to be used in generation of antibodies against Aβ for use in passive immunization. For example, Aβ or a fragment linked to a carrier can be administered to a laboratory animal in the production of monoclonal antibodies to Aβ.

6. Nucleic Acid Encoding Therapeutic Agents

Immune responses, against amyloid deposits can also be induced by administration of nucleic acids encoding selected peptide immunogens, or antibodies and their component chains used for passive immunization. Such nucleic acids can be DNA or RNA. A nucleic acid segment encoding an immunogen is typically linked to regulatory elements, such as a promoter and enhancer, that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors.

A number of viral vector systems are available including retroviral systems (see, e.g., Lawrie and Tumin, Cur. Opin. Genet. Develop. 3, 102–109, 1993); adenoviral vectors (see, e.g., Bett et al., *J. Virol.* 67, 5911, 1993); adeno-associated virus vectors (see, e.g., Zhou et al., *J. Exp. Med.* 179, 1867, 1994), viral vectors from the pox family including vaccinia virus and the avian pox viruses, viral vectors from the alpha virus genus such as those derived from Sindbis and Semliki Forest Viruses (see, e.g., Dubensky et al., *J. Virol.* 70, 508–519, 1996), Venezuelan equine encephalitis virus (see U.S. Pat. No. 5,643,576) and rhabdoviruses, such as vesicular stomatitis virus (see WO 96/34625)and papillomaviruses (Ohe et al., *Human Gene Therapy* 6, 325–333, 1995); Woo et al., WO 94/12629 and Xiao & Brandsma, *Nucleic Acids. Res.* 24, 2630–2622, 1996).

DNA encoding an immunogen, or a vector containing the same, can be packaged into liposomes. Suitable lipids and related analogs are described by U.S. Pat. Nos. 5,208,036, 5,264,618, 5,279,833 and 5,283,185. Vectors and DNA encoding an immunogen can also be adsorbed to or associated with particulate carriers, examples of which include polymethyl methacrylate polymers and polylactides and poly(lactide-co-glycolides), see, e.g., McGee et al., *J. Micro Encap.* (1996).

Gene therapy vectors or naked DNA can be delivered in vivo by administration to an individual patient, typically by systemic administration (e.g., intravenous, intraperitoneal, intranasal, gastric, intradermal, intramuscular, subdermal, or intracranial infusion) or topical application (see e.g., U.S. Pat. No. 5,399,346). Such vectors can further include facilitating agents such as bupivacaine U.S. Pat. No. 5,593,970). DNA can also be administered using a gene gun. See Xiao & Brandsma, supra. The DNA encoding an immunogen is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agracetus, Inc., (Middleton, Wis.) is suitable. Alternatively, naked DNA can pass through skin into the blood stream simply by spotting the DNA onto skin with chemical or mechanical irritation (see WO 95/05853).

In a further variation, vectors encoding immunogens can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

7. Screening Antibodies for Clearing Activity

Example XIV describes methods of screening an antibody for activity in clearing an amyloid deposit. To screen for activity against an amyloid deposit, a tissue sample from a patient with amyloidosis, such as brain tissue in Alzheimer's disease, or an animal model having characteristic amyloid pathology is contacted with phagocytic cells bearing an Fc receptor, such as microglial cells, and the antibody under test in a medium in vitro. The phagocytic cells can be a primary culture or a cell line, such as BV-2, C8-B4, or THP-1. These components are combined on a microscope slide to facilitate microscopic monitoring, or multiple reactions may be performed in parallel in the wells of a microtiter dish. In such a format, a separate miniature microscope slide can be mounted in the separate wells, or a nonmicroscopic detection format, such as ELISA detection of Aβ can be used. Preferably, a series of measurements is made of the amount of amyloid deposit in the in vitro reaction mixture, starting from a baseline value before the reaction has proceeded, and one or more test values during the reaction. The antigen can be detected by staining, for example, with a fluorescently labelled antibody to Aβ or other component of amyloid plaques. The antibody used for staining may or may not be the same as the antibody being tested for clearing activity. A reduction relative to baseline during the reaction of the amyloid deposits indicates that the antibody under test has clearing activity. Such antibodies are likely to be useful in preventing or treating Alzheimer's and other amyloidogenic diseases. As described above, experiments carried out in support of the present invention revealed, using such an assay, that antibodies to the NAC fragment of synuclein are effective to clear amyloid plaques characteristics of Alzheimer's disease.

D. Patients Amenable to Anti-amyloid Treatment Regimens

Patients amenable to treatment include individuals at risk of disease but not showing symptoms, as well as patients presently showing symptoms of amyloidosis. In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods are especially useful for individuals who do have a known genetic risk of Alzheimer's disease or any of the other hereditary amyloid diseases. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests arc available for identifying individuals who have AD. These include measurement of CSF tau and Aβ42 levels. Elevated tau and decreased Aβ42 levels signify the presence of AD. Individuals suffering from Alzheimer's disease can also be diagnosed by MMSE or ADRDA criteria as discussed in the Examples section.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to the therapeutic agent (e.g., Aβ peptide) over time, along the lines described in Examples I and II herein. If the response falls, a booster dosage is indicated. In the case of potential Down's syndrome patients, treatment can begin antenatally by administering therapeutic agent to the mother or shortly after birth.

Other forms amyloidosis often go undiagnosed, unless a particular predilection for the disease is suspected. One prime symptom is the presence of cardiac or renal disease in a middle-aged to elderly patient who also has signs of other organ involvement. Low voltage or extreme axis deviations of the electrocardiogram and thickened ventricular tissue may be indicative of cardiac involvement. Proteinuria is a symptom of renal involvement. Hepatic involvement may also be suspected, if hepatomegaly is detected by physical examination of the patient. Peripheral neuropathy is also a common occurrence in certain forms of amyloidoses; autonomic neuropathy, characterized by postural hypotension, may also be found. Amyloidosis should be suspected in anyone with a progressive neuropathy of indeterminate origin. A definitive diagnosis of the disease can be made using tissue biopsy methods, where the affected organ(s) are available. For systemic amyloidoses, a fat pad aspirated or rectal biopsy samples may be used. The biopsy material is stained with Congo red, with positive samples exhibiting apple green birefringence under polarized light microscopy.

E. Treatment Regimens

In prophylactic applications, pharmaceutical compositions or medicaments are administered to a patient susceptible to, or otherwise at risk of, a particular disease in an amount sufficient to eliminate or reduce the risk or delay the outset of the disease In therapeutic applications, compositions or medicaments are administered to a patient suspected of, or already suffering from such a disease in an amount sufficient to cure, or at least partially arrest, the symptoms of the disease and its complications. An amount adequate to accomplish this is defined as a therapeutically- or pharmaceutically-effective dose. In both prophylactic and therapeutic regimes, agents are usually administered in several dosages until a sufficient immune response has been achieved. Typically, the immune response is monitored and repeated dosages are given if the immune response starts to wane.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but in some diseases, such as prion protein-associated mad cow disease, the patient can be a nonhuman mammal, such as a bovine. Treatment dosages need to be titrated to optimize safety and efficacy. The amount of immunogen depends on whether adjuvant is also administered, with higher dosages generally being required in the absence of adjuvant. Depending on the immunogenicity of the particular formulation, an amount of an immunogen for administration may vary from 1 $\mu$g–500 $\mu$g per patient and more usually from 5–500 $\mu$g per injection for human administration. Occasionally, a higher dose of 0.5–5 mg per injection is used. Typically at least about 10, 20, 50 or 100 $\mu$g is used for each human injection. The timing of injections can vary significantly from once a day, to once a year, to once a decade, with successive "boosts" of immunogen somewhat preferred. Generally, in accordance with the teachings provided herein, effective dosages can be monitored by obtaining a fluid sample from the patient, generally a blood serum sample, and determining the titer of antibody developed against the immunogen, using methods well known in the art and readily adaptable to the specific antigen to be measured. Ideally, a sample is taken prior to initial dosing; subsequent samples are taken and titered after each immunization. Generally, a dose or dosing schedule which provides a detectable titer at least four times greater than control or "background" levels at a serum dilution of 1:100 is desirable, where background is defined relative to a control serum or relative to a plate background in ELISA assays. Titers of at least 1:1000 or 1:5000 are preferred in accordance with the present invention.

On any given day that a dosage of immunogen is given, the dosage is usually greater than about 1 $\mu$g/patient and preferably greater than 10 $\mu$g/patient if adjuvant is also administered, and at least greater than 10 $\mu$g/patient and usually greater than 100 $\mu$g/patient in the absence of adjuvant. Doses for individual immunogens, selected in accordance with the present invention, are determined according to standard dosing and titering methods, taken in conjunction with the teachings provided herein. A typical regimen consists of an immunization followed by booster injections at time intervals, such as 6 week intervals. Another regimen consists of an immunization followed by booster injections 1, 2 and 12 months later. Another regimen entails an injection every two months for life. Alternatively, booster injections can be on an irregular basis as indicated by monitoring of immune response.

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to A$\beta$ in the patient. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 $\mu$g to 10 mg, or 30–300 $\mu$g DNA per patient. Doses for infectious viral vectors vary from 10–100, or more, virions per dose.

Agents for inducing an immune response can be administered by parenteral, topical, intravenous, oral, subcutaneous, intraperitoneal, intranasal or intramuscular means for prophylactic and/or therapeutic treatment. Typical routes of administration of an immunogenic agent are intramuscular (i.m.), intravenous (i.v.) or subcutaneous (s.c.), although other routes can be equally effective. Intramuscular injection is most typically performed in the arm or leg muscles. In some methods, agents are injected directly into a particular tissue where deposits have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treatment of amyloidogenic disease. In the case of Alzheimer's and Down's syndrome, in which amyloid deposits occur in the brain, agents of the invention can also be administered in conjunction with other agents that increase passage of the agents of the invention across the blood-brain barrier. Further, therapeutic cocktails comprising immunogens designed to provoke an immune response against more than one amyloid component are also contemplated by the present invention, as are a combination of an antibody directed against one plaque component and an immunogen directed to a different plaque component.

Immunogenic agents of the invention, such as peptides, are sometimes administered in combination with an adjuvant. A variety of adjuvants can be used in combination with a peptide, such as Aβ, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., in *Vaccine Design: The Subunit and Adjuvant Approach* (eds. Powell & Newman, Plenum Press, NY, 1995); U.S. Pat. No. 5,057,540), (Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., *N. Engl. J. Med.* 336, 86–91 (1997)). Another adjuvant is CpG (WO 98/40100). Alternatively, Aβ can be coupled to an adjuvant. However, such coupling should not substantially change the conformation of Aβ so as to affect the nature of the immune response thereto. Adjuvants can be administered as a component of a therapeutic composition with an active agent or can be administered separately, before, concurrently with, or after administration of the therapeutic agent.

A preferred class of adjuvants is aluminum salts (alum), such as aluminum hydroxide, aluminum phosphate, aluminum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such ajuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutaamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramiderM, or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi Immunochem, Hamilton, Mont.) containing 2% squalene, 0.2% Tween 80, and one or more bacterial cell wall components from the group consisting of monophosphoryl lipid A, trehalose dimycolate (TDM), and cell wall skeleton (CWS), preferably MPL+CWS (Detox™). Another class of preferred adjuvants is saponin adjuvants, such as Stimulon™ (QS-21; Aquila, Framingham, Mass.) or particles generated therefrom such as ISCOMs (immunostimulating complexes) and ISCOMATRIX. Other adjuvants include Incomplete Freund's Adjuvant (IFA), cytokines, such as interleukins (IL-1, IL-2, and IL-12), macrophage colony stimulating factor (M-CSF), and tumor necrosis factor (TNF). Such adjuvants are generally available from commercial sources.

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on such factors as the stability of the formulation containing the adjuvant, the route of administration, the dosing schedule, and the efficacy of the adjuvant for the species being vaccinated. In humans, a preferred pharmaceutically acceptable adjuvant is one that has been approved for human administration by pertinent regulatory bodies. Examples of such preferred adjuvants for humans include alum, MPL and QS-21. Optionally, two or more different adjuvants can be used simultaneously. Preferred combinations include alum with MPL, alum with QS-21, MPL with QS-21, and alum, QS-21 and MPL together. Also, Incomplete Freund's adjuvant can be used (Chang et al., *Advanced Drug Delivery Reviews* 32, 173–186 (1998)), optionally in combination with any of alum, QS-21, and MPL and all combinations thereof.

Agents of the invention are often administered as pharmaceutical compositions comprising an active therapeutic agent and a variety of other pharmaceutically acceptable components. See *Remington's Pharmaceutical Science* (19th ed., 1995). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized sepharose, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249, 1527 (1990) and Hanes, *Advanced Drug Delivery Reviews* 28, 97–119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%–2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%–95% of active ingredient, preferably 25%–70%.

Topical application can result in transdermal or intradermal delivery. Topical administration can be facilitated by co-administration of the agent with *cholera* toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein.

Alternatively, transdermal delivery can be achieved using a skin patch or using transferosomes (Paul et al., *Eur. J. Immunol.* 25, 3521–24 (1995); Cevc et al., *Biochem. Biophys. Acta* 1368, 201–15 (1998)).

F. Methods of Diagnosis

The invention provides methods of detecting an immune response against Aβ peptide in a patient suffering from or susceptible to Alzheimer's disease. The methods are particularly useful for monitoring a course of treatment being administered to a patient. The methods can be used to monitor both therapeutic treatment on symptomatic patients and prophylactic treatment on asymptomatic patients. The methods are useful for monitoring both active immunization (e.g., antibody produced in response to administration of immunogen) and passive immunization (e.g., measuring level of administered antibody).

1. Active Immunization

Some methods entail determining a baseline value of an immune response in a patient before administering a dosage of agent, and comparing this with a value for the immune response after treatment. A significant increase (i.e., greater than the typical margin of experimental error in repeat measurements of the same sample, expressed as one standard deviation from the mean of such measurements) in value of the immune response signals a positive treatment outcome (i.e., that administration of the agent has achieved or augmented an immune response). If the value for immune response does not change significantly, or decreases, a negative treatment outcome is indicated. In general, patients undergoing an initial course of treatment with an immunogenic agent are expected to show an increase in immune response with successive dosages, which eventually reaches a plateau. Administration of agent is generally continued while the immune response is increasing. Attainment of the plateau is an indicator that the administered of treatment can be discontinued or reduced in dosage or frequency.

In other methods, a control value (i.e., a mean and standard deviation) of immune response is determined for a control population. Typically the individuals in the control population have not received prior treatment. Measured values of immune response in a patient after administering a therapeutic agent are then compared with the control value. A significant increase relative to the control value (e.g., greater than one standard deviation from the mean) signals a positive treatment outcome. A lack of significant increase or a decrease signals a negative treatment outcome. Administration of agent is generally continued while the immune response is increasing relative to the control value. As before, attainment of a plateau relative to control values in an indicator that the administration of treatment can be discontinued or reduced in dosage or frequency.

In other methods, a control value of immune response (e.g., a mean and standard deviation) is determined from a control population of individuals who have undergone treatment with a therapeutic agent and whose immune responses have plateaued in response to treatment. Measured values of immune response in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment regime, for example, use of a different adjuvant may be indicated.

In other methods, a patient who is not presently receiving treatment but has undergone a previous course of treatment is monitored for immune response to determine whether a resumption of treatment is required. The measured value of immune response in the patient can be compared with a value of immune response previously achieved in the patient after a previous course of treatment. A significant decrease relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

The tissue sample for analysis is typically blood, plasma, serum, mucous or cerebrospinal fluid from the patient. The sample is analyzed for indication of an immune response to the amyloid component of interest, such as any form of Aβ peptide. The immune response can be determined from the presence of, e.g., antibodies or T-cells that specifically bind to the component of interest, such as Aβ peptide. ELISA methods of detecting antibodies specific to Aβ are described in the Examples section and can be applied to other peptide antigens. Methods of detecting reactive T-cells are well known in the art.

2. Passive Immunization

In general, the procedures for monitoring passive immunization are similar to those for monitoring active immunization described above. However, the antibody profile following passive immunization typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of antibody to Aβ in the patient is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other patients. If the measured antibody level is significantly less than a reference level (e.g., less than the mean minus one standard deviation of the reference value in population of patients benefiting from treatment) administration of an additional dosage of antibody is indicated.

3. Diagnostic Kits

The invention further provides diagnostic kits for performing the diagnostic methods described above. Typically, such kits contain an agent that specifically binds to antibodies to an amyloid plaque component, such as Aβ, or reacts with T-cells specific for the component. The kit can also include a label. For detection of antibodies to Aβ, the label is typically in the form of labelled anti-idiotypic antibodies. For detection of antibodies, the agent can be supplied prebound to a solid phase, such as to the wells of a microtiter dish. For detection of reactive T-cells, the label can be supplied as 3H-thymidine to measured proliferative response. Kits also typically contain labelling providing directions for use of the kit. The labelling may also include a chart or other correspondence regime correlating levels of measured label with levels of antibodies to Aβ or T-cells reactive with Aβ. The term labelling refers to any written or recorded material that is attached to, or otherwise accompanies a kit at any time during its manufacture, transport, sale or use. For example, the term labelling encompasses advertising leaflets and brochures, packaging materials, instructions, audio or video cassettes, computer discs, as well as writing imprinted directly on kits.

EXAMPLES

I. Prophylactic Efficacy of Aβ Against Alzheimer's Disease (AD)

These examples describe administration of Aβ42 peptide to transgenic mice overexpressing APP with a mutation at position 717 ($APP_{717V \to F}$) that predisposes them to develop Alzheimer's-like neuropathology. Production and characteristics of these mice. (PDAPP mice) is described in Games et al., Nature, supra. These animals, in their heterozygote form, begin to deposit Aβ at six months of age forward. By fifteen months of age they exhibit levels of Aβ deposition equivalent to that seen in Alzheimer's disease. PDAPP mice were injected with aggregated $A\beta_{42}$ (aggregated $A\beta_{42}$) or phosphate buffered saline. Aggregated $A\beta_{42}$ was chosen because of its ability to induce antibodies to multiple epitopes of Aβ.

A. Methods

1. Source of Mice

Thirty PDAPP heterogenic female mice were randomly divided into the following groups: 10 mice for injection with aggregated Aβ42 (one died in transit), 5 mice to be injected with PBS/adjuvant or PBS, and 10 uninjected controls. Five mice were injected with peptides dervied from the sequence of serum amyloid protein (SAP).

2. Preparation of Immunogens

Preparation of aggregated Aβ42: two milligrams of A42 (US Peptides Inc, lot K-42-12) was dissolved in 0.9 ml water and made up to 1 ml by adding 0.1 ml 10×PBS. This was vortexed and allowed to incubate overnight 37° C., under which conditions the peptide aggregated. Any unused Aβ was stored as a dry lyophilized powder at −20° C. until the next injection.

It should be noted that when such commercially available peptides are used, the dry weights may include salt weights; weights reported in all Examples herein, unless otherwise indicated, include salt weights. Exact masses of peptide may be determined using standard assays of the preparation, such as nitrogen determination, in conjunction with the known composition.

3. Preparation of Injections

For each injection, 100 μg of aggregated Aβ42 in PBS per mouse was emulsified 1:1 with Complete Freund's adjuvant (CFA) in a final volume of 400 μl emulsion for the first immunization, followed by a boost of the same amount of immunogen in Incomplete Freund's adjuvant (IFA) at 2 weeks. Two additional doses in IFA were given at monthly intervals. The subsequent immunizations were done at monthly intervals in 500 μl of PBS. Injections were delivered intraperitoneally (i.p.).

PBS injections followed the same schedule and mice were injected with a 1:1 mix of PBS/Adjuvant at 400 μl per mouse, or 500 μl of PBS per mouse. SAP injections likewise followed the same schedule using a dose of 100 μg per injection.

4. Titration of Mouse Bleeds, Tissue Preparation and Immunohistochemistry

The above methods are described infra in General Materials and Methods.

B. Results

PDAPP mice were injected with either aggregated Aβ42 (aggregated Aβ42), SAP peptides, or phosphate buffered saline. A group of PDAPP mice were also left as uninjected, positive controls. The titers of the mice to aggregated Aβ42 were monitored every other month from the fourth boost until the mice were one year of age. Mice were sacrificed at 13 months. At all time points examined, eight of the nine aggregated Aβ42 mice developed a high antibody titer, which remained high throughout the series of injections (titers greater than 1/10000). The ninth mouse had a low, but measurable titer of approximately 1/1000 (FIG. 1, Table 3). SAPP-injected mice had titers of 1:1,000 to 1:30,000 for this immunogen with only a single mouse exceeding 1:10,0000.

TABLE 3A

Titers at 50% Maximal O.D.
Aggregated Aβ injected Mice

| Age of PDAPP (months) | #100 | #101 | #102 | #103 | #104 | #105 | #106 | #107 | #108 |
|---|---|---|---|---|---|---|---|---|---|
| 4 | 70000 | 150000 | 15000 | 120000 | 1000 | 15000 | 50000 | 60000 | 100000 |
| 6 | 15000 | 65000 | 30000 | 55000 | 300 | 15000 | 15000 | 50000 | 60000 |
| 8 | 20000 | 55000 | 50000 | 50000 | 400 | 15000 | 18000 | 50000 | 60000 |
| 10 | 40000 | 20000 | 60000 | 50000 | 900 | 15000 | 50000 | 20000 | 40000 |
| 12 | 25000 | 30000 | 60000 | 40000 | 2700 | 20000 | 70000 | 25000 | 20000 |

TABLE 3B

Titers at 50% Maximal O.D.
PBS injected Mice on both Immunogens at 1/00

| Age of PDAPP (months) | #113 | #114 | #115 | #116 | #117 |
|---|---|---|---|---|---|
| 6 | <4 × bkg | <4 × bkg | <4 × bkg | <4 × bkg | <4 × bkg |
| 10 | 5 × bkg | <4 × bkg | <4 × bkg | <4 × bkg | <4 × bkg |
| 12 | <4 × bkg | <4 × bkg | <4 × bkg | <4 × bkg | <4 × bkg |

Sera from PBS-treated mice were titered against aggregated Aβ42 at six, ten and twelve months. At a 1/100 dilution the PBS mice, when titered against aggregated Aβ42, only exceeded 4 times background at one data point, otherwise, they were less than 4 times background at all time points (Table 3). The SAP-specific response was negligible at these time points with all titers less than 300.

Seven out of the nine mice in the aggregated Aβ1–42 treated group had no detectable amyloid in their brains. In contrast, brain tissue from mice in the SAP and PBS groups contained numerous amyloid deposits in the hippocampus, as well as in the frontal and cingulate cortices. The pattern of deposition was similar to that of untreated controls, with characteristic involvement of vulnerable subregions, such as the outer molecular layer of the hippocampal dentate gyrus. One mouse from the Aβ1–42-injected group had a greatly reduced amyloid burden, confined to the hippocampus. An isolated plaque was identified in another Aβ1–42-treated mouse.

Quantitative image analyses of the amyloid burden in the hippocampus verified the dramatic reduction achieved in the Aβ42 (AN1792)-treated animals (FIG. 2). The median values of the amyloid burden for the PBS group (2.22%), and for the untreated control group (2.65%) were significantly greater than for those immunized with AN1792 (0.00%, p=0.0005). In contrast, the median value for the group immunized with SAP peptides (SAPP) was 5.74%. Brain tissue from the untreated, control mice contained numerous Aβ amyloid deposits visualized with the Aβ-specific monoclonal antibody (mAb) 3D6 in the hippocampus, as well as in the retrosplenial cortex. A similar pattern of amyloid deposition was also seen in mice immunized with SAPP or PBS (FIG. 2). In addition, in these latter three groups there was a characteristic involvement of vulnerable subregions of the brain classically seen in AD, such as the outer molecular layer of the hippocampal dentate gyrus, in all three of these groups.

The brains that contained no Aβ deposits were also devoid of neuritic plaques that are typically visualized in PDAPP mice with the human APP antibody 8E5. All of brains from the remaining groups (SAP-injected, PBS and uninjected mice) had numerous neuritic plaques typical of untreated PDAPP mice. A small number of neuritic plaques were present in one mouse treated with AN1792, and a single cluster of dystrophic neurites was found in a second mouse treated with AN1792. Image analyses of the hippocampus, and shown in FIG. 3, demonstrated the virtual elimination of dystrophic neurites in AN1792-treated mice (median 0.00%) compared to the PBS recipients (median 0.28%, p=0.0005).

Astrocytosis characteristic of plaque-associated inflammation was also absent in the brains of the Aβ1–42 injected group. The brains from the mice in the other groups contained abundant and clustered GFAP-positive astrocytes typical of Aβ plaque-associated gliosis. A subset of the GFAP-reacted slides were counter-stained with Thioflavin S to localize the Aβ deposits. The GFAP-positive astrocytes were associated with Aβ plaques in the SAP, PBS and untreated controls. No such association was found in the plaque-negative Aβ1–42 treated mice, while minimal plaque-associated gliosis was identified in one mouse treated with AN1792.

Figure 4:
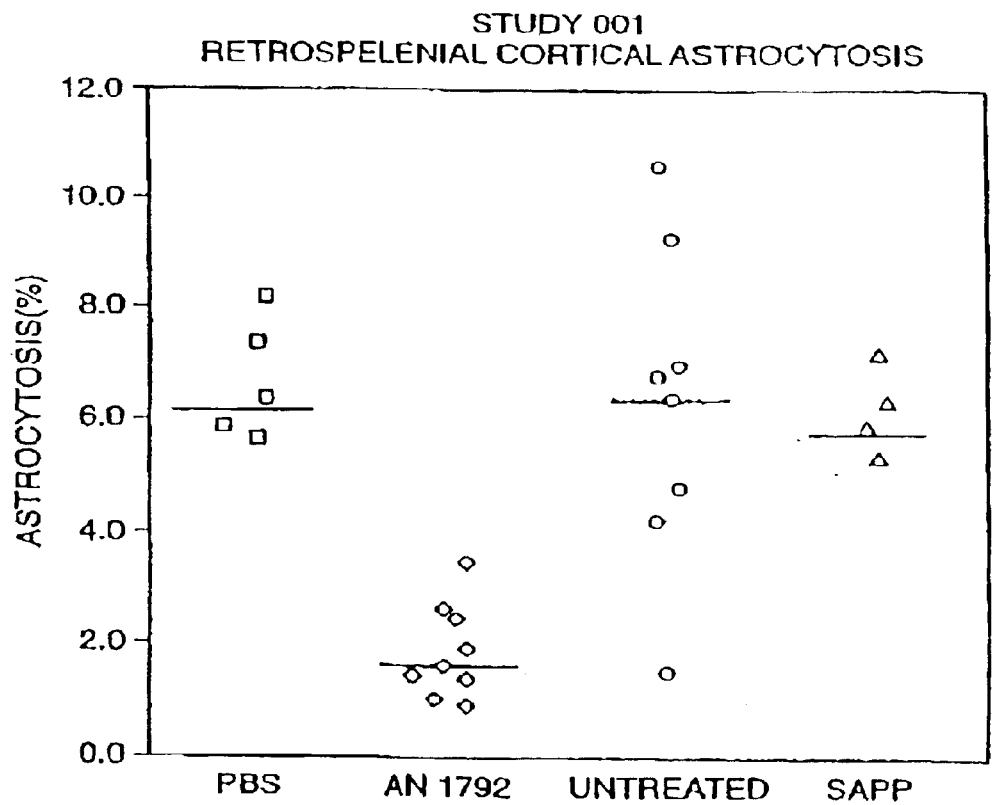
FIG. 4: Astrocytosis in the retrosplenial cortex. The percentage of the area of the cortical region occupied by glial fibrillary acidic protein (GFAP)-positive astrocytes was determined by quantitative computer-assisted image analysis of immunoreacted brain sections. The values for individual mice are shown sorted by treatment group and median group values are indicated by horizontal lines.

Image analyste, shown in FIG. 4 for the retrosplenial cortex, verified that the reduction in astrocytosis was significant with a median value of 1.56% for those treated with AN1792 versus median values greater than 6% for groups immunized with SAP peptides, PBS or untreated (p=0.0017).

Evidence from a subset of the Aβ1–42- and PBS-injected mice indicated plaque-associated MHC II immunoreactivity was absent in the Aβ1–42 injected mice, consistent with lack of an Aβ-related inflammatory response.

Sections of the mouse brains were also reacted with a mAb specific with a monoclonal antibody specific for MAC-1, a cell surface protein. MAC-1 (CD11b) is an integrin family member and exists as a heterodimer with CD18. The CD11b/CD18 complex is present on monocytes, macrophages, neutrophils and natural killer cells (Mak and Simard). The resident MAC-1-reactive cell type in the brain is likely to be microglia based on similar phenotypic morphology in MAC-1 immunoreacted sections. Plaque-associated MAC-1 labeling was lower in the brains of mice treated with AN1792 compared to the PBS control group, a finding consistent with the lack of an Aβ-induced inflammatory response.

C. Conclusion

The lack of Aβ plaques and reactive neuronal and gliotic changes in the brains of the Aβ1–42-injected mice indicate that no or extremely little amyloid was deposited in their brains, and pathological consequences, such as gliosis and neuritic pathology, were absent. PDAPP mice treated with Aβ1–42 show essentially the same lack of pathology as control nontransgenic mice. Therefore, Aβ1–42 injections are highly effective in the prevention of deposition or clearance of human Aβ from brain tissue, and elimination of subsequent neuronal and inflammatory degenerative changes. Thus, administration of Aβ peptide can have both preventative and therapeutic benefit in prevention of AD.

II. Dose Response Study

Groups of five-week old, female Swiss Webster mice (N=6 per group) were immunized with 300, 100, 33, 11, 3.7, 1.2, 0.4, or 0.13 ug of Aβ formulated in CFA/IFA administered intraperitoneally. Three doses were given at biweekly intervals followed by a fourth dose one month later. The first dose was emulsified with CFA and the remaining doses were emulsified with IFA. Animals were bled 4–7 days following each immunization starting after the second dose for measurement of antibody titers. Animals in a subset of three groups, those immunized with 11, 33, or 300 μg of antigen, were additionally bled at approximately monthly intervals for four months following the fourth immunization to monitor the decay of the antibody response across a range of doses of immunogenic formulations. These animals received a final fifth immunization at seven months after study initiation. They were sacrificed one week later to measure antibody responses to AN1792 and to perform toxicological analyses.

A declining dose response was observed from 300 to 3.7 μg with no response at the two lowest doses. Mean antibody titers are about 1:1000 after 3 doses and about 1:10,000 after 4 doses of 11–300 μg of antigen (see FIG. 5).

Antibody titers rose dramatically for all but the lowest dose group following the third immunization with increases in GMTs ranging from 5- to 25-fold. Low antibody responses were then detectable for even the 0.4 μg recipients. The 1.2 and 3.7 μg groups had comparable titers with GMTs of about 1000 and the highest four doses clustered together with GMTs of about 25,000, with the exception of the 33 μg dose group with a lower GMT of 3000. Following the fourth immunization, the titer increase was more modest for most groups. There was a clear dose response across the lower antigen dose groups from 0.14 μg to 11 μg ranging from no detectable antibody for recipients of 0.14 μg to a GMT of 36,000 for recipients of 11 μg. Again, titers for the four highest dose groups of 11 to 300 μg clustered together. Thus following two immunizations, the antibody titer was dependent on the antigen dose across the broad range from 0.4 to 300 μg. By the third immunization, titers of the highest four doses were all comparable and they remained at a plateau after an additional immunization.

Figure 6:
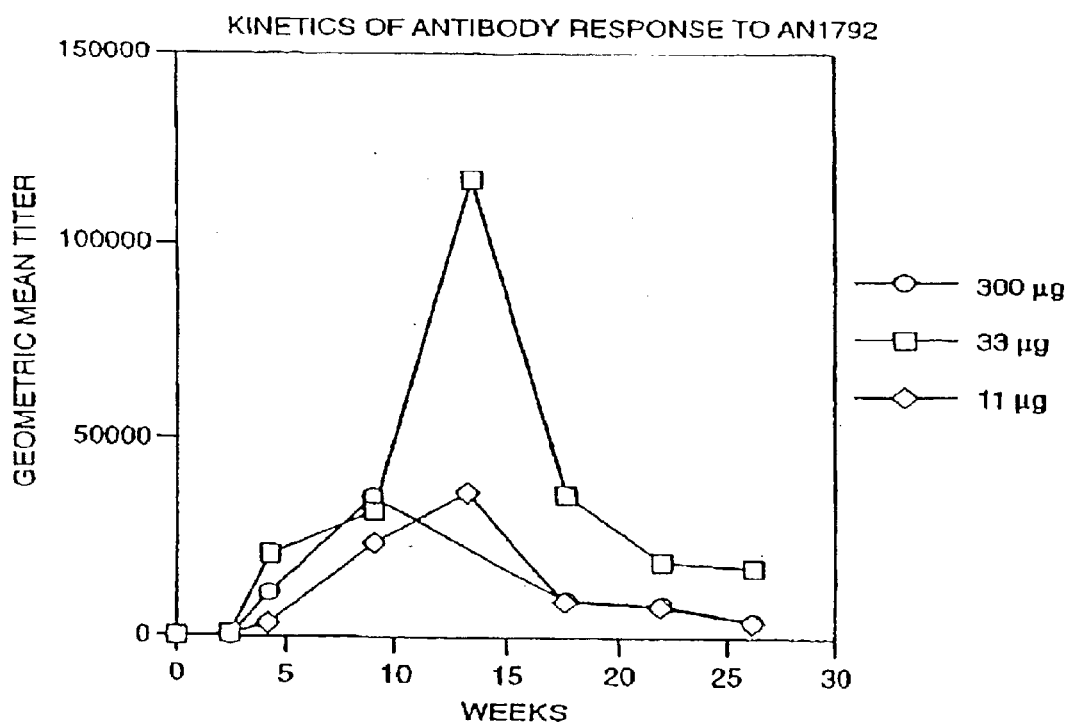
FIG. 6: Kinetics of antibody response to AN1792 immunization. Titers are expressed as geometric means of values for the 6 animals in each group.

One month following the fourth immunization, titers were 2- to 3-fold higher in the 300 μg group than those measured from blood drawn five days following the immunization (FIG. 6). This observation suggests that the peak anamnestic antibody response occurred later than 5 days post-immunization. A more modest (50%) increase was seen at this time in the 33 μg group. In the 300 μg dose group at two months following the last dose, GMTs declined steeply by about 70%. After another month, the decline was less steep at 45% (100 μg) and about 14% for the 33 and 11 μg doses. Thus, the rate of decline in circulating antibody titers following cessation of immunization appears to be biphasic with a steep decline the first month following peak response followed by a more modest rate of decrease thereafter.

The antibody titers and the kinetics of the response of these Swiss Webster mice are similar to those of young heterozygous PDAPP transgenic mice immunized in a parallel manner. Dosages effective to induce an immune response in humans are typically similar to dosages effective in mice.

III. Screen for Therapeutic Efficacy Against Established AD

This assay is designed to test immunogenic agents for activity in arresting or reversing neuropathologic characteristics of Aβ in aged animals. Immunizations with 42 amino acid long Aβ (AN1792) were begun at a time point when amyloid plaques are already present in the brains of the PDAPP mice.

Over the time course used in this study, untreated PDAPP mice develop a number of neurodegenerative changes that resemble those found in Aβ (Games et al., supra and Johnson-Wood et al., Proc. Natl. Acad. Sci. USA 94, 1550–1555 (1997)). The deposition of Aβ into amyloid plaques is associated with a degenerative neuronal response consisting of aberrant axonal and dendritic elements, called dystrophic neurites. Amyloid deposits that are surrounded by and contain dystrophic neurites called neuritic plaques. In both AD and the PDAPP mouse, dystrophic neurites have a distinctive globular structure, are immunoreactive with a panel of antibodies recognizing APP and cytoskeletal components, and display complex subcellular degenerative changes at the ultrastructural level. These characteristics allow for disease-relevant, selective and reproducible measurements of neuritic plaque formation in the PDAPP brains. The dystrophic neuronal component of PDAPP neuritic plaques is easily visualized with an antibody specific for human APP (monoclonal antibody 8E5), and is readily measurable by computer-assisted image analysis. Therefore, in addition to measuring the effects of AN1792 on amyloid plaque formation, we monitored the effects of this treatment on the development of neuritic dystrophy.

Astrocytes and microglia are non-neuronal cells that respond to and reflect the degree of neuronal injury. GFAP-positive astrocytes and MHC II-positive microglia are commonly observed in AD, and their activation increases with the severity of the disease. Therefore, we also monitored the development of reactive astrocytosis and microgliosis in the AN1792-treated mice.

A. Materials and Methods

Forty-eight, heterozygous female PDAPP mice, 11 to 11.5 months of age, obtained from Charles River, were randomly divided into two groups: 24 mice to be immunized with 100 μg of AN1792 and 24 mice to be immunized with PBS, each combined with Freund's adjuvant. The AN1792 and PBS groups were again divided when they reached ~15 months of age. At 15 months of age approximately half of each group of the AN1792- and PBS-treated animals were euthanized (n=10 and 9, respectively), the remainder continued to receive immunizations until termination at ~18 months (n=9 and 12, respectively). A total of 8 animals (5 AN1792, 3 PBS) died during the study. In addition to the immunized animals, one-year old (n=10), 15-month old (n=10) and 18-month old (n=10) untreated PDAPP mice were included for comparison in the ELISAs to measure Aβ and APP levels in the brain; the one-year old animals were also included in the immunohistochemical analyses.

Methodology was as in Example 1, unless otherwise indicated. US Peptides lot 12 and California Peptides lot ME0339 of AN1792 were used to prepare the antigen for the six immunizations administered prior to the 15-month time point. California Peptides lots ME0339 and ME0439 were used for the three additional immunizations administered between 15 and 18 months.

For immunizations, 100 µg of AN1792 in 200 µl PBS or PBS alone was emulsified 1:1 (vol:vol) with Complete Freund's adjuvant (CFA) or Incomplete Freund's adjuvant (IFA) or PBS in a final volume of 400 µl. The first immunization was delivered with CFA as adjuvant, the next four doses were given with IFA and the final four doses with PBS alone without added adjuvant. A total of nine immunizations were given over the seven-month period on a two-week schedule for the first three doses followed by a four-week interval for the remaining injections. The four-month treatment group, euthanized at 15 months of age, received only the first 6 immunizations.

B. Results

1. Effects of Aβ42 (AN1792) Treatment on Amyloid Burden

The results of AN1792 treatment on cortical amyloid burden determined by quantitative image analysis are shown in FIG. 7. The median value of cortical amyloid burden was 0.28% in a group of untreated 12-month old PDAPP mice, a value representative of the plaque load in mice at the study's initiation. At 18 months, the amyloid burden increased over 17-fold to 4.87% in PBS-treated mice, while AN1792-treated mice had a greatly reduced amyloid burden of only 0.01%, notably less than the 12-month untreated and both the 15- and 18-month PBS-treated groups. The amyloid burden was significantly reduced in the AN1792 recipients at both 15 (96% reduction; p=0.003) and 18 (>99% reduction; p=0.0002) months.

Typically, cortical amyloid deposition in PDAPP mice initiates in the frontal and retrosplenial cortices (RSC) and progresses in a ventral-lateral direction to involve the temporal and entorhinal cortices (EC). Little or no amyloid was found in the EC of 12 month-old mice, the approximate age at which AN1792 was first administered. After 4 months of AN1792 treatment, amyloid deposition was greatly diminished in the RSC, and the progressive involvement of the EC was entirely eliminated by AN1792 treatment. The latter observation showed that AN1792 completely halted the progression of amyloid that would normally invade the temporal and ventral cortices, as well as arrested or possibly reversed deposition in the RSC.

The profound effects of AN1792 treatment on developing cortical amyloid burden in the PDAPP mice are further demonstrated by the 18-month group, which had been treated for seven months. A near complete absence of cortical amyloid was found in the AN1792-treated mouse, with a total lack of diffuse plaques, as well as a reduction in compacted deposits.

2. Aβ42 (AN1792) Treatment-associated Cellular and Morphological Changes

A population of Aβ-positive cells was found in brain regions that typically contain amyloid deposits. Remarkably, in several brains from AN1792 recipients, very few or no extracellular cortical amyloid plaques were found. Most of the Aβ immunoreactivity appeared to be contained within cells with large lobular or clumped soma. Phenotypically, these cells resembled activated microglia or monocytes. They were immunoreactive with antibodies recognizing ligands expressed by activated monocytes and microglia (MHC II and CD11b) and were occasionally associated with the wall or lumen of blood vessels. Comparison of near-adjacent sections labeled with Aβ and MHC II-specific antibodies revealed that similar patterns of these cells were recognized by both classes of antibodies. Detailed examination of the AN1792-treated brains revealed that the MHC II-positive cells were restricted to the vicinity of the limited amyloid remaining in these animals. Under the fixation conditions employed, the cells were not immunoreactive with antibodies that recognize T cell (CD3, CD3e) or B cell (CD45RA, CD45RB) ligands or leukocyte common antigen (CD45), but were reactive with an antibody recognizing leukosialin (CD43) which cross-reacts with monocytes. No such cells were found in any of the PBS-treated mice.

PDAPP mice invariably develop heavy amyloid deposition in the outer molecular layer of the hippocampal dentate gyrus. The deposition forms a distinct streak within the perforant pathway, a subregion that classically contains amyloid plaques in AD. The characteristic appearance of these deposits in PBS-treated mice resembled that previously characterized in untreated PDAPP mice. The amyloid deposition consisted of both diffuse and compacted plaques in a continuous band. In contrast, in a number of brains from AN1792-treated mice this pattern was drastically altered. The hippocampal amyloid deposition no longer contained diffuse amyloid, and the banded pattern was completely disrupted. Instead, a number of unusual punctate structures were present that are reactive with anti-Aβ antibodies, several of which appeared to be amyloid-containing cells.

MHC II-positive cells were frequently observed in the vicinity of extracellular amyloid in AN1792-treated animals. The pattern of association of Aβ-positive cells with amyloid was very similar in several brains from AN1792-treated mice. The distribution of these monocytic cells was restricted to the proximity of the deposited amyloid and was entirely absent from other brain regions devoid of Aβ plaques.

Quantitative image analysis of MHC II and MAC I-labeled sections revealed a trend towards increased immunoreactivity in the RSC and hippocampus of AN1792-treated mice compared to the PBS group which reached significance with the measure of MAC 1 reactivity in hippocampus.

These results are indicative of active, cell-mediated removal of amyloid in plaque-bearing brain regions.

3. AN1792 Effects on Aβ Levels: ELISA Determinations (a) Cortical Levels

In untreated PDAPP mice, the median level of total Aβ in the cortex at 12 months was 1,600 ng/g, which increased to 8,700 ng/g by 15 months (Table 4). At 18 months the value was 22,000 ng/g, an increase of over 10-fold during the time course of the experiment. PBS-treated animals had 8,600 ng/g total Aβ at 15 months which increased to 19,000 ng/g at 18 months. In contrast, AN1792-treated animals had 81% less total Aβ at 15 months (1,600 ng/g) than the PBS-immunized group. Significantly less (p=0.0001) total Aβ (5,200 ng/g) was found at 18 months when the AN1792 and PBS groups were compared (Table 4), representing a 72% reduction in the Aβ that would otherwise be present. Similar results were obtained when cortical levels of Aβ42 were compared, namely that the AN1792-treated group contained much less Aβ42, but in this case the differences between the AN1792 and PBS groups were significant at both 15 months (p=0.04) and 18 months (p=0.0001, Table 4).

TABLE 4

Median Aβ Levels (ng/g) in Cortex

| Age | UNTREATED | | | PBS | | | AN1792 | | |
|---|---|---|---|---|---|---|---|---|---|
| | Total | Aβ42 | (n) | Total | Aβ42 | (n) | Total | Aβ42 | (n) |
| 12 | 1,600 | 1,300 | (10) | | | | | | |
| 15 | 8,700 | 8,300 | (10) | 8,600 | 7,200 | (9) | 1,600 | 1,300* | (10) |
| 18 | 22,200 | 18,500 | (10) | 19,000 | 15,900 | (12) | 5,200** | 4,000** | (9) |

*p = 0.0412
**p = 0.0001

(b) Hippocampal Levels

In untreated PDAPP mice, median hippocampal levels of total Aβ at twelve months of age were 15,000 ng/g which increased to 51,000 ng/g at 15 months and further to 81,000 ng/g at 18 months (Table 5). Similarly, PBS immunized mice showed values of 40,000 ng/g and 65,000 ng/g at 15 months and 18 months, respectively. AN1792 immunized animals exhibited less total Aβ, specifically 25,000 ng/g and 51,000 ng/g at the respective 15-month and 18-month timepoints. The 18-month AN1792-treated group value was significantly lower than that of the PBS treated group (p=0.0105; Table 5). Measurement of Aβ42 gave the same pattern of results, namely that levels in the AN1792-treated group were significantly lower than in the PBS group (39,000 ng/g vs. 57,000 ng/g, respectively; p=0.002) at the 18-month evaluation (Table 3).

4. Effects of AN1792 Treatment on APP Levels

APP-α and the full-length APP molecule both contain all or part of the Aβ sequence and thus could be potentially impacted by the generation of an AN1792-directed immune response. In studies to date, a slight increase in APP levels has been noted as neuropathology increases in the PDAPP mouse. In the cortex, levels of either APP-α/FL (full length) or APP-α were essentially unchanged by treatment with the exception that APP-α was reduced by 19% at the 18-month timepoint in the AN1792-treated vs. the PBS-treated group. The 18-month AN1792-treated APP values were not significantly different from values of the 12-month and 15-month untreated and 15-month PBS groups. In all cases the APP values remained within the ranges that are normally found in PDAPP mice.

TABLE 5

Median Aβ Levels (ng/g) in Hippocampus

| Age | UNTREATED | | | PBS | | | AN1792 | | |
|---|---|---|---|---|---|---|---|---|---|
| | Total | Aβ42 | (n) | Total | Aβ42 | (n) | Total | Aβ42 | (n) |
| 12 | 15,500 | 11,100 | (10) | | | | | | |
| 15 | 51,500 | 44,400 | (10) | 40,100 | 35,70 | (9) | 24,50 | 22,100 | (10) |
| 18 | 80,800 | 64,200 | (10) | 65,400 | 57,10 | (12) | 50,90 | 38,900** | (9) |

*p = 0.0105
**p = 0.0022

(c) Cerebellar Levels

In 12-month untreated PDAPP mice, the median cerebellar level of total AP was 15 ng/g (Table 6). At 15 months, this median increased to 28 ng/g and by 18 months had risen to 35 ng/g. PBS-treated animals displayed median total Aβ values of 21 ng/g at 15 months and 43 ng/g at 18 months. AN1792-treated animals were found to have 22 ng/g total Aβ at 15 months and significantly less p=0.002) total Aβ at 18 months (25 ng/g) than the corresponding PBS group (Table 6).

TABLE 6

Median Aβ Levels (ng/g) in Cerebellum

| Age | UNTREATED | | PBS | | AN1792 | |
|---|---|---|---|---|---|---|
| | Total Aβ | (n) | Total Aβ | (n) | Total Aβ | (n) |
| 12 | 15.6 | (10) | | | | |
| 15 | 27.7 | (10) | 20.8 | (9) | 21.7 | (10) |
| 18 | 35.0 | (10) | 43.1 | (12) | 24.8* | (9) |

*p = 0.0018

5. Effects of AN1792 Treatment on Neurodegenerative and Gliotic Pathology

Figure 8:
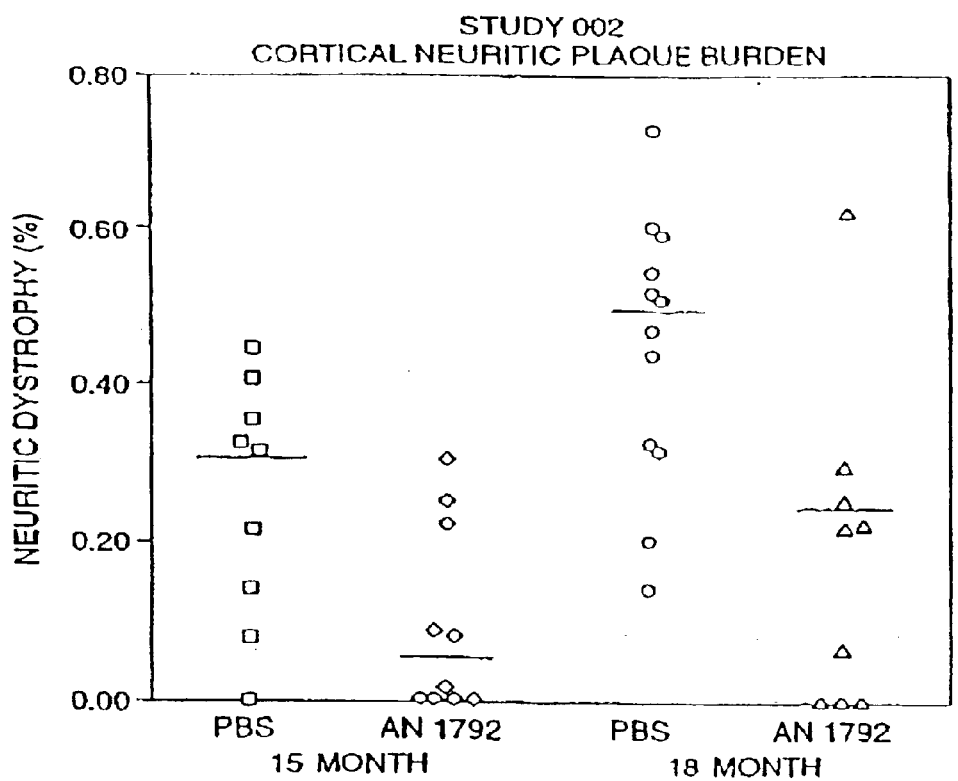
FIG. 8: Quantitative image analysis of the neuritic plaque burden in PBS-and AN1792-treated mice.

Neuritic plaque burden was significantly reduced in the frontal cortex of AN1792-treated mice compared to the PBS group at both 15 (84%; p=0.03) and 18 (55%; p=0.01) months of age (FIG. 8). The median value of the neuritic plaque burden increased from 0.32% to 0.49% in the PBS group between 15 and 18 months of age. This contrasted with the greatly reduced development of neuritic plaques in the AN1792 group, with median neuritic plaque burden values of 0.05% and 0.22%, in the 15 and 18 month groups, respectively.

Figure 9:
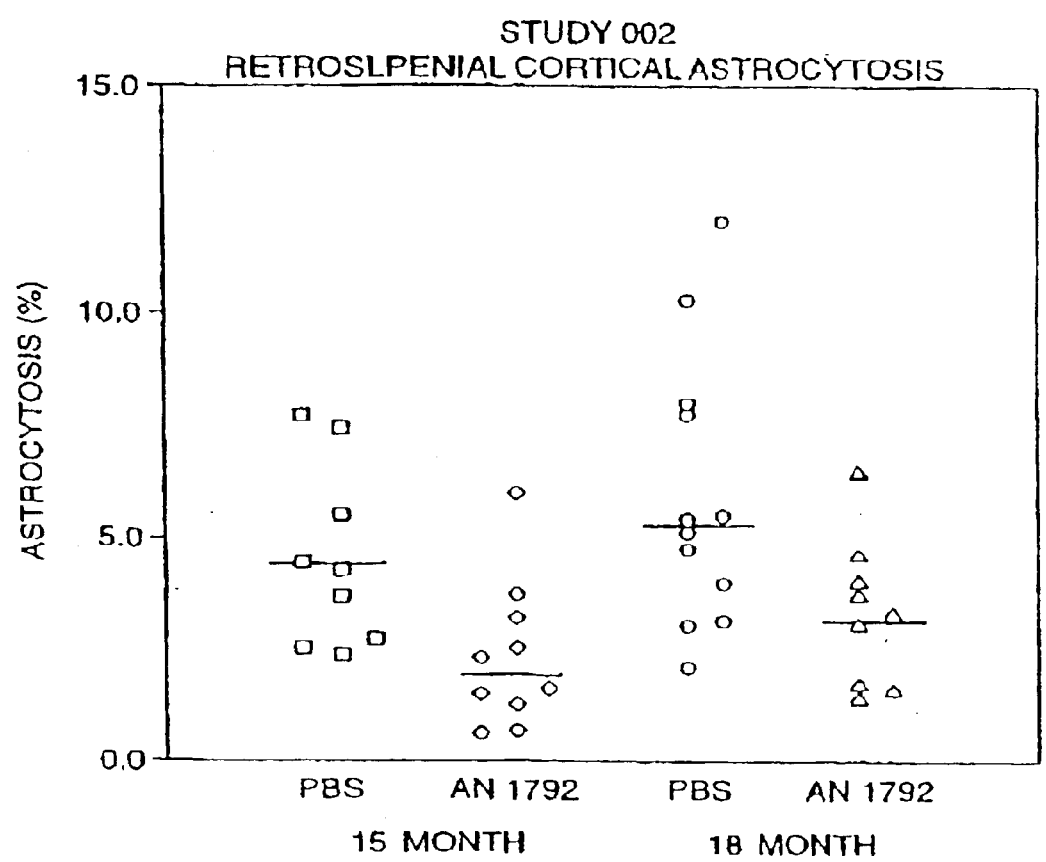
FIG. 9: Quantitative image analysis of the percent of the retrosplenial cortex occupied by astrocytosis in PBS- and AN1792-treated mice.

Immunizations with AN1792 seemed well tolerated and reactive astrocytosis was also significantly reduced in the RSC of AN1792-treated mice when compared to the PBS group at both 15 (56%; p=0.011) and 18 (39%; p=0.028) months of age (FIG. 9). Median values of the percent of astrocytosis in the PBS group increased between 15 and 18 months from 4.26% to 5.21%. AN1792-treatment suppressed the development of astrocytosis at both time points to 1.89% and 3.2%, respectively. This suggests the neuropil was not being damaged by the clearance process.

6. Antibody Responses

As described above, eleven-month old, heterozygous PDAPP mice (N=24) received a series of 5 immunizations of 100 μg of AN1792 emulsified with Freund's adjuvant and administered intraperitoneally at weeks 0, 2, 4, 8, and 12, and a sixth immunization with PBS alone (no Freund's adjuvant) at week 16. As a negative control, a parallel set of 24 age-matched transgenic mice received immunizations of PBS emulsified with the same adjuvants and delivered on the same schedule. Animals were bled within three to seven days following each immunization starting after the second dose. Antibody responses to AN1792 were measured by ELISA. Geometric mean titers (GMT) for the animals that were immunized with AN1792 were approximately 1,900, 7,600, and 45,000 following the second, third and last (sixth) doses respectively. No Aβ-specific antibody was measured in control animals following the sixth immunization.

Approximately one-half of the animals were treated for an additional three months, receiving immunizations at about 20, 24 and 27 weeks. Each of these doses was delivered in PBS vehicle alone without Freund's adjuvant. Mean antibody titers remained unchanged over this time period. In fact, antibody titers appeared to remain stable from the fourth to the eighth bleed corresponding to a period covering the fifth to the ninth injections.

To determine if the Aβ-specific antibodies elicited by immunization that were detected in the sera of AN1792-treated mice were also associated with deposited brain amyloid, a subset of sections from the AN1792- and PBS-treated mice were reacted with an antibody specific for mouse IgG. In contrast to the PBS group, Aβ plaques in AN1792-treated brains were coated with endogenous IgG. This difference between the two groups was seen in both 15- and 18-month groups. Particularly striking was the lack of labeling in the PBS group, despite the presence of a heavy amyloid burden in these mice. These results show that immunization with a synthetic Aβ protein generates antibodies that recognize and bind in vivo to the Aβ in amyloid plaques.

7. Cellular-mediated Immune Responses

Figure 10:
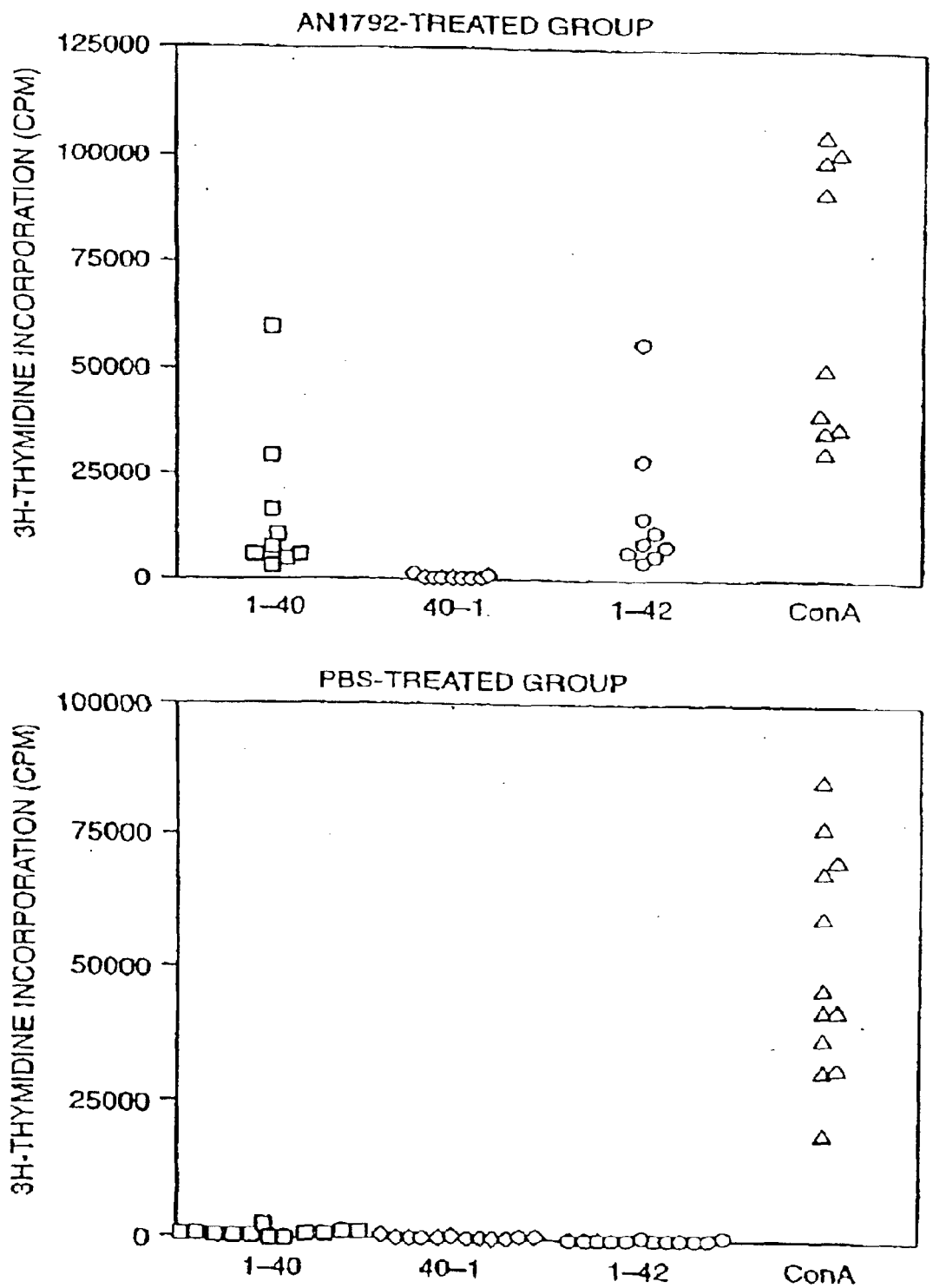
FIG. 10: Lymphocyte Proliferation Assay on spleen cells from AN1792-treated (upper panel) or PBS-treated (lower panel) mice.

Spleens were removed from nine AN1792-immunized and 12 PBS-immunized 18-month old PDAPP mice 7 days after the ninth immunization. Splenocytes were isolated and cultured for 72 h in the presence of Aβ40, Aβ42, or Aβ40–1 (reverse order protein). The mitogen Con A served as a positive control. Optimum responses were obtained with >1.7 μM protein. Cells from all nine AN1792-treated animals proliferated in response to either Aβ1–40 or Aβ1–42 protein, with equal levels of incorporation for both proteins (FIG. 10, Upper Panel). There was no response to the Aβ40–1 reverse protein. Cells from control animals did not respond to any of the Aβ proteins (FIG. 10, Lower Panel).

C. Conclusion

The results of this study show that AN1792 immunization of PDAPP mice possessing existing amyloid deposits slows and prevents progressive amyloid deposition and retard consequential neuropathologic changes in the aged PDAPP mouse brain. Immunizations with AN1792 essentially halted amyloid developing in structures that would normally succumb to amyloidosis. Thus, administration of Aβ peptide has therapeutic benefit in the treatment of Aβ.

IV. Screen of Aβ Fragments

100 PDAPP mice age 9–11 months were immunized with 9 different regions of APP and Aβ to determine which epitopes convey the efficacious response. The 9 different immunogens and one control are injected i.p. as described above. The immunogens include four human Aβ peptide conjugates 1–12, 13–28, 32–42, 1–5, all coupled to sheep anti-mouse IgG via a cystine link; an APP polypeptide amino acids 592–695, aggregated human Aβ1–40, and aggregated human Aβ25–35, and aggregated rodent Aβ42. Aggregated Aβ42 and PBS were used as positive and negative controls, respectively. Ten mice were used per treatment group. Titers were monitored as above and mice were euthanized at the end of 4 months of injections. Histochemistry, Aβ levels, and toxicology analysis was determined post mortem.

A. Materials and Methods

1. Preparation of Immunogens Preparation of coupled Aβ peptides: four human Aβ peptide conjugates (amino acid residues 1–5, 1–12, 13–28, and 33–42, each conjugated to sheep anti-mouse IgG) were prepared by coupling through an artificial cysteine added to the Aβ peptide using the crosslinking reagent sulfo-EMCS. The Aβ peptide derivatives were synthesized with the following final amino acid sequences. In each case, the location of the inserted cysteine residue is indicated by underlining. The Aβ13–28 peptide derivative also had two glycine residues added prior to the carboxyl terminal cysteine as indicated.

| | |
|---|---|
| Aβ1–12 peptide | NH2-DAEFRHDSGYEVC-COOH (SEQ ID NO: 30) |
| Aβ1–5 peptide | NH2-DAEFRC-COOH (SEQ ID NO: 31) |
| Aβ33–42 peptide | NH2-C-amino-heptanoic acid-GLMVGGVVIA-COOH (SEQ ID NO: 32) |
| Aβ13–28 peptide | Ac-NH-HHQKLVFFAEDVGSNKGGC-COOH (SEQ ID NO: 33) |

To prepare for the coupling reaction, ten mg of sheep anti-mouse IgG (Jackson ImmunoRescarch Laboratories) was dialyzed overnight against 10 mM sodium borate buffer, pH 8.5. The dialyzed antibody was then concentrated to a volume of 2 mL using an Amicon Centriprep tube. Ten mg sulfo-EMCS.

[N (γ-maleimidocuproyloxy)succinimide] (Molecular Sciences Co.) was dissolved in one mL deionized water. A 40-fold molar excess of sulfo-EMCS was added dropwise with stirring to the sheep anti-mouse IgG and then the solution was stirred for an additional ten min. The activated sheep anti-mouse IgG was purified and buffer exchanged by passage over a 10 mL gel filtration column (Pierce Presto Column, obtained from Pierce Chemicals) equilibrated with 0.1 M NaPO4, 5 mM EDTA, pH 6.5. Antibody containing fractions, identified by absorbance at 280 nm, were pooled and diluted to a concentration of approximately 1 mg/mL, using 1.4 mg per OD as the extinction coefficient. A 40-fold molar excess of Aβ peptide was dissolved in 20 mL of 10 mM NaPO4, pH 8.0, with the exception of the Aβ33–42 peptide for which 10 mg was first dissolved in 0.5 mL of DMSO and then diluted to 20 mL with the 10 mM NaPO4 buffer. The peptide solutions were each added to 10 mL of activated sheep anti-mouse IgG and rocked at room temperature for 4 hr. The resulting conjugates were concentrated to a final volume of less than 10 mL using an Amicon Centriprep tube and then dialyzed against PBS to buffer exchange the buffer and remove free peptide. The conjugates were passed through 0.22 μm-pore size filters for sterilization and then aliquoted into fractions of 1 mg and stored frozen at −20° C. The concentrations of the conjugates were determined using the BCA protein assay (Pierce Chemicals) with horse IgG for the standard curve. Conjugation was documented by the molecular weight increase of the conjugated peptides relative to that of the activated sheep anti-mouse IgG. The Aβ1–5 sheep anti-mouse conjugate was a pool of two conjugations, the rest were from a single preparation.

2. Preparation of Aggregated Aβ Peptides

Human 1–40 (AN1528; California Peptides Inc., Lot ME0541), human 1–42 (AN1792; California Peptides Inc., Lots ME0339 and ME0439), human 25–35, and rodent 1–42 (California Peptides Inc., Lot ME0218) peptides were freshly solubilized for the preparation of each set of injections from lyophilized powders that had been stored desiccated at −20° C. For this purpose, two mg of peptide were added to 0.9 ml of deionized water and the mixture was vortexed to generate a relatively uniform solution or suspension. Of the four, AN1528 was the only peptide soluble at this step. A 100 μl aliquot of 10×PBS (1×PBS: 0.15 M NaCl, 0.01 M sodium phosphate, pH 7.5) was then added at which point AN1528 began to precipitate. The suspension was vortexed again and incubated overnight at 37° C. for use the next day.

Preparation of the pBx6 protein: An expression plasmid encoding pBx6, a fusion protein consisting of the 100-amino acid bacteriophage MS-2 polymerase N-terminal leader sequence followed by amino acids 592–695 of APP (βAPP) was constructed as described by Oltersdorf et al., J. Biol. Chem. 265, 4492–4497 (1990). The plasmid was transfected into E. coli and the protein was expressed after induction of the promoter. The bacteria were lysed in 8M urea and pBx6 was partially purified by preparative SDS PAGE. Fractions containing pBx6 were identified by Western blot using a rabbit anti-pBx6 polyclonal antibody, pooled, concentrated using an Amicon Centriprep tube and dialysed against PBS. The purity of the preparation, estimated by Coomassie Blue stained SDS PAGE, was approximately 5 to 10%.

B. Results and Discussion

1. Study Design

One hundred male and female, nine- to eleven-month old heterozygous PDAPP transgenic mice were obtained from Charles River Laboratory and Taconic Laboratory. The mice were sorted into ten groups to be immunized with different regions of Aβ or APP combined with Freund's adjuvant. Animals were distributed to match the gender, age, parentage and source of the animals within the groups as closely as possible. The immunogens included four Aβ peptides derived from the human sequence, 1–5, 1–12, 13–28, and 33–42, each conjugated to sheep anti-mouse IgG; four aggregated Aβ peptides, human 1–40 (AN1528), human 1–42 (AN1792), human 25–35, and rodent 1–42; and a fusion polypeptide, designated as pBx6, containing APP amino acid residues 592–695. A tenth group was immunized with PBS combined with adjuvant as a control.

For each immunization, 100 μg of each Aβ peptide in 200 μl PBS or 200 μg of the APP derivative pBx6 in the same volume of PBS or PBS alone was emulsified 1:1 (vol:vol) with Complete Freund's adjuvant (CFA) in a final volume of 400 μl for the first immunization, followed by a boost of the same amount of immunogen in Incomplete Freund's adjuvant (IFA) for the subsequent four doses and with PBS for the final dose. Immunizations were delivered intrapentioneally on a biweekly schedule for the first three doses, then on a monthly schedule thereafter. Animals were bled four to seven days following each immunization starting after the second dose for the measurement of antibody titers. Animals were euthanized approximately one week after the final dose.

2. Aβ and APP Levels in the Brain

Following about four months of immunization with the various Aβ peptides or the APP derivative, brains were removed from saline-perfused animals. One hemisphere was prepared for immunohistochemical analysis and the second was used for the quantitation of Aβ and APP levels. To measure the concentrations of various forms of beta amyloid peptide and amyloid precursor protein, the hemisphere was dissected and homogenates of the hippocampal, cortical, and cerebellar regions were prepared in 5 M guanidine. These were diluted and the level of amyloid or APP was quantitated by comparison to a series of dilutions of standards of Aβ peptide or APP of kenown concentrations in an ELISA format.

The median concentration of total Aβ for the control group immunized with PBS was 5.8-fold higher in the hippocampus than in the cortex (median of 24,318 ng/g hippocampal tissue compared to 4,221 ng/g for the cortex). The median level in the cerebellum of the control group (23.4 ng/g tissue) was about 1,000-fold lower than in the hippocampus. These levels are similar to those that we have previously reported for heterozygous PDAPP transgenic mice of this age (Johnson-Woods et al., 1997, supra).

Figure 11:
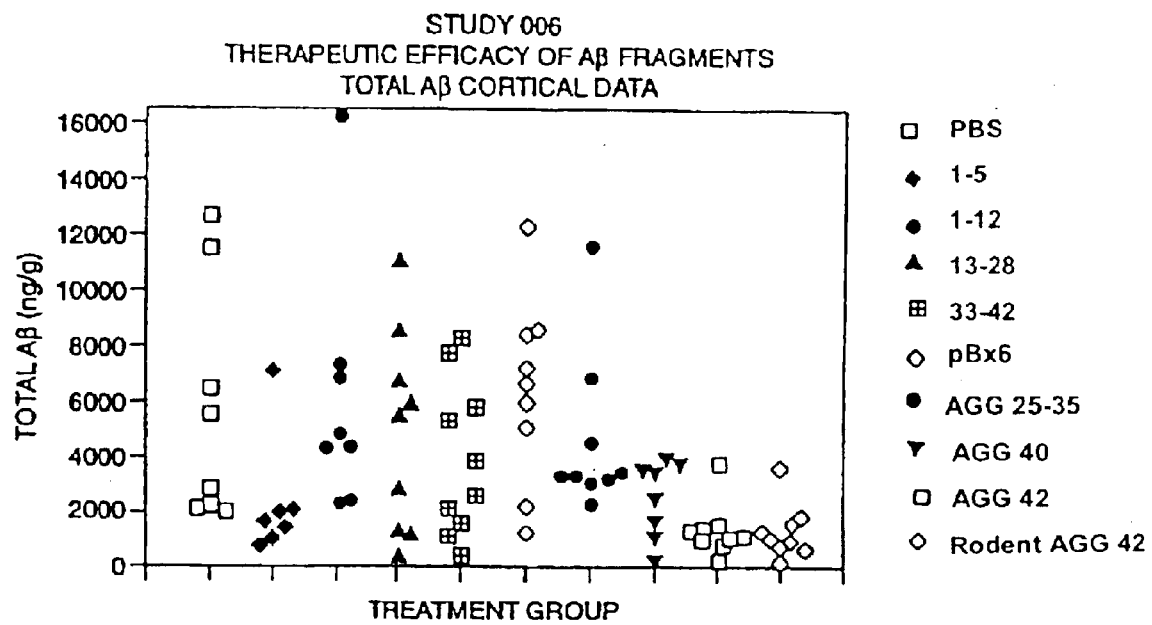
FIG. 11: Total Aβ levels in the cerebral cortex. A scatterplot of individual Aβ profiles in mice immunized with Aβ or APP derivatives combined with Freund's adjuvant.

For the cortex, a subset of treatment groups had median total Aβ and Aβ1–42 levels which differed significantly from those of the control group (p<0.05), those animals receiving AN1792, rodent Aβ1–42 or the Aβ1–5 peptide conjugate as shown in FIG. 11. The median levels of total Aβ were reduced by 75%, 79% and 61%, respectively, compared to the control for these three treatment groups. There were no discemable correlations between Aβ-specific antibody titers and Aβ levels in the cortical region of the brain for any of the groups.

In the hippocampus, the median reduction of total Aβ associated with AN1792 treatment (46%, p=0.0543) was not as great as that observed in the cortex (75%, p=0.0021). However, the magnitude of the reduction was far greater in the hippocampus than in the cortex, a net reduction of 11,186 ng/g tissue in the hippocampus versus 3,171 ng/g tissue in the cortex. For groups of animals receiving rodent Aβ1–42 or Aβ1–5, the median total Aβ levels were reduced by 36% and 26%, respectively. However, given the small group sizes and the high variability of the amyloid peptide levels from animal to animal within both groups, these reductions were not significant. When the levels of Aβ1–42 were measured in the hippocampus, none of the treatment-induced reductions reached significance. Thus, due to the smaller Aβ burden in the cortex, changes in this region are a more sensitive indicator of treatment effects. The changes in Aβ levels measured by ELISA in the cortex are similar, but not identical, to the results from the immunohistochemical analysis (see below).

Total Aβ was also measured in the cerebellum, a region typically minimally affected with Aβ pathology. None of the median Aβ concentrations of any of the groups immunized with the various Aβ peptides or the APP derivative differed from that of the control group in this region of the brain. This result suggests that non-pathological levels of Aβ are unaffected by treatment.

APP concentration was also determined by ELISA in the cortex and cerebellum from treated and control mice. Two different APP assays were utilized. The first, designated APP-α/FL, recognizes both APP-alpha (α, the secreted form of APP which has been cleaved within the Aβ sequence), and full-length forms (FL) of APP, while the second recognizes only APP-α. In contrast to the treatment-associated diminution of Aβ in a subset of treatment groups, the levels of APP were unchanged in all of the treated compared to the control animals. These results indicate that the immunizations with Aβ peptides are not depleting APP, rather the treatment effect is specific to Aβ.

In summary, total Aβ and Aβ1–42 levels were significantly reduced in the cortex by treatment with AN1792, rodent Aβ1–42 or Aβ1–5 conjugate. In the hippocampus, total Aβ was significantly reduced only by AN1792 treatment. No other treatment-associated changes in Aβ or APP levels in the hippocampal, cortical or cerebellar regions were significant.

2. Histochemical Analyses

Figure 12:
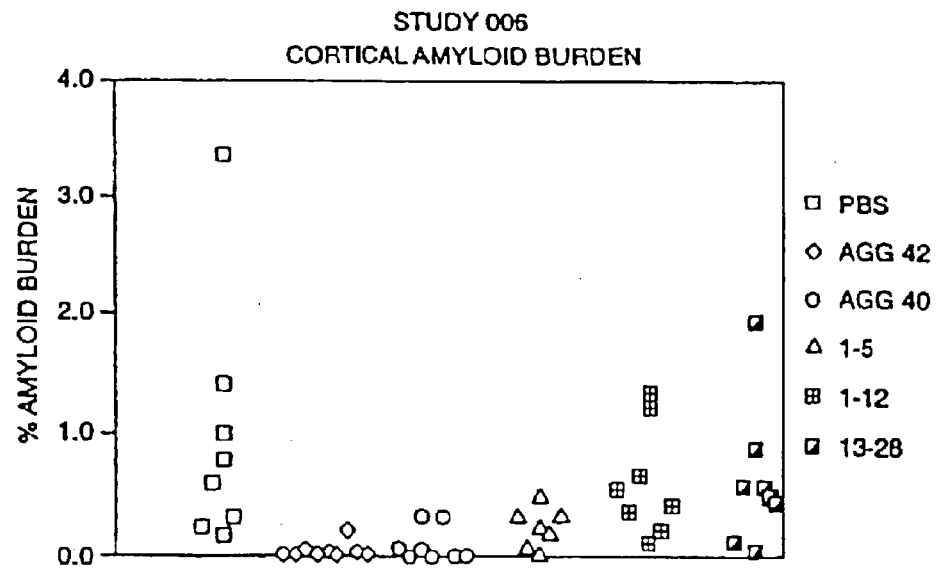
FIG. 12: Amyloid burden in the cortex, determined by quantitative image analysis of immunoreacted brain sections for mice immunized with the Aβ peptide conjugates Aβ1–5, Aβ1–12, and Aβ13–28; the full length Aβ aggregates Aβ42 ("AN1792") and Aβ1–40 ("AN1528") and the PBS-treated control group.

Brains from a subset of six groups were prepared for immunohistochemical analysis, three groups immunized with the Aβ peptide conjugates Aβ1–5, Aβ1–12, and Aβ13–28; two groups immunized with the full length Aβ aggregates AN1792 and AN1528 and the PBS-treated control group. The results of image analyses of the amyloid burden in brain sections from these groups are shown in FIG. 12. There were significant reductions of amyloid burden in the cortical regions of three of the treatment groups versus control animals. The greatest reduction of amyloid burden was observed in the group receiving AN1792 where the mean value was reduced by 97% (p=0.001). Significant reductions were also observed for those animals treated with AN1528 (95%, p=0.005) and the Aβ1–5 peptide conjugate (67%, p=0.02).

The results obtained by quantitation of total Aβ or Aβ1–42 by ELISA and amyloid burden by image analysis differ to some extent. Treatment with AN1528 had a significant impact on the level of cortical amyloid burden when measured by quantitative image analysis but not on the concentration of total Aβ in the same region when measured by ELISA. The difference between these two results is likely to be due to the specificities of the assays. Image analysis measures only insoluble Aβ aggregated into plaques. In contrast, the ELISA measures all forms of Aβ, both soluble and insoluble, monomeric and aggregated. Since the disease pathology is thought to be associated with the insoluble plaque-associated form of Aβ, the image analysis technique may have more sensitivity to reveal treatment effects. However since the ELISA is a more rapid and easier assay, it is very useful for screening purposes. Moreover it may reveal that the treatment-associated reduction of Aβ is greater for plaque-associated than total Aβ.

To determine if the Aβ-specific antibodies elicited by immunization in the treated animals reacted with deposited brain amyloid, a subset of the sections from the treated animals and the control mice were reacted with an antibody specific for mouse IgG. In contrast to the PBS group, Aβ-containing plaques were coated with endogenous IgG for animals immunized with the Aβ peptide conjugates Aβ1–5, Aβ1–12, and Aβ13–28; and the full length Aβ aggregates AN1792 and AN1528. Brains from animals immunized with the other Aβ peptides or the APP peptide pBx6 were not analyzed by this assay.

3. Measurement of Antibody Titers

Figure 13:
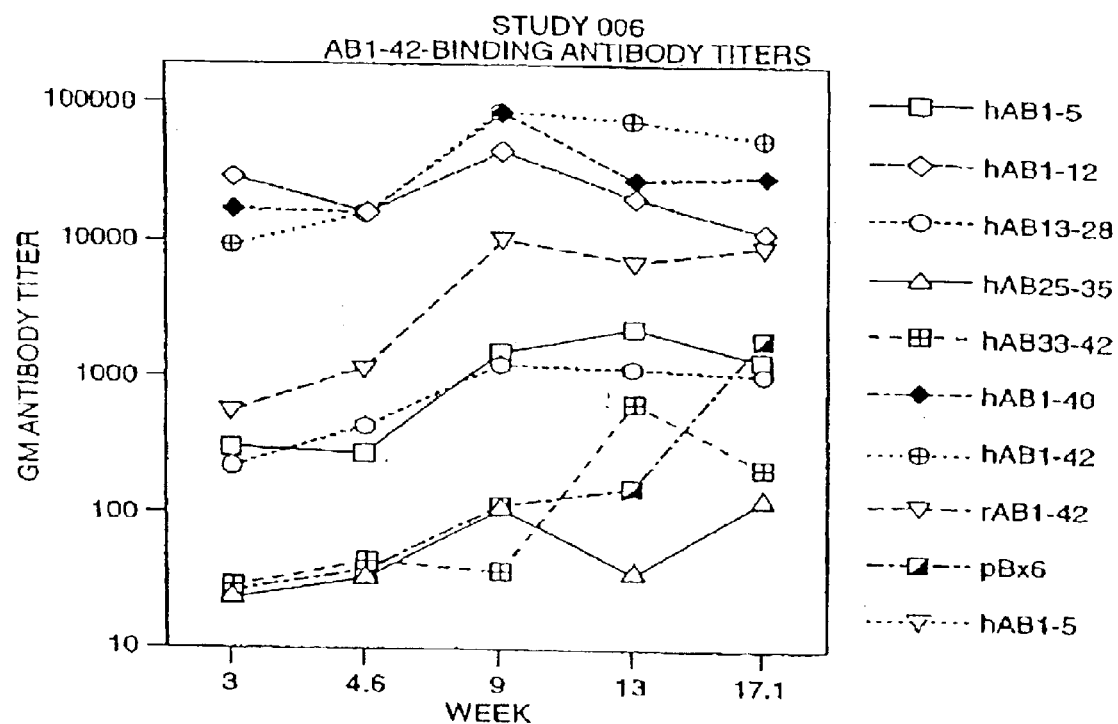
FIG. 13: Geometric mean titers of Aβ-specific antibody for groups of mice immunized with Aβ or APP derivatives combined with Freund's adjuvant.

Mice were bled four to seven days following each immunization starting after the second immunization, for a total of five bleeds. Antibody titers were measured as Aβ1–42-binding antibody using a sandwich ELISA with plastic multi-well plates coated with Aβ1–42. As shown in FIG. 13, peak antibody titers were elicited following the fourth dose for those four immunization formulations which elicited the highest titers of AN1792-specific antibodies: AN1792 (peak GMT: 94,647), AN1528 (peak GMT: 88,231), Aβ1–12 conjugate (peak GMT: 47,216) and rodent Aβ1–42 (peak GMT: 10,766). Titers for these groups declined somewhat following the fifth and sixth doses. For the remaining five immunogens, peak titers were reached following the fifth or the sixth dose and these were of much lower magnitude than those of the four highest titer groups: Aβ1–5 conjugate (peak GMT: 2,356), pBx6 (peak GMT: 1,986), Aβ13–28 conjugate (peak GMT: 1,183), Aβ33–42 conjugate (peak GMT: 658), Aβ25–35 (peak GMT: 125). Antibody titers were also measured against the homologous peptides using the same ELISA sandwich format for a subset of the immunogens, those groups immunized with Aβ1–5, Aβ13–28, Aβ25–35, Aβ33–42 or rodent Aβ1–42. These titers were about the same as those measured against Aβ1–42 except for the rodent Aβ1–42 immunogen in which case antibody titers against the homologous immunogen were about two-fold higher. The magnitude of the AN1792-specific antibody titer of individual animals or the mean values of treatment groups did not correlate with efficacy measured as the reduction of Aβ in the cortex.

4. Lymphoproliferative Responses

Aβ-dependent lymphoproliferation was measured using spleen cells harvested approximately one week following the final, sixth, immunization. Freshly harvested cells, 105 per well, were cultured for 5 days in the presence of Aβ1–40 at a concentration of 5 μM for stimulation. Cells from a subset of seven of the ten groups were also cultured in the presence of the reverse peptide, Aβ40–1. As a positive control, additional cells were cultured with the T cell mitogen, PHA, and, as a negative control, cells were cultured without added peptide.

Lymphocytes from a majority of the animals proliferated in response to PHA. There were no significant responses to the Aβ40–1 reverse peptide. Cells from animals immunized with the larger aggregated Aβ peptides, AN1792, rodent Aβ1–42 and AN1528 proliferated robustly when stimulated with Aβ1–40 with the highest cpm in the recipients of AN1792. One animal in each of the groups immunized with Aβ1–12 conjugate, Aβ13–28 conjugate and Aβ25–35 proliferated in response to Aβ1–40. The remaining groups receiving Aβ1–5 conjugate, Aβ33–42 conjugate pBx6 or PBS had no animals with an Aβ-stimulated response. These results are summarized in Table 7 below.

TABLE 7

| Immunogen | Conjugate | Aβ Amino Acids | Responders |
|---|---|---|---|
| Aβ1–5 | Yes | 5-mer | 0/7 |
| Aβ1–12 | Yes | 12-mer | 1/8 |
| Aβ13–28 | Yes | 16-mer | 1/9 |
| Aβ25–35 | | 11-mer | 1/9 |
| Aβ33–42 | Yes | 10-mer | 0/10 |
| Aβ1–40 | | 40-mer | 5/8 |
| Aβ1–42 | | 42-mer | 9/9 |
| r Aβ1–42 | | 42-mer | 8/8 |
| pBx6 | | | 0/8 |
| PBS | | 0-mer | 0/8 |

These results show that AN1792 and AN1528 stimulate strong T cell responses, most likely of the CD4$^+$ phenotype. The absence of an Aβ-specific T cell response in animals immunized with Aβ1–5 is not surprising since peptide epitopes recognized by CD4+ T cells are usually about 15 amino acids in length, although shorter peptides can sometimes function with less efficiency. Thus the majority of helper T cell epitopes for the four conjugate peptides are likely to reside in the IgG conjugate partner, not in the Aβ region. This hypothesis is supported by the very low incidence of proliferative responses for animals in each of these treatment groups. Since the Aβ1–5 conjugate was effective at significantly reducing the level of Aβ in the brain, in the apparent absence of Aβ-specific T cells, the key effector immune response induced by immunization with this peptide appears to be antibody.

Lack of T-cell and low antibody response from fusion peptide pBx6, encompassing APP amino acids 592–695 including all of the Aβ residues may be due to the poor immunogenicity of this particular preparation. The poor immunogenicity of the Aβ25–35 aggregate is likely due to the peptide being too small to be likely to contain a good T cell epitope to help the induction of an antibody response. It is anticipated that conjugation of this peptide to a carrier protein would render it more immunogenic.

V. Preparation of Polyclonal Antibodies for Passive Protection 125 non-transgenic mice were immunized with Aβ, plus adjuvant, and euthanized at 45 months. Blood was collected from immunized mice. IgG was separated from other blood components. Antibody specific for the immunogen may be partially purified by affinity chromatography. An average of about 0.5–1 mg of immunogen-specific antibody is obtained per mouse, giving a total of 60–120 mg.

VI. Passive Immunization with Antibodies to Aβ

Groups of 7–9 month old PDAPP mice each were injected with 0.5 mg in PBS of polyclonal anti-Aβ or specific anti-Aβ monoclonals as shown below. All antibody preparations were purified to have low endotoxin levels. Monoclonals can be prepared against a fragment by injecting the fragment or longer form of Aβ into a mouse, preparing hybridomas and screening the hybridomas for an antibody that specifically binds to a desired fragment of Aβ without binding to other nonoverlapping fragments of Aβ.

TABLE 8

| Antibody | Epitope |
| --- | --- |
| 2H3 | Aβ 1–12 |
| 10D5 | Aβ 1–12 |
| 266 | Aβ 13–28 |
| 21F12 | Aβ 33–42 |
| Mouse polyclonal anti-human Aβ42 | Anti-Aggregated Aβ42 |

Mice were injected ip as needed over a 4 month period to maintain a circulating antibody concentration measured by ELISA titer of greater than 1/1000 defined by ELISA to Aβ42 or other immunogen. Titers were monitored as above and mice were euthanized at the end of 6 months of injections. Histochemistry, Aβ levels and toxicology were performed post mortem. Ten mice were used per group. Additional studies of passive immunization are described in Examples XI and XII below.

VII. Comparison of Different Adjuvants

This example compares CFA, alum, an oil-in water emulsion and MPL for capacity to stimulate an immune response.
A. Materials and Methods
1. Study Design One hundred female Hartley strain six-week old guinea pigs, obtained from Elm Hill Breeding Laboratories, Chelmsford, Mass., were sorted into ten groups to be immunized with AN1792 or a palmitoylated derivative thereof combined with various adjuvants. Seven groups received injections of AN1792 (33 μg unless otherwise specified) combined with a) PBS, b) Freund's adjuvant, c) MPL, d) squalene, c) MPL/squalene f) low dose alum, or g) high dose alum (300 μg AN1792). Two groups received injections of a palmitoylated derivative of AN1792 (33 μg) combined with a) PBS or b) squalene. A final, tenth group received PBS alone without antigen or additional adjuvant. For the group receiving Freund's adjuvant, the first dose was emulsified with CFA and the remaining four doses with IFA. Antigen was administered at a dose of 33 μg for all groups except the high dose alum group, which received 300 μg of AN1792. Injections were administered intraperitoneally for CFA/IFA and intramuscularly in the hind limb quadriceps alternately on the right and left side for all other groups. The first three doses were given on a biweekly schedule followed by two doses at a monthly interval). Blood was drawn six to seven days following each immunization, starting after the second dose, for measurement of antibody titers.

2. Preparation of Immunogens

Two mg Aβ42 (California Peptide, Lot ME0339) was added to 0.9 ml of deionized water and the mixture was vortexed to generate a relatively uniform suspension. A 100 μl aliquot of 10×PBS (1×PBS, 0.15 M NaCl, 0.01 M sodium phosphate, pH 7.5) was added. The suspension was vortexed again and incubated overnight at 37° C. for use the next day. Unused Aβ1–42 was stored with desiccant as a lyophilized powder at −20° C.

A palmitoylated derivative of AN1792 was prepared by coupling palmitic anhydride, dissolved in dimethyl formamide, to the amino terminal residue of AN1792 prior to removal of the nascent peptide from the resin by treatment with hydrofluoric acid.

To prepare immunogenic formulation doses with Complete Freund's adjuvant (CFA) (group 2), 33 μg of AN1792 in 200 μl PBS was emulsified 1:1 (vol:vol) with CFA in a final volume of 400 μl for the first immunization. For subsequent immunizations, the antigen was similarly emulsified with Incomplete Freund's adjuvant (IFA).

To prepare formulation doses with MPL for groups 5 and 8, lyophilized powder (Ribi ImmunoChem Research, Inc., Hamilton, Mont.) was added to 0.2% aqueous triethylamine to a final concentration of 1 mg/ml and vortexed. The mixture was heated to 65 to 70° C. for 30 sec to create a slightly opaque uniform suspension of micelles. The solution was freshly prepared for each set of injections. For each injection in group 5, 33 μg of AN1792 in 16.5 μl PBS, 50 μg of MPL (50 μl) and 162 μl of PBS were mixed in a borosilicate tube immediately before use.

To prepare formulation doses with the low oil-in-water emulsion, AN1792 in PBS was added to 5% squalene, 0.5% Tween 80, 0.5% Span 85 in PBS to reach a final single dose concentration of 33 μg AN1792 in 250 μl (group 6). The mixture was emulsified by passing through a two-chambered hand-held device 15 to 20 times until the emulsion droplets appeared to be about equal in diameter to a 1.0 μm diameter standard latex bead when viewed under a microscope. The resulting suspension was opalescent, milky white. The emulsions were freshly prepared for each series of injections. For group 8, MPL in 0.2% triethylamine was added at a concentration of 50 μg per dose to the squalene and detergent mixture for emulsification as noted above. For the palmitoyl derivative (group 7), 33 μg per dose of palmitoyl-NH-Aβ1–42 was added to squalene and vortexed. Tween 80 and Span 85 were then added with vortexing. This mixture was added to PBS to reach final concentrations of 5% squalene, 0.5% Tween 80, 0.5% Span 85 and the mixture was emulsified as noted above.

To prepare formulation doses with alum (groups 9 and 10), AN1792 in PBS was added to Alhydrogel (aluminum hydroxide gel, Accurate, Westbury, N.Y.) to reach concentrations of 33 μg (low dose, group 9) or 300 μg (high dose, group 10) AN1792 per 5 mg of alum in a final dose volume of 250 μl. The suspension was gently mixed for 4 hr at RT.

3. Measurement of Antibody Titers

Guinea pigs were bled six to seven days following immunization after the second immunization for a total of four bleeds. Antibody titers against Aβ42 were measured by ELISA as described in General Materials and Methods.

4. Tissue Preparation

After about 14 weeks, all guinea pigs were euthanized by administration of $CO_2$. Cerebrospinal fluid was collected and the brains were removed and three brain regions (hippocampus, cortex and cerebellum) were dissected and used to measure the concentration of total Aβ protein using ELISA.

B. Results

1. Antibody Responses

Figure 14:
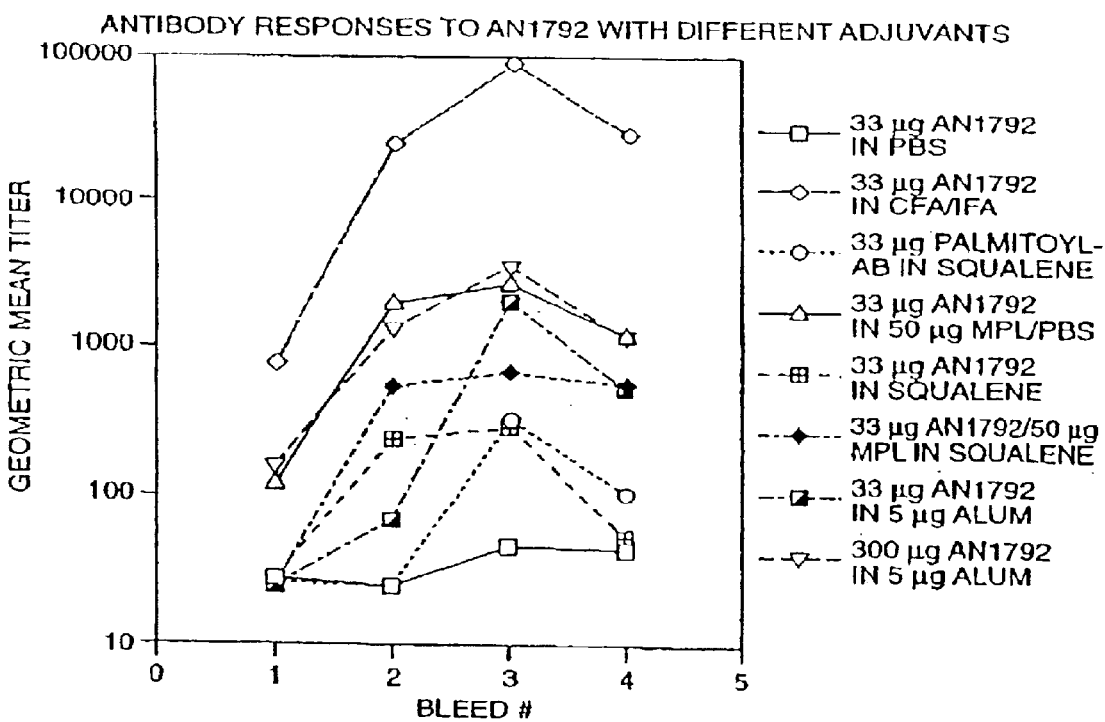
FIG. 14: Geometric mean titers of Aβ-specific antibody for groups of guinea pigs immunized with AN1792, or a palmitoylated derivative thereof, combined with various adjuvants.

There was a wide range in the potency of the various adjuvants when measured as the antibody response to AN1792 following immunization. As shown in FIG. 14, when AN1792 was administered in PBS, no antibody was detected following two or three immunizations and negligible responses were detected following the fourth and fifth doses with geometric mean titers (GMTs) of only about 45. The o/w emulsion induced modest titers following the third dose (GMT 255) that were maintained following the fourth dose (GMT 301) and fell with the final dose (GMT 54). There was a clear antigen dose response for AN1792 bound to alum with 300 μg being more immunogenic at all time points than 33 μg. At the peak of the antibody response, following the fourth immunization, the difference between the two doses was 43% with GMTs of about 1940 (33 μg) and 3400 (300 μg). The antibody response to 33 μg AN1792 plus MPL was very similar to that generated with almost a ten-fold higher dose of antigen (300 μg) bound to alum. The addition of MPL to an o/w emulsion decreased the potency of the formulation relative to that with MPL as the sole adjuvant by as much as 75%. A palmitoylated derivative of AN1792 was completely non-immunogenic when administered in PBS and gave modest titers when presented in an o/w emulsion with GMTs of 340 and 105 for the third and fourth bleeds. The highest antibody titers were generated with Freund's adjuvant with a peak GMT of about 87,000, a value almost 30-fold greater than the GMTs of the next two most potent formulations, MPL and high dose AN1792/alum.

The most promising adjuvants identified in this study are NTL and alum. Of these two, MPL appears preferable because a 10-fold lower antigen dose was required to generate the same antibody response as obtained with alum. The response can be increased by increasing the dose of antigen and/or adjuvant and by optimizing the immunization schedule. The o/w emulsion was a very weak adjuvant for AN1792 and adding an o/w emulsion to MPL adjuvant diminished the intrinsic adjuvant activity of MPL alone.

2. Aβ Levels in the Brain

At about 14 weeks the guinea pigs were deeply anesthetized, the cerebrospinal fluid (CSF) was drawn and brains were excised from animals in a subset of the groups, those immunized with Freund's adjuvant (group 2), MPL (group 5), alum with a high dose, 300 μg, of AN1792 (group 10) and the PBS immunized control group (group 3). To measure the level of Aβ peptide, one hemisphere was dissected and homogenates of the hippocampal, cortical, and cerebellar regions were prepared in 5 M guanidine. These were diluted and quantitated by comparison to a series of dilutions of Aβ standard protein of known concentrations in an ELISA format. The levels of Aβ protein in the hippocampus, the cortex and the cerebellum were very similar for all four groups despite the wide range of antibody responses to Aβ elicited by these formulations. Mean Aβ levels of about 25 ng/g tissue were measured in the hippocampus, 21 ng/g in the cortex, and 12 ng/g in the cerebellum. Thus, the presence of a high circulating antibody titer to Aβ for almost three months in some of these animals did not alter the total Aβ levels in their brains. The levels of Aβ in the CSF were also quite similar between the groups. The lack of large effect of AN1792 immunization on endogenous Aβ indicates that the immune response is focused on pathological formations of Aβ.

VIII. Immune Response to Different Adjuvants in Mice

Six-week old female Swiss Webster mice were used for this study with 10–13 animals per group. Immunizations were given on days 0, 14, 28, 60, 90 and 20 administered subcutaneously in a dose volume of 200 μl. PBS was used as the buffer for all formulations. Animals were bleed seven days following each immunization starting after the second dose for analysis of antibody titers by ELISA. The treatment regime of each group is summarized in Table 9.

TABLE 9

Experimental Design of Study 010

| Group | N[a] | Adjuvant[b] | Dose | Antigen | Dose (μg) |
|---|---|---|---|---|---|
| 1 | 10 | MPL | 12.5 μg | AN1792 | 33 |
| 2 | 10 | MPL | 25 μg | AN1792 | 33 |
| 3 | 10 | MPL | 50 μg | AN1792 | 33 |
| 4 | 13 | MPL | 125 μg | AN1792 | 33 |
| 5 | 13 | MPL | 50 μg | AN1792 | 150 |
| 6 | 13 | MPL | 50 μg | AN1528 | 33 |
| 7 | 10 | PBS | | AN1792 | 33 |
| 8 | 10 | PBS | | None | |
| 9 | 10 | Squalene emulsified | 5% | AN1792 | 33 |
| 10 | 10 | Squalene admixed | 5% | AN1792 | 33 |
| 11 | 10 | Alum | 2 mg | AN1792 | 33 |
| 12 | 13 | MPL + Alum | 50 μg/2 mg | AN1792 | 33 |
| 13 | 10 | QS-21 | 5 μg | AN1792 | 33 |
| 14 | 10 | QS-21 | 10 μg | AN1792 | 33 |
| 15 | 10 | QS-21 | 25 AN1792 | AN1792 | 33 |
| 16 | 13 | QS-21 | 25 AN1792 | AN1792 | 150 |
| 17 | 13 | QS-21 | 25 AN1792 | AN1528 | 33 |
| 18 | 13 | QS-21 + MPL | 25 μg/50 μg | AN1792 | 33 |
| 19 | 13 | QS-21 + Alum | 25 μg/2 mg | AN1792 | 33 |

Footnotes:
[a]Number of mice in each group at the initiation of the experiment.
[b]The adjuvants are noted. The buffer for all these formulations was PBS. For group 8, there was no adjuvant and no antigen.

The ELISA titers of antibodies against Aβ42 in each group are shown in Table 10 below.

TABLE 10

| Treatment Group | Geometric Mean Antibody Titers Week of Bleed | | | | |
|---|---|---|---|---|---|
| | 2.9 | 5.0 | 8.7 | 12.9 | 16.7 |
| 1 | 248 | 1797 | 2577 | 6180 | 4177 |
| 2 | 598 | 3114 | 3984 | 5287 | 6878 |
| 3 | 1372 | 5000 | 7159 | 12333 | 12781 |
| 4 | 1278 | 20791 | 14368 | 20097 | 25631 |
| 5 | 3288 | 26242 | 13229 | 9315 | 23742 |
| 6 | 61 | 2536 | 2301 | 1442 | 4504 |
| 7 | 37 | 395 | 484 | 972 | 2149 |

TABLE 10-continued

| Treatment Group | Geometric Mean Antibody Titers Week of Bleed | | | | |
|---|---|---|---|---|---|
| | 2.9 | 5.0 | 8.7 | 12.9 | 16.7 |
| 8 | 25 | 25 | 25 | 25 | 25 |
| 9 | 25 | 183 | 744 | 952 | 1823 |
| 10 | 25 | 89 | 311 | 513 | 817 |
| 11 | 29 | 708 | 2618 | 2165 | 3666 |
| 12 | 198 | 1458 | 1079 | 612 | 797 |
| 13 | 38 | 433 | 566 | 1080 | 626 |
| 14 | 104 | 541 | 3247 | 1609 | 838 |
| 15 | 212 | 2630 | 2472 | 1224 | 1496 |
| 16 | 183 | 2616 | 6680 | 2085 | 1631 |
| 17 | 28 | 201 | 375 | 222 | 1540 |
| 18 | 31699 | 15544 | 23095 | 6412 | 9059 |
| 19 | 63 | 243 | 554 | 299 | 441 |

The table shows that the highest titers were obtained for groups 4, 5 and 18, in which the adjuvants were 125 μg MPL, 50 μg MPL and QS-21 plus MPL.

IX. Therapeutic Efficacy of Different Adjuvants

A therapeutic efficacy study was conducted in PDAPP transgenic mice with a set of adjvants suitable for use in humans to determine their ability to potentiate immune responses to Aβ and to induce the immune-mediated clearance of amyloid deposits in the brain.

One hundred eighty male and female, 7.5- to 8.5-month old heterozygous PDAPP transgenic mice were obtained from Charles River Laboratories. The mice were sorted into nine groups containing 15 to 23 animals per group to be immunized with AN1792 or AN1528 combined with various adjuvants. Animals were distributed to match the gender, age, and parentage of the animals within the groups as closely as possible. The adjuvants included alum, MPL, and QS-21, each combined with both antigens, and Freund's adjuvant (FA) combined with only AN1792. An additional group was immunized with AN1792 formulated in PBS buffer plus the preservative thimerosal without adjuvant. A ninth group was immunized with PBS alone as a negative control.

Preparation of aggregated Aβ peptides: human Aβ1–40 (AN1528; California Peptides Inc., Napa, Calif.; Lot ME0541) and human Aβ1–42 (AN1792; California Peptides Inc., Lot ME0439) peptides were freshly solubilized for the preparation of each set of injections from lyophilized powders that had been stored desiccated at −20° C. For this purpose, two mg of peptide were added to 0.9 ml of deionized water and the mixture was vortexed to generate a relatively uniform solution or suspension. AN1528 was soluble at this step, in contrast to AN1792. A 100 μl aliquot of 10×PBS (1×PBS: 0.15 M NaCl, 0.01 M sodium phosphate, pH 7.5) was then added at which point AN1528 began to precipitate. The suspensions were vortexed again and incubated overnight at 37° C. for use the next day.

To prepare formulation doses with alum (Groups 1 and 5). Aβ peptide in PBS was added to Alhydrogel (two percent aqueous aluminum hydroxide gel, Sargeant, Inc., Clifton, N.J.) to reach concentrations of 100 μg Aβ peptide per 2 mg of alum. 10×PBS was added to a final dose volume of 200 ml in 1×PBS. The suspension was then gently mixed for approximately 4 hr at RT prior to injection.

To prepare formulation doses for with MPL (Groups 2 and 6), lyophilized powder (Ribi ImmunuoChem Research, Inc., Hamilton, Mont.; Lot 67039-E0896B) was added to 0.2% aqueous triethylamine to a final concentration of 1 mg/ml and vortexed. The mixture was heated to 65 to 70° C. for 30 sec to create a slightly opaque uniform suspension of micelles. The solution was stored at 4° C. For each set of injections, 100 μg of peptide per dose in 50 μl PBS, 50 μg of MPL per dose (50 μl) and 100 μl of PBS per dose were mixed in a borosilicate tube immediately before use.

To prepare formulation doses with QS-21 (Groups 3 and 7), lyophilized powder (Aquila, Framingham, Mass.; Lot A7018R) was added to PBS, pH 6.6–6.7 to a final concentration of 1 mg/ml and vortexed. The solution was stored at −20° C. For each set of injections, 100 μg of peptide per dose in 50 μl PBS, 25 μg of QS-21 per dose in 25 μl PBS and 125 μl of PBS per dose were mixed in a borosihicates tube immediately before use.

To prepare formulation doses with Freund's Adjuvant (Group 4), 100 μg of AN1792 in 200 μl PBS was emulsified 1:1 (vol:vol) with Complete Freund's Adjuvant (CFA) in a final volume of 400 μl for the first immunization. For subsequent immunizations, the antigen was similarly emulsified with Incomplete Freund's Adjuvant (WFA). For the formulations containing the adjuvants alum, MPL or QS21, 100 μg per dose of AN1792 or AN1528 was combined with alum (12 mg per dose) or MPL (50 μg per dose) or QS21 (25 μg per dose) in a final volume of 200 μl PBS and delivered by subcutaneous inoculation on the back between the shoulder blades. For the group receiving FA, 100 μg of AN1792 was emulsified 1:1 (vol:vol) with Complete Freund's adjuvant (CFA) in a final volume of 400 μl and delivered intraperitoneally for the first immunization, followed by a boost of the same amount of immunogen in Incomplete Freund's adjuvant (IFA) for the subsequent five doses. For the group receiving AN1792 without adjuvant, 10 μg AN1792 was combined with 5 μg thimerosal in a final volume of 50 μl PBS and delivered subcutaneously. The ninth, control group received only 200 μl PBS delivered subcutaneously. Immunizations were given on a biweekly schedule for the first three doses, then on a monthly schedule thereafter on days 0, 16, 28, 56, 85 and 112. Animals were bled six to seven days following each immunization starting after the second dose for the measurement of antibody titers. Animals were euthanized approximately one week after the final dose. Outcomes were measured by ELISA assay of Aβ and APP levels in brain and by immunohistochemical evaluation of the presence of amyloid plaques in brain sections. In addition, Aβ-specific antibody titers, and Aβ-dependent proliferative and cytokine responses were determined.

Table 11 shows that the highest antibody titers to Aβ1–42 were elicited with FA and AN1792, titers which peaked following the fourth immunization (peak-GMT: 75,386) and then declined by 59% after the final, sixth immunization. The peak mean titer elicited by MPL with AN1792 was 62% lower than that generated with FA (peak GMT: 28,867) and was also reached early in the immunization scheme, after 3 doses, followed by a decline to 28% of the peak value after the sixth immunization. The peak mean titer generated with QS-21 combined with AN1792 (GMT: 1,511) was about 5-fold lower than obtained with MPL. In addition, the kinetics of the response were slower, since an additional immunization was required to reach the peak response. Titers generated by alum-bound AN1792 were marginally greater than those obtained with QS-21 and the response kinetics were more rapid. For AN1792 delivered in PBS with thimerosal the frequency and size of titers were barely greater than that for PBS alone. The peak titers generated with MPL and AN1528 (peak GMT 3099) were about 9-fold lower than those with AN1792. Alum-bound AN1528 was very poorly immunogenic with low titers generated in only some of the animals. No antibody responses were observed in the control animals immunized with PBS alone.

TABLE 11

Geometric Mean Antibody Titers[a]
Week of Bleed

| Treatment | 3.3 | 5.0 | 9.0 | 13.0 | 17.0 |
|---|---|---|---|---|---|
| Alum/ | 102 | 1,081 | 2,366 | 1,083 | 572 |
| AN1792 | (12/21)[b] | (17/20) | (21/21) | (19/21) | (18/21) |
| MPL/ | 6241 | 28,867 | 1,1242 | 5,665 | 8,204 |
| AN1792 | (21/21) | (21/21) | (21/21) | (20/20) | (20/20) |
| QS-21/ | 30 | 227 | 327 | 1,511 | 1,188 |
| AN1792 | (1/20) | (10/19) | (10/19) | (17/18) | (14/18) |
| CFA/ | 10,076 | 61,279 | 75,386 | 41,628 | 30,574 |
| AN1792 | (15/15) | (15/15) | (15/15) | (15/15) | (15/15) |
| Alum/ | 25 | 33 | 39 | 37 | 31 |
| AN1528 | (0/21) | (1/21) | (3/20) | (1/20) | (2/20) |
| MPL/ | 184 | 2,591 | 1,653 | 1,156 | 3,099 |
| AN1528 | (15/21) | (20/21) | (21/21) | (20/20) | (20/20) |
| QS-21/ | 29 | 221 | 51 | 820 | 2,994 |
| AN1528 | (1/22) | (13/22) | (4/22) | (20/22) | (21/22) |
| PBS plus | 25 | 33 | 39 | 37 | 47 |
| Thimerosal | (0/16) | (2/16) | (4/16) | (3/16) | (4/16) |
| PBS | 25 | 25 | 25 | 25 | 25 |
|  | (0/16) | (0/16) | (0/15) | (0/12) | (0/16) |

Footnotes:
[a]Geometric mean antibody titers measured against Aβ1–42
[b]Number of responders per group The results of AN1792 or AN1592 treatment with various adjuvants, or thimerosal on cortical amyloid burden in 12-month old mice determined by ELISA are shown in FIGS. 15A–15E. In PBS control PDAPP mice (FIG. 15A), the median level of total Aβ in the cortex at 12 months was 1,817 ng/g. Notably reduced levels of Aβ were observed in mice treated with AN1792 plus CFA/IFA (FIG. 15C), AN1792 plus alum (FIG. 15D), AN1792 plus MPL (FIG. 15E) and QS21 plus AN1792 (FIG. 15E). The reduction reached statistical significance (p<0.0S) only for AN1792 plus CFA/IFA (FIG. 15C). However, as shown in Examples I and III, the effects of immunization in reducing Aβ levels become substantially greater in 15 month and 18 month old mice. Thus, it is expected that at least the AN1792 plus alum, AN1792 plus MPL and AN1792 plus QS21 compositions will achieve statistical significance in treatment of older mice. By contrast, the AN1792 plus the preservative thimerosal (FIG. 15D) showed a median level of Aβ about the same as that in the PBS treated mice. Similar results were obtained when cortical levels of Aβ42 were compared. The median level of Aβ42 in PBS controls was 1624 ng/g. Notably reduced median levels of 403, 1149, 620 and 714 were observed in the mice treated with AN1792 plus CFA/IFA, AN1792 plus alum, AN1792 plus MPL and AN1792 plus QS21 respectively, with the reduction achieving statistical significance (p=0.05) for the AN1792 CFA/IFA treatment group. The median level in the AN1792 thimerosal treated mice was 1619 ng/g Aβ42.

X. Toxicity Analysis

Tissues were collected for histopathologic examination at the termination of studies described in Examples II, III and VII. In addition, hematology and clinical chemistry were performed on terminal blood samples from Examples III and VI. Most of the major organs were evaluated, including brain, pulmonary, lymphoid, gastrointestinal, liver, kidney, adrenal and gonads. Although sporadic lesions were observed in the study animals, there were no obvious differences, either in tissues affected or lesion severity, between AN1792 treated and untreated animals. There were no unique histopathological lesions noted in AN-1528-immunized animals compared to PBS-treated or untreated animals. There were also no differences in the clinical chemistry profile between adjuvant groups and the PBS treated animals in Example VI. Although there were significant increases in several of the hematology parameters between animals treated with AN1792 and Freund's adjuvant in Example VI relative to PBS treated animals, these type of effects are expected from Freund's adjuvant treatment and the accompanying peritonitis and do not indicate any adverse effects from AN1792 treatment. Although not part of the toxicological evaluation, PDAPP mouse brain pathology was extensively examined as part of the efficacy endpoints. No sign of treatment related adverse effect on brain morphology was noted in any of the studies. These results indicate that AN1792 treatment is well tolerated and at least substantially free of side effects.

XI. Therapeutic Treatment with Anti-Aβ Antibodies

The experiments described in this section were carried out in order to test the abilities of various monoclonal and polyclonal antibodies against Aβ to inhibit accumulation of Aβ in the brain of heterozygotic transgenic mice.

A. Study 1

1. Study Design

Sixty male and female, heterozygous PDAPP transgenic mice, 8.5 to 10.5 months of age were obtained from Charles River Laboratory. The mice were sorted into six groups to be treated with various antibodies directed to Aβ. Animals were distributed to match the gender, age, parentage and source of the animals within the groups as closely as possible. As shown in Table 12, the antibodies included four murine Aβ-specific monoclonal antibodies, 2H3 (directed to Aβ residues 1–12), 10D5 (directed to Aβ residues 1–16), 266 (directed to Aβ residues 13–28 and binds to monomeric but not to aggregated AN1792), 21F12 (directed to Aβ residues 33–42). A fifth group was treated with an Aβ-specific polyclonal antibody fraction (raised by immunization with aggregated AN1792). The negative control group received the diluent, PBS, alone without antibody.

The monoclonal antibodies were injected at a dose of about 10 mg/kg (assuming that the mice weighed 50 g). Injections were administered intraperitoneally every seven days on average to maintain anti-Aβ titers above 1000. Although lower titers were measured for mAb 266 since it does not bind well to the aggregated AN1792 used as the capture antigen in the assay, the same dosing schedule was maintained for this group. The group receiving monoclonal antibody 2H3 was discontinued within the first three weeks since the antibody was cleared too rapidly in vivo. Animals were bled prior to each dosing for the measurement of antibody titers. Treatment was continued over a six-month period for a total of 196 days. Animals were euthanized one week after the final dose.

TABLE 12

Experimental Design of Study 006

| Treatment Group | N[a] | Treatment Antibody | Antibody Specificity | Antibody Isotype |
|---|---|---|---|---|
| 1 | 9 | none (PBS alone) | NA[b] | NA |
| 2 | 10 | Polyclonal | Aβ1–42 | mixed |
| 3 | 0 | mAb[c]2H3 | Aβ1–12 | IgG1 |

TABLE 12-continued

Experimental Design of Study 006

| Treatment Group | N[a] | Treatment Antibody | Antibody Specificity | Antibody Isotype |
|---|---|---|---|---|
| 4 | 8 | mAb 10D5 | Aβ1–16 | IgG1 |
| 5 | 6 | mAb 266 | Aβ13–28 | IgG1 |
| 6 | 8 | mAb 21F12 | Aβ33–42 | IgG2a |

Footnotes
[a]Number of mice in group at termination of the experiment. All groups started with 10 animals per group.
[b]NA: not applicable
[c]mAb: monoclonal antibody 2. Materials and Methods
a. Preparation of the Antibodies The anti-Aβ polyclonal antibody was prepared from blood collected from two groups of animals. The first group consisted of 100 female Swiss Webster mice, 6 to 8 weeks of age. They were immunized on days 0, 15, and 29 with 100 μg of AN1792 combined with CFA/IFA. A fourth injection was given on day 36 with one-half the dose of AN1792. Animals were exsanguinated upon sacrifice at day 42, serum was prepared and the sera were pooled to create a total of 64 ml. The second group consisted of 24 female mice isogenic with the PDAPP mice but nontransgenic for the human APP gene, 6 to 9 weeks of age. They were immunized on days 0, 14, 28 and 56 with 100 μg of AN1792 combined with CFA/IFA. These animals were also exsanguinated upon sacrifice at day 63, serum was prepared and pooled for a total of 14 ml. The two lots of sera were pooled. The antibody fraction was purified using two sequential rounds of precipitation with 50% saturated ammonium sulfate. The final precipitate was dialyzed against PBS and tested for endotoxin. The level of endotoxin was less than 1 EU/mg.

The anti-Aβ monoclonal antibodies were prepared from ascites fluid. The fluid was first delipidated by the addition of concentrated sodium dextran sulfate to ice-cold ascites fluid by stirring on ice to a reach a final concentration of 0.238%. Concentrated $CaCl_2$ was then added with stirring to reach a final concentration of 64 mM. This solution was centrifuged at 10,000×g and the pellet was discarded. The supernatant was stirred on ice with an equal volume of saturated ammonium sulfate added dropwise. The solution was centrifuged again at 10,000×g and the supernatant was discarded. The pellet was resuspended and dialyzed against 20 mM Tris-HCl, 0.4 M NaCl, pH 7.5. This fraction was applied to a Pharmacia FPLC Sepharose Q Column and eluted with a reverse gradient from 0.4 M to 0.275 M NaCl in 20 mM Tris-HCl, pH 7.5.

The antibody peak was identified by absorbance at 280 nm and appropriate fractions were pooled. The purified antibody preparation was characterized by measuring the protein concentration using the BCA method and the purity using SDS-PAGE. The pool was also tested for endotoxin. The level of endotoxin was less than 1 EU/mg. titers, titers less than 100 were arbitrarily assigned a titer value of 25.

3. Aβ and APP Levels in the Brain:

Following about six months of treatment with the various anti-Aβ antibody preparations, brains were removed from the animals following saline perfusion. One hemisphere was prepared for immunohistochemical analysis and the second was used for the quantitation of Aβ and APP levels. To measure the concentrations of various forms of beta amyloid peptide and amyloid precursor protein (APP), the hemisphere was dissected and homogenates of the hippocampal, cortical, and cerebellar regions were prepared in 5M guanidine. These were serially diluted and the level of amyloid peptide or APP was quantitated by comparison to a series of dilutions of standards of Aβ peptide or APP of known concentrations in an ELISA format.

The levels of total Aβ and of Aβ1–42 measured by ELISA in homogenates of the cortex, and the hippocampus and the level of total Aβ in the cerebellum are shown in Tables 11, 12, and 13, respectively. The median concentration of total Aβ for the control group, inoculated with PBS, was 3.6-fold higher in the hippocampus than in the cortex (median of 63,389 ng/g hippocampal tissue compared to 17,81 ng/g for the cortex). The median level in the cerebellum of the control group (30.6 ng/g tissue) was more than 2,000-fold lower than in the hippocampus. These levels are similar to those that we have previously reported for heterozygous PDAPP transgenic mice of this age (Johnson-Woods et al., 1997).

For the cortex, one treatment group had a median Aβ level, measured as Aβ1–42, which differed significantly from that of the control group (p<0.05), those animals receiving the polyclonal anti-Aβ antibody as shown in Table 13. The median level of Aβ1–42 was reduced by 65%, compared to the control for this treatment group. The median levels of Aβ1–42 were also significantly reduced by 55% compared to the control in one additional treatment group, those animals dosed with the mAb 10D5 (p=0.0433).

TABLE 13

CORTEX

| Treatment Group | N[a] | Medians | | | | | | Means | |
|---|---|---|---|---|---|---|---|---|---|
| | | Total Aβ | | | Aβ42 | | | Total Aβ | Aβ42 |
| | | ELISA value[b] | P value[c] | % Change | ELISA value | P value | % Change | ELISA value | ELISA value |
| PBS | 9 | 17818 | NA[d] | NA | 13802 | NA | NA | 16150 +/− 7456[e] | 12621 +/− 5738 |
| Polyclonal anti-Aβ42 | 10 | 6160 | 0.0055 | −65 | 4892 | 0.0071 | −65 | 5912 +/− 4492 | 4454 +/− 3347 |
| mAb 10D5 | 8 | 7915 | 0.1019 | −56 | 6214 | 0.0433 | −55 | 9695 +/− 6929 | 6943 +/− 3351 |
| mAb 266 | 6 | 9144 | 0.1255 | −49 | 8481 | 0.1255 | −39 | 9204 +/− 9293 | 7489 +/− 6921 |
| mAb 21F12 | 8 | 15158 | 0.2898 | −15 | 13578 | 0.7003 | −2 | 12481 +/− 7082 | 11005 +/− 6324 |

Footnotes:
[a]Number of animals per group at the end of the experiment;
[b]ng/g tissue;
[c]Mann Whitney analysis;
[d]NA: not applicable
[e]Standard Deviation In the hippocampus, the median percent reduction of total Aβ associated with treatment with polyclonal anti-Aβ antibody (50%, p=0.0055) was not as great as that observed in the cortex (65%) (Table 14). However, the absolute magnitude of the reduction was almost 3-fold greater in the hippocampus than in the cortex, a net reduction of 31,683 ng/g tissue in the hippocampus versus 11,658 ng/g tissue in the cortex. When measured as the level of the more amyloidogenic form of Aβ, Aβ1–42, rather than as total Aβ, the reduction achieved with the polyclonal antibody was significant (p=0.0025). The median levels in groups treated with the mAbs 10D5 and 266 were reduced by 33% and 21%, respectively.

TABLE 14

HIPPOCAMPUS

| Treatment Group | N[a] | Medians | | | | | | Means | |
|---|---|---|---|---|---|---|---|---|---|
| | | Total Aβ | | | Aβ42 | | | Total Aβ | Aβ42 |
| | | ELISA value[b] | P value[c] | % Change | ELISA value | P value | % Change | ELISA value | ELISA value |
| PBS | 9 | 63389 | NA[d] | NA | 54429 | NA | NA | 58351 +/− 13308[e] | 52801 +/− 14701 |
| Polyclonal anti-Aβ42 | 10 | 31706 | 0.0055 | −50 | 27127 | 0.0025 | −50 | 30058 +/− 22454 | 24853 +/− 18262 |
| mAb 10D5 | 8 | 46779 | 0.0675 | −26 | 36290 | 0.0543 | −33 | 44581 +/− 18632 | 36465 +/− 17146 |
| mAb 266 | 6 | 48689 | 0.0990 | −23 | 43034 | 0.0990 | −21 | 36419 +/− 27304 | 32919 +/− 25372 |
| mAb 21F12 | 8 | 51563 | 0.7728 | −19 | 47961 | 0.8099 | −12 | 57327 +/− 28927 | 50305 +/− 23927 |

Footnotes:
[a]Number of animals per group at the end of the experiment
[b]ng/g tissue
[c]Mann Whitney analysis
[d]NA: not applicable
[e]Standard Deviation Total Aβ was also measured in the cerebellum (Table 15). Those groups dosed with the polyclonal anti-Aβ and the 266 antibody showed significant reductions of the levels of total Aβ (43% and 46%, p=0.0033 and p=0.0184, respectively) and that group treated with 10D5 had a near significant reduction (29%, p=0.0675).

TABLE 15

CEREBELLUM

| Treatment Group | N[a] | Medians Total Aβ | | | Means |
|---|---|---|---|---|---|
| | | ELISA value[b] | P value[c] | % Change | Total Aβ ELISA value |
| PBS | 9 | 30.64 | NA[d] | NA | 40.00 +/− 31.89[e] |
| Polyclonal anti-Aβ42 | 10 | 17.61 | 0.0033 | −43 | 18.15 +/− 4.36 |
| mAb 10D5 | 8 | 21.68 | 0.0675 | −29 | 27.29 +/− 19.43 |
| mAb 266 | 6 | 16.59 | 0.0184 | −46 | 19.59 +/− 6.59 |
| mAb 21F12 | 8 | 29.80 | >0.9999 | −3 | 32.88 +/− 9.90 |

Footnotes:
[a]Number of animals per group at the end of the experiment
[b]ng/g tissue
[c]Mann Whitney analysis
[d]NA: not applicable
[e]Standard Deviation APP concentration was also determined by ELISA in the cortex and cerebellum from antibody-treated and control, PBS-treated mice. Two different APP assays were utilized. The first, designated APP-α/FL, recognizes both APP-alpha (α, the secreted form of APP which has been cleaved within the Aβ sequence), and full-length forms (FL) of APP, while the second recognizes only APP-α. In contrast to the treatment-associated diminution of Aβ in a subset of treatment groups, the levels of APP were virtually unchanged in all of the unchanged in all of the treated compared to the control animals. These results indicate that the immunizations with Aβ antibodies deplete Aβ without depleting APP.

In summary, Aβ levels were significantly reduced in the cortex, hippocampus and cerebellum in animals treated with the polyclonal antibody raised against AN1792. To a lesser extent monoclonal antibodies to the amino terminal region of Aβ1–42, specifically amino acids 1–16 and 13–28 also showed significant treatment effects.

4. Histochemical Analyses:

The morphology of Aβ-immunoreactive plaques in subsets of brains from mice in the PBS, polyclonal Aβ42, 21F12, 266 and 10D5 treatment groups was qualitatively compared to that of previous studies in which standard immunization procedures with Aβ42 were followed.

The largest alteration in both the extent and appearance of amyloid plaques occurred in the animals immunized with the polyclonal Aβ42 antibody. The reduction of amyloid load, eroded plaque morphology and cell-associated Aβ immunoreactivity closely resembled effects produced by the standard immunization procedure. These observations support the ELISA results in which significant reductions in both total AB and Aβ42 were achieved by administration of the polyclonal Aβ42 antibody.

In similar qualitative evaluations, amyloid plaques in the 10D5 group were also reduced in number and appearance, with some evidence of cell-associated Aβ immunoreactivity. Major differences were not seen when the 21F12 and 266 groups were compared with the PBS controls.

Figure 16:
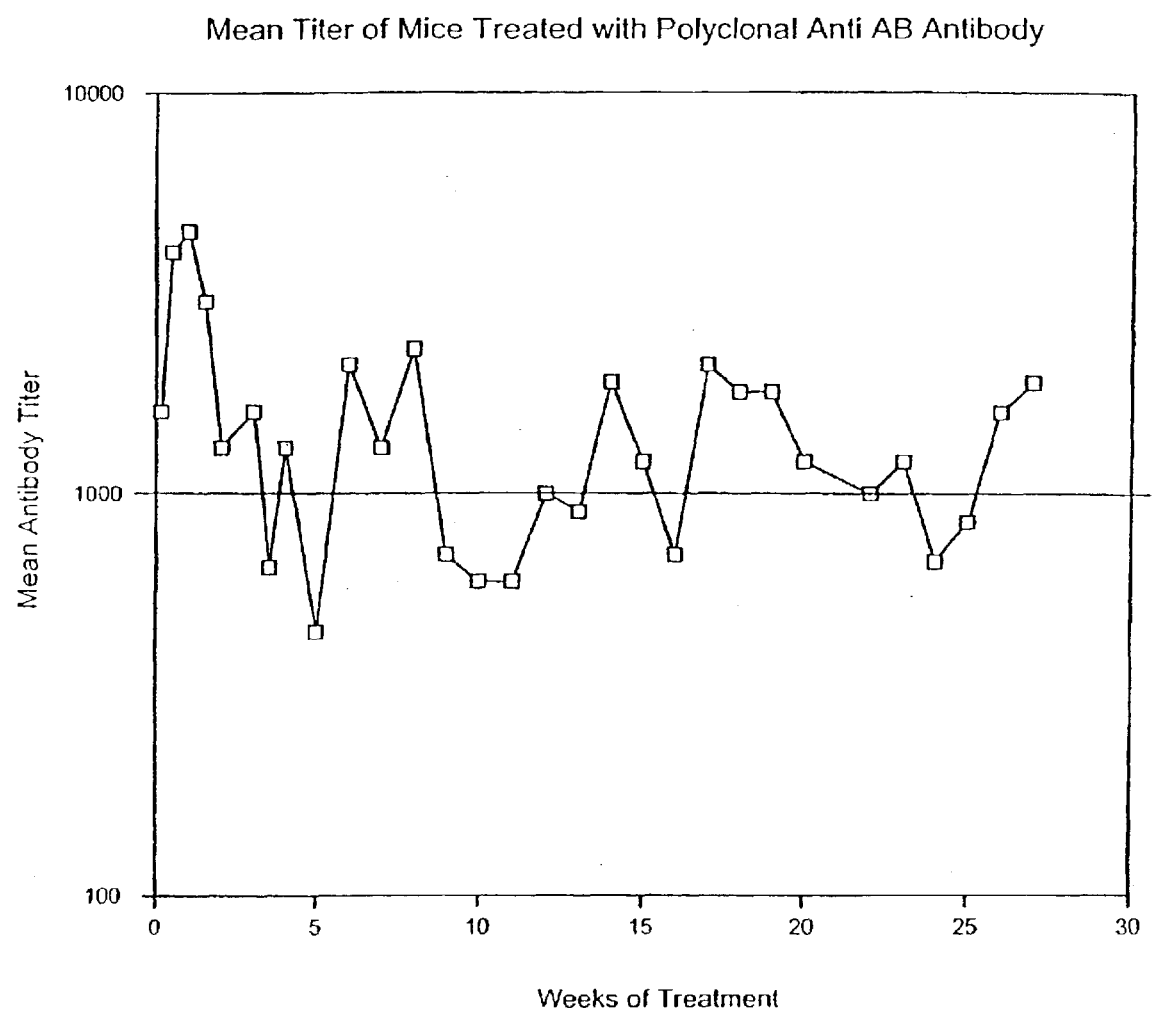
FIG. 16: Mean titer of mice treated with polyclonal antibody to Aβ.
Figure 17:
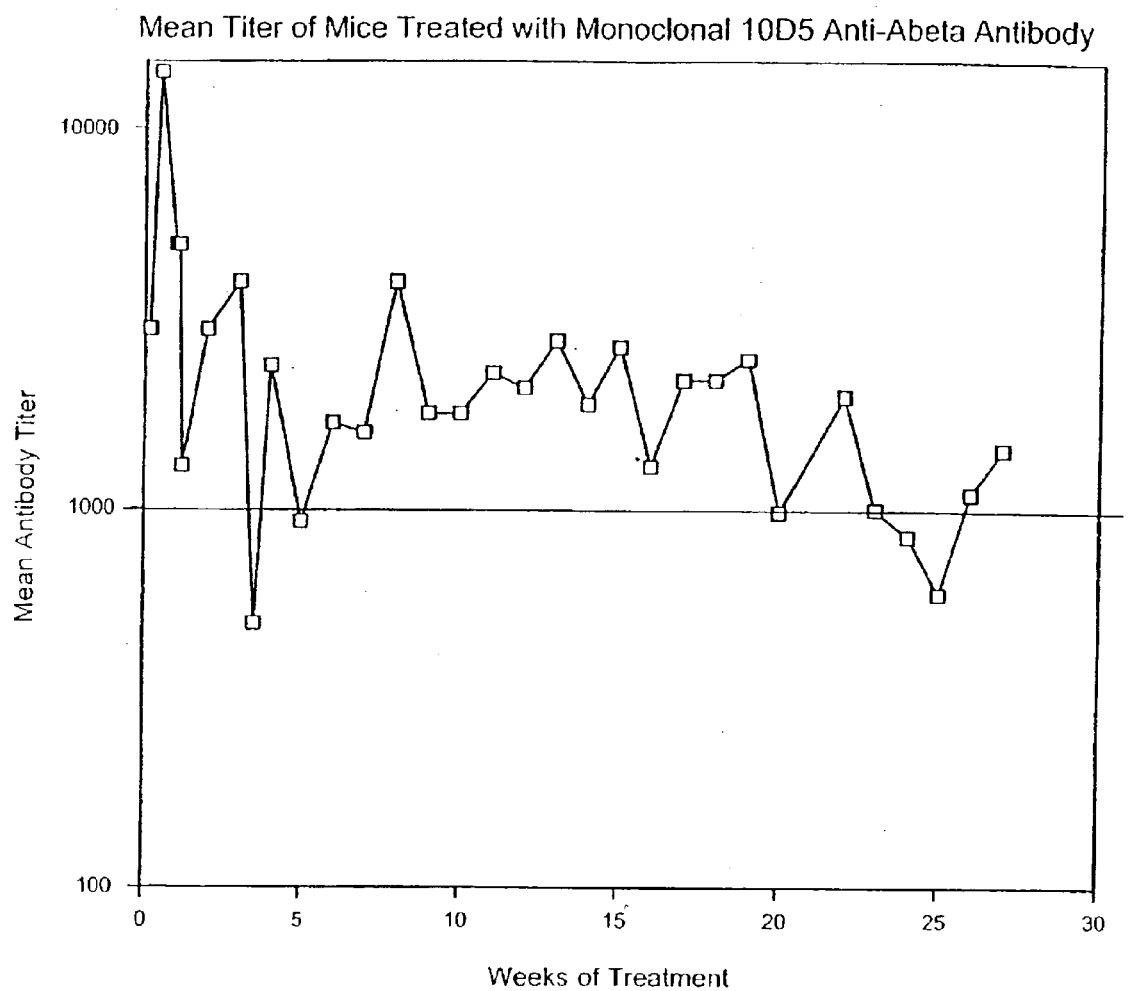
FIG. 17: Mean titer of mice treated with monoclonal antibody 10D5 to Aβ.
Figure 18:
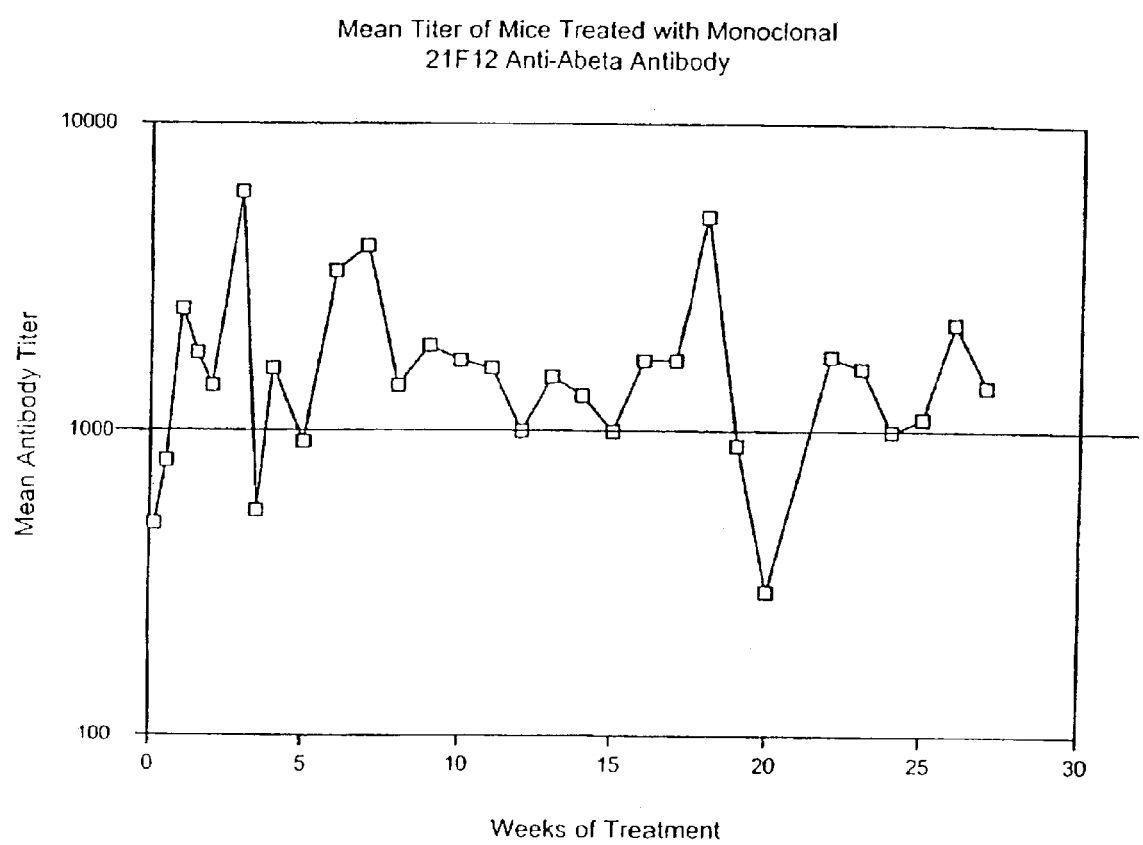
FIG. 18: Mean titer of mice treated with monoclonal antibody 2F12 to Aβ.

5. Measurement of Antibody Titers:

A subset of three randomly chosen mice from each group were bled just prior to each intraperitoneal inoculation, for a total of 30 bleeds. Antibody titers were measured as Aβ1–42-binding antibody using a sandwich ELISA with plastic multi-well plates coated with Aβ1–42 as described in detail in the General Materials and Methods. Mean titers for each bleed are shown in FIGS. 16–18 for the polyclonal antibody and the monoclonals 10D5 and 21F12, respectively. Titers averaged about 1:1000 over this time period for the polyclonal antibody preparation and were slightly above this level for the 10D5- and 21F12-treated animals.

6. Lymphoproliferative Responses

Aβ-dependent lymphoproliferation was measured using spleen cells harvested eight days following the final antibody infusion. Freshly harvested cells, $10^5$ per well, were cultured for 5 days in the presence of Aβ1–40 at a concentration of 5 µM for stimulation. As a positive control, additional cells were cultured with the T cell mitogen, PHA, and, as a negative control, cells were cultured without added peptide.

Splenocytes from aged PDAPP mice passively immunized with various anti-Aβ antibodies were stimulated in vitro with AN1792 and proliferative and cytokine responses were measured. The purpose of these assays was to determine if passive immunization facilitated antigen presentation, and thus priming of T cell responses specific for AN1792. No AN1792-specific proliferative or cytokine responses were observed in mice passively immunized with the anti-Aβ antibodies.

B. Study 2

In a second study, treatment with antibody 10D5 was repeated and two additional anti-Aβ antibodies were tested, monoclonal antibodies 3D6 (Aβ$_{1-5}$) and 16C11 (Aβ33-42). Control groups received either PBS or an irrelevant isotype-matched antibody (TM2a). The mice were older (11.5–12 month old heterozygotes) than in the previous study; otherwise the experimental design was the same. Once again, after six months of treatment, 10D5 reduced plaque burden by greater than 80% relative to either the PBS or isotype-matched antibody controls (p=0.003). One of the other antibodies against Aβ, 3D6, was equally effective, producing an 86% reduction (p=0.003). In contrast, the third antibody against the peptide, 16C11, failed to have any effect on plaque burden. Similar findings were obtained with Aβ$_{42}$ ELISA measurements. These results demonstrate that an antibody response against Aβ peptide, in the absence of T cell immunity, is sufficient to decrease amyloid deposition in PDAPP mice, but that not all anti-Aβ antibodies are efficacious. Antibodies directed to epitopes comprising amino acids 1–5 or 3–7 of Aβ are particularly efficacious.

These studies demonstrate that passively administered antibodies against Aβ reduced the extent of plaque deposition in a mouse model of Alzheimer's disease. When held at modest serum concentrations (25–70 µg/ml), the antibodies gained access to the CNS at levels sufficient to decorate β-amyloid plaques. Antibody entry into the CNS was not due to abnormal leakage of the blood-brain barrier since there was no increase in vascular permeability as measured by Evans Blue in PDAPP mice. In addition, the concentration of antibody in the brain parenchyma of aged PDAPP mice was the same as in non-transgeric mice, representing 0.1% of the antibody concentration in serum (regardless of isotype).

C. Study 3: Monitoring of Antibody Binding

To determine whether antibodies against Aβ could be acting directly within the CNS, brains taken from saline-perfused mice at the end of the Example XII, were examined for the presence of the peripherally-administered antibodies. Unfixed cryostat brain sections were exposed to a fluorescent reagent against mouse immunoglobulin (goat anti-mouse IgG-Cy3). Plaques within brains of the 10D5 and 3D6 groups were strongly decorated with antibody, while there was no staining in the 16C11 group. To reveal the full extent of plaque deposition, serial sections of each brain were first immunoreacted with an anti-Aβ antibody, and then with the secondary reagent 10D5 and 3D6, following peripheral administration, gained access to most plaques within the CNS. The plaque burden was greatly reduced in these treatment groups compared to the 16C11 group. These data indicate that peripherally administered antibodies can enter the CNS where they can directly trigger amyloid clearance. It is likely that 16C11 also had access to the plaques but was unable to bind to the plaques.

XI. Prevention and Treatment of Human Subjects

A single-dose phase I trial is performed to determine safety in humans. A therapeutic agent is administered in increasing dosages to different patients starting from about 0.01 the level of presumed efficacy, and increasing by a factor of three until a level of about 10 times the effective mouse dosage is reached.

A phase II trial is performed to determine therapeutic efficacy. Patients with early to mid Alzheimer's Disease defined using Alzheimer's disease and Related Disorders Association (ADRDA) criteria for probable Aβ are selected. Suitable patients score in the 12–26 range on the Mini-Mental State Exam (MMSE). Other selection criteria are that patients are likely to survive the duration of the study and lack complicating issues such as use of concomitant medications that may interfere. Baseline evaluations of patient function are made using classic psychometric measures, such as the MMSE, and the ADAS, which is a comprehensive scale for evaluating patients with Alzheimer's Disease status and function. These psychometric scales provide a measure of progression of the Alzheimer's condition. Suitable qualitative life scales can also be used to monitor treatment. Disease progression can also be monitored by MRI. Blood profiles of patients can also be monitored including assays of immunogen-specific antibodies and T-cells responses.

Following baseline measures, patients begin receiving treatment. They are randomized and treated with either therapeutic agent or placebo in a blinded fashion. Patients are monitored at least every six months. Efficacy is determined by a significant reduction in progression of a treatment group relative to a placebo group.

A second phase II trial is performed to evaluate conversion of patients from non-Alzheimer's Disease early memory loss, sometimes referred to as age-associated memory impairment (AAMI) or mild cognitive impairment (MCI), to probable Alzheimer's disease as defined as by ADRDA criteria Patients with high risk for conversion to Alzheimer's Disease are selected from a non-clinical population by screening reference populations for early signs of memory loss or other difficulties associated with pre-Alzheimer's symptomatology, a family history of Alzheimer's Disease, genetic risk factors, age, sex, and other features found to predict high-risk for Alzheimer's Disease. Baseline scores on suitable metrics including the MMSE and the ADAS together with other metrics designed to evaluate a more normal population are collected. These patient populations are divided into suitable groups with placebo comparison against dosing alternatives with the agent. These patient populations are followed at intervals of about six months, and the endpoint for each patient is whether or not he or she converts to probable Alzheimer's Disease as defined by ADRDA criteria at the end of the observation.

XIII. General Materials and Methods

1. Measurement of Antibody Titers

Mice were bled by making a small nick in the tail vein and collecting about 200 µl of blood into a microfuge tube. Guinea pigs were bled by first shaving the back hock area and then using an 18 gauge needle to nick the metatarsal vein and collecting the blood into microfuge tubes. Blood was allowed to clot for one hr at room temperature (RT), vortexed, then centrifuged at 14,000×g for 10 min to separate the clot from the serum. Serum was then transferred to a clean microfuge tube and stored at 4° C. until titered.

Antibody titers were measured by ELISA. 96-well microtiter plates (Costar EIA plates) were coated with 100 µl of a solution containing either 10 µg/ml either Aβ42 or SAPP or other antigens as noted in each of the individual reports in Well Coating Buffer (0.1 M sodium phosphate, pH 8.5, 0.1% sodium azide) and held overnight at RT. The wells were aspirated and sera were added to the wells starting at a 1/100 dilution in Specimen Diluent (0.014 M sodium phosphate, pH 7.4, 0.15 M NaCl, 0.6% bovine serum albumin, 0.05% thimerosal). Seven serial dilutions of the samples were made directly in the plates in three-fold steps to reach a final dilution of 1/218,700. The dilutions were incubated in the coated-plate wells for one hr at RT. The plates were then washed four times with PBS containing 0.05% Tween 20. The second antibody, a goat anti-mouse Ig conjugated to horseradish peroxidase (obtained from Boehringer Mannheim), was added to the wells as 100 µl of a 1/3000 dilution in Specimen Diluent and incubated for one hr at RT. Plates were again washed four times in PBS, Tween 20. To develop the chromogen, 100 µl of Slow TMB (3,3',5,5'-tetramethyl benzidine obtained from Pierce Chemicals) was added to each well and incubated for 15 min at RT. The reaction was stopped by the addition of 25 µl of 2 M $H_2SO_4$. The color intensity was then read on a Molecular Devices Vmax at (450 nm–650 nm).

Titers were defined as the reciprocal of the dilution of serum giving one half the maximum OD. Maximal OD was generally taken from an initial 1/100 dilution, except in cases with very high titers, in which case a higher initial dilution was necessary to establish the maximal OD. If the 50% point fell between two dilutions, a linear extrapolation was made to calculate the final titer. To calculate geometric mean antibody titers, titers less than 100 were arbitrarily assigned a titer value of 25.

2. Lymphocyte Proliferation Assay

Mice were anesthetized with isoflurane. Spleens were removed and rinsed twice with 5 ml PBS containing 10% heat-inactivated fetal bovine serum (PBS-FBS) and then homogenized in a 50° Centricon unit (Dako A/S, Denmark) in 1.5 ml PBS-FBS for 10 sec at 100 rpm in a Medimachine (Dako) followed by filtration through a 100 micron pore size nylon mesh. Splenocytes were washed once with 15 ml PBS-FBS, then pelleted by centrifugation at 200×g for 5 min. Red blood cells were lysed by resuspending the pellet in 5 mL buffer containing 0.15 M NH4Cl, 1 M KHCO3, 0.1 M NaEDTA, pH 7.4 for five min at RT. Leukocytes were then washed as above. Freshly isolated spleen cells ($10^5$ cells per well) were cultured in triplicate sets in 96well U-bottomed tissue culture-treated microtiter plates (Corning, Cambridge, Mass.) in RPMI 1640 medium (JRH Biosciences, Lenexa, Kans.) supplemented with 2.05 mM L glutamine, 1% Penicillin/Streptomycin, and 10% heat-inactivated FBS, for 96 hr at 37° C. Various A peptides, Aβ1–16, Aβ1–40, Aβ1–42 or Aβ40–1 reverse sequence protein were also added at doses ranging from 5 to 0.18 micromolar in four steps. Cells in control wells were cultured with Concanavalin A (Con A) (Sigma, cat. #C-5275, at 1 microgram/ml) without added protein. Cells were pulsed for the final 24 hr with 3H-thymidine (1 µCi/well obtained from Amersham Corp., Arlington Heights Ill.). Cells were then harvested onto UniFilter plates and counted in a Top Count Microplate Scintillation Counter (Packard Instruments, Downers Grove, Ill.). Results are expressed as counts per minute (cpm) of radioactivity incorporated into insoluble macromolecules.

4. Brain Tissue Preparation

After euthanasia, the brains were removed and one hemisphere was prepared for immunohistochemical analysis, while three brain regions (hippocampus, cortex and cerebellum) were dissected from the other hemisphere and used to measure the concentration of various Aβ proteins and APP forms using specific ELISAs (Johnson-Wood et al., supra).

Tissues destined for ELISAs were homogenized in 10 volumes of ice-cold guanidine buffer (5.0 M guanidine-HCl, 50 mM Tris-HCl, pH 8.0). The homogenates were mixed by gentle agitation using an Adams Nutator (Fisher) for three to four hr at RT, then stored at −20° C. prior to quantitation of Aβ and APP. Previous experiments had shown that the analytes were stable under this storage condition, and that synthetic Aβ protein (Bachem) could be quantitatively recovered when spiked into homogenates of control brain tissue from mouse littermates (Johnson-Wood et al., supra).

5. Measurement of Aβ Levels

The brain homogenates were diluted 1:10 with ice cold Casein Diluent (0.25% casein, PBS, 0.05% sodium azide, 20 µg/ml aprotinin, 5 mM EDTA pH 8.0, 10 µg/ml leupeptin) and then centrifuged at 16,000×g for 20 min at 4° C. The synthetic Aβ protein standards (1–42 amino acids) and the APP standards were prepared to include 0.5 M guanidine and 0.1% bovine serum albumin (BSA) in the final composition The "total" Aβ sandwich ELISA utilizes monoclonal antibody monoclonal antibody 266, specific for amino acids 13–28 of Aβ (Seubert, et al.), as the capture antibody, and biotinylated monoclonal antibody 3D6, specific for amino acids 1–5 of Aβ (Johnson-Wood, et al), as the reporter antibody. The 3D6 monoclonal antibody does not recognize secreted APP or full-length APP, but detects only Aβ species with an amino-terminal aspartic acid. This assay has a lower limit of sensitivity of ~50 ng/ml (11 nM) and shows no cross-reactivity to the endogenous murne Aβ protein at concentrations up to 1 ng/ml (Johnson-Wood et al., supra).

The Aβ1–42 specific sandwich ELISA employs mAβ 21F12, specific for amino acids 33–42 of Aβ (Johnson-Wood, et al.), as the capture antibody. Biotinylated mAβ 3D6 is also the reporter antibody in this assay which has a lower limit of sensitivity of about 125 µg/ml (28 µM, Johnson-Wood et al.). For the Aβ ELISAs, 100 µl of either mAβ 266 (at 10 µg/ml) or mAβ 21F12 at (5 µg/ml) was coated into the wells of 96-well immunoassay plates (Costar) by overnight incubation at RT. The solution was removed by aspiration and the wells were blocked by the addition of 200 µl of 0.25% human serum albumin in PBS buffer for at least 1 hr at RT. Blocking solution was removed and the plates were stored desiccated at 4° C. until used. The plates were rehydrated with Wash Buffer [Tris-buffered saline (0.15 M NaCl, 0.01 M Tris-HCl, pH 7.5), plus 0.05% Tween 20] prior to use. The samples and standards were added in triplicate aliquots of 100 µl per well and then incubated overnight at 4° C. The plates were washed at least three times with Wash Buffer between each step of the assay. The biotinylated mAβ 3D6, diluted to 0.5 µg/ml in Casein Assay Buffer (0.25% casein, PBS, 0.05% Tween 20, pH 7.4), was added and incubated in the wells for 1 hr at RT. An avidin-horseradish peroxidase conjugate, (Avidin-HRP obtained from Vector, Burlingame, Calif.), diluted 1:4000 in Casein Assay Buffer, was added to the wells for 1 hr at RT. The colorimetric substrate, Slow TMB-ELISA (Pierce), was added and allowed to react for 15 minutes at RT, after which the enzymatic reaction was stopped by the addition of 25 µl 2 N H2SO4. The reaction product was quantified using a Molecular Devices Vmax measuring the difference in absorbance at 450 nm and 650 nm.

6. Measurement of APP Levels

Two different APP assays were utilized. The first, designated APP-α/FL, recognizes both APP-alpha (α) and full-length (FL) forms of APP. The second assay is specific for APP-α. The APP-α/FL assay recognizes secreted APP including the first 12 amino acids of Aβ. Since the reporter antibody (2H3) is not specific to the α-clip-site, occurring between amino acids 612–613 of APP695 (Esch et al., Science 248, 1122–1124 (1990)); this assay also recognizes full length APP (APP-FL). Preliminary experiments using immobilized APP antibodies to the cytoplasmic tail of APP-FL to deplete brain homogenates of APP-FL suggest that approximately 30–40% of the APP-α/FL APP is FL (data not shown). The capture antibody for both the APP-α/FL and APP-α assays is mAb 8E5, raised against amino acids 444 to 592 of the APP695 form (Games et al., supra). The reporter mAb for the APP-α/FL assay is mAb 2H3, specific for amino acids 597–608 of APP695 (Johnson-Wood et al., supra) and the reporter antibody for the APP-α assay is a biotinylated derivative of mAb 16H9, raised to amino acids 605 to 611 of APP. The lower limit of sensitivity of the APP-αFL assay is about 11 ng/ml (150 pM) (Johnson-Wood et al.) and that of the APP-α specific assay is 22 ng/ml (0.3 nM). For both APP assays, mAb 8E5 was coated onto the wells of 96-well EIA plates as described above for mAb 266. Purified, recombinant secreted APP-α was used as the reference standard for the APP-α assay and the APP-α/FL assay (Esch et al., supra). The brain homogenate samples in 5 M guanidine were diluted 1:10 in ELISA Specimen Diluent (0.014 M phosphate buffer, pH 7.4, 0.6% bovine serum albumin, 0.05% thimerosal, 0.5 M NaCl, 0.1% NP40). They were then diluted 1:4 in Specimen Diluent containing 0.5 M guanidine. Diluted homogenates were then centrifuged at 16,000×g for 15 seconds at RT. The APP standards and samples were added to the plate in duplicate aliquots and incubated for 1.5 hr at RT. The biotinylated reporter antibody 2H3 or 16H9 was incubated with samples for 1 hr at RT. Streptavidin-alkaline phosphatase (Boehringer Mannheim), diluted 1:1000 in specimen diluent, was incubated in the wells for 1 hr at RT. The fluorescent substrate 4-methyl-umbellipheryl-phosphate was added for a 30-min RT incubation and the plates were read on a Cytofluor tm 2350 fluorimeter (Millipore) at 365 nm excitation and 450 nm emission.

7. Immunohistochemistry

Brains were fixed for three days at 40 C in 4% paraformaldehyde in PBS and then stored from one to seven days at 4° C. in 1% paraformaldehyde, PBS until sectioned. Forty-micron-thick coronal sections were cut on a vibratome at RT and stored in cryoprotectant (30% glycerol, 30% ethylene glycol in phosphate buffer) at −20° C. prior to immunohistochemical processing. For each brain, six sections at the level of the dorsal hippocampus, each separated by consecutive 240 μm intervals, were incubated overnight with one of the following antibodies: (1) a biotinylated anti-Aβ (mAb, 3D6, specific for human Aβ diluted to a concentration of 2 μg/ml in PBS and 1% horse serum; or (2) a biotinylated mAb specific for human APP, 8E5, diluted to a concentration of 3 μg/ml in PBS and 1.0% horse serum; or (3) a mAb specific for glial fibrillary acidic protein (GFAP; Sigma Chemical Co.) diluted 1:500 with 0.25% Triton X-100 and 1% horse serum, in Tris-buffered saline, pH 7.4 (TBS); or (4) a mAb specific for CD11b, MAC-1 antigen, (Chemicon International) diluted 1:100 with 0.25% Triton X-100 and 1% rabbit serum in TBS; or (5) a mAb specific for MHC II antigen, (Pharmingen) diluted 1:100 with 0.25% Triton X-100 and 1% rabbit serum in TBS; or (6) a rat mAb specific for CD 43 (Pharmingen) diluted 1:100 with 1% rabbit serum in PBS or (7) a rat mAb specific for CD 45RA (Pharmingen) diluted 1:100 with 1% rabbit serum in PBS; or (8) a rat monoclonal Aβ specific for CD 45RB (Pharmingen) diluted 1:100 with 1% rabbit serum in PBS; or (9) a rat monoclonal Aβ specific for CD 45 (Pharmingen) diluted 1:100 with 1% rabbit serum in PBS; or (10) a biotinylated polyclonal hamster Aβ specific for CD3e Pharmingen) diluted 1:100 with 1% rabbit serum in PBS or (11) a rat mAb specific for CD3 (Serotec) diluted 1:200 with 1% rabbit serum in PBS; or with (12) a solution of PBS lacking a primary antibody containing 1% normal horse serum.

Sections reacted with antibody solutions listed in 1,2 and 612 above were pretreated with 1.0% Triton X-100, 0.4% hydrogen peroxide in PBS for 20 min at RT to block endogenous peroxidase. They were next incubated overnight at 4° C. with primary antibody. Sections reacted with 3D6 or 8E5 or CD3e mAbs were then reacted for one hr at RT with a horseradish peroxidase-avidin-biotin-complex with kit components "A" and "B" diluted 1:75 in PBS (Vector Elite Standard Kit, Vector Labs, Burlingame, Calif.). Sections reacted with antibodies specific for CD 45RA, CD 45RB, CD 45, CD3 and the PBS solution devoid of primary antibody were incubated for 1 hour at RT with biotinylated anti-rat IgG (Vector) diluted 1:75 in PBS or biotinylated anti-mouse IgG (Vector) diluted 1:75 in PBS, respectively Sections were then reacted for one hr at RT with a horseradish peroxidase-avidin-biotin-complex with kit components "A" and "B" diluted 1:75 in PBS (Vector Elite Standard Kit, Vector Labs, Burlingame, Calif.).

Sections were developed in 0.01% hydrogen peroxide, 0.05% 3,3'-diaminobenzidine (DAB) at RT. Sections destined for incubation with the GFAP-, MAC-1- AND MHC II-specific antibodies were pretreated with 0.6% hydrogen peroxide at RT to block endogenous peroxidase then incubated overnight with the primary antibody at 4° C. Sections reacted with the GFAP antibody were incubated for 1 hr at RT with biotinylated anti-mouse IgG made in horse (Vector Laboratories; Vectastain Elite ABC Kit) diluted 1:200 with TBS. The sections were next reacted for one hr with an avidin-biotin-peroxidase complex (Vector Laboratories; Vectastain Elite ABC Kit) diluted 1:1000 with TBS. Sections incubated with the MAC-1- or MHC II-specific monoclonal antibody as the primary antibody were subsequently reacted for 1 hr at RT with biotinylated anti-rat IgG made in rabbit diluted 1:200 with TBS, followed by incubation for one hr with avidin-biotin-peroxidase complex diluted 1:1000 with TBS. Sections incubated with GFAP-, MAC-1- and MHC II-specific antibodies were then visualized by treatment at RT with 0.05% DAB, 0.01% hydrogen peroxide, 0.04% nickel chloride, TBS for 4 and 11 min, respectively.

Immunolabeled sections were mounted on glass slides (VWR, Superfrost slides), air dried overnight, dipped in Propar (Anatech) and overlaid with coverslips using Permount (Fisher) as the mounting medium.

To counterstain Aβ plaques, a subset of the GFAP-positive sections were mounted on Superfrost slides and incubated in aqueous 1% Thioflavin S (Sigma) for 7 min following immunohistochemical processing. Sections were then dehydrated and cleared in Propar, then overlaid with coverslips mounted with Permount.

8. Image Analysis

A Videometric 150 Image Analysis System (Oncor, Inc., Gaithersburg, Md.) linked to a Nikon Microphot-FX microscope through a CCD video camera and a Sony Trinitron monitor was used for quantification of the immunoreactive slides. The image of the section was stored in a video buffer and a color-and saturation-based threshold was determined to select and calculate the total pixel area occupied by the immunolabeled structures. For each section, the hippocampus was manually outlined and the total pixel area occupied by the hippocampus was calculated. The percent amyloid burden was measured as: (the fraction of the hippocampal area containing Aβ deposits immunoreactive with mAb 3D6)×100. Similarly, the percent neuritic burden was measured as: (the fraction of the hippocampal area containing dystrophic neurites reactive with monoclonal antibody 8E5)×100. The C-Imaging System (Compix, Inc., Cranberry Township, Pa.) operating the Simple 32 Software Application program was linked to a Nikon Microphot-FX microscope through an Optronics camera and used to quantitate the percentage of the retrospenial cortex occupied by GFAP-positive astrocytes and MAC-1- and MHC II-positive microglia. The image of the immunoreacted section was stored in a video buffer and a monochrome-based threshold was determined to select and calculate the total pixel area occupied by immunolabeled cells. For each section, the retrosplenial cortex (RSC) was manually outlined and the total pixel area occupied by the RSC was calculated. The percent astrocytosis was defined as: (the fraction of RSC occupied by GFAP-reactive astrocytes)×100. Similarly, percent microgliosis was defined as: (the fraction of the RSC occupied by MAC-1- or MHC II-reactive microglia)×100. For all image analyses, six sections at the level of the dorsal hippocampus, each separated by consecutive 240 μm intervals, were quantitated for each animal. In all cases, the treatment status of the animals was unknown to the observer.

XIV: Ex Vivo Screening Assay for Activity of an Antibody Against Amyloid Deposits An ex vivo assay in which primary microglial cells were cultured with unfixed cryostat sections of either PDAPP mouse or human Aβ brains was established, in order to examine the effects of antibodies on plaque clearance. Microglial cells were obtained from the cerebral cortices of neonate DBA/2N mice (1–3 days). The cortices were mechanically dissociated in HBSS⁻ (Hanks' Balanced Salt Solution, Sigma) with 50 μg/ml DNase I (Sigma). The dissociated cells were filtered with a 100 μm cell strainer (Falcon), and centrifuged at 1000 rpm for 5 minutes. The pellet was resuspended in growth medium (high glucose DMEM, 10% FBS, 25 ng/ml rmGM-CSF), and the cells were plated at a density of 2 brains per T-75 plastic culture flask. After 7–9 days, the flasks were rotated on an orbital shaker at 200 rpm for 2h at 37° C. The cell suspension was centrifuged at 100 rpm and resuspended in the assay medium.

10-μm cryostat sections of PDAPP mouse or human Aβ brains (post-mortem interval <3 hr) were thaw mounted onto poly-lysine coated round glass coverslips and placed in wells of 24-well tissue culture plates. The coverslips were washed twice with assay medium consisting of H-SFM (Hybridoma-serum free medium, Gibco BRL) with 1% FBS, glutamine, penicillin/streptomycin, and 5ng/ml rmGM-CSF (R&D). Control or anti-Aβ antibodies were added at a 2x concentration (5 μg/ml final) for 1 hour. The microglial cells were then seeded at a density of $0.8 \times 10^6$ cells/ml assay medium. The cultures were maintained in a humidified incubator (37° C., 5% $CO_2$) for 24 hr or more. At the end of the incubation, the cultures were fixed with 4% paraformaldehyde and permeabilized with 0.1% Triton-X100. The sections were stained with biotinylated 3D6 followed by a streptavidin/Cy3 conjugate (Jackson ImmunoResearch). The exogenous microglial cells were visualized by a nuclear stain (DAPI). The cultures were observed with an inverted fluorescent microscope (Nikon, TE300) and photomicrographs were taken with a SPOT digital camera using SPOT software (Diagnostic instruments). For Western blot analysis, the cultures were extracted in 8M urea, diluted 1:1 in reducing tricine sample buffer and loaded onto a 16% tricine gel (Novex). After transfer onto immobilon, blots were exposed to 5 μg/ml of the pabAβ42 followed by an HRP-conjugated anti-mouse antibody, and developed with ECL (Amersham)

When the assay was performed with PDAPP brain sections in the presence of antibody 16C11 (one of the antibodies against Aβ that was not efficacious in vivo), β-amyloid plaques remained intact and no phagocytosis was observed. In contrast, when adjacent sections were cultured in the presence of 10D5, the amyloid deposits were largely gone and the microglial cells showed numerous phagocytic vesicles containing Aβ. Identical results were obtained with Aβ brain sections; 10D5 induced phagocytosis of AD plaques, while 16C11 was ineffective. In addition, the assay provided comparable results when performed with either mouse or human microglial cells, and with mouse, rabbit, or primate antibodies against Aβ.

Table 16 shows results obtained with several antibodies against Aβ, comparing their abilities to induce phagocytosis in the ex vivo assay and to reduce in vivo plaque burden in passive transfer studies. Although 16C11 and 21F12 bound to aggregated synthetic Aβ peptide with high avidity, these antibodies were unable to react with β-amyloid plaques in unfixed brain sections, could not trigger phagocytosis in the ex vivo assay, and were not efficacious in vivo. 10D5, 3D6, and the polyclinal antibody against Aβ were active by all three measures. The 22C8 antibody binds more strongly to an analog form of natural Aβ in which aspartic acid at positions 1 and 7 is replaced with iso-aspartic acid. These results show that efficacy in vivo is due to direct antibody mediated clearance of the plaques within the CNS, and that the ex vivo assay is predictive of in vivo efficacy.

The same assay has been used to test clearing of an antibody against a fragment of synuclein referred to as NAC. Synuclein has been shown to be an amyloid plaque-associated protein. An antibody to NAC was contacted with a brain tissue sample containing amyloid plaques, an microglial cells, as before. Rabbit serum was used as a control. Subsequent monitoring showed a marked reduction in the number and size of plaques indicative of clearing activity of the antibody.

TABLE 16

The ex vivo assay as predictor of in vivo efficacy.

| Antibody | Isotype | Avidity for aggregated Aβ (pM) | Binding to β-amyloid plaques | Ex vivo efficacy | In vivo efficacy |
|---|---|---|---|---|---|
| monoclonal | | | | | |
| 3D6 | IgG2b | 470 | + | + | + |
| 10D5 | IgG1 | 43 | + | + | + |
| 16C11 | IgG1 | 90 | − | − | − |
| 21F12 | IgG2a | 500 | − | − | − |
| TM2a | IgG1 | − | − | − | − |
| polyclonal | | | | | |
| 1–42 | mix | 600 | + | + | + |

Confocal microscopy was used to confirm that Aβ was internalized during the course of the ex vivo assay. In the presence of control antibodies, the exogenous microglial cells remained in a confocal plane above the tissue, there were no phagocytic vesicles containing Aβ, and the plaques remained intact within the section. In the presence of 10D5, nearly all plaque material was contained in vesicles within the exogenous microglial cells. To determine the fate of the internalized peptide, 10D5 treated cultures were extracted with 8M urea at various time-points, and examined by Western blot analysis. At the one hour time point, when no phagocytosis had yet occurred, reaction with a polyclonal antibody against Aβ revealed a strong 4 kD band (corresponding to the Aβ peptide). Aβ immunoreactivity decreased at day I and was absent by day 3. Thus, antibody-mediated phagocytosis of Aβ leads to its degradation.

To determine if phagocytosis in the ex vivo assay was Fc-mediated, F(ab')2 fragments of the anti-Aβ antibody 3D6 were prepared. Although the F(ab')2 fragments retained their full ability to react with plaques, they were unable to trigger phagocytosis by microglial cells. In addition, phagocytosis with the whole antibody could be blocked by a reagent against murine Fc receptors (anti-CD16/32). These data indicate that in vivo clearance of Aβ occurs through Fc-receptor mediated phagocytosis.

XV: Passage of Antibodies through the Blood-brain Barrier

This experiments described herein were performed in order to provide information on ability of antibodies to pass into the brain following intravenous injection and to provide means for measuring the concentration of antibody delivered to the brain following intravenous injection into a peripheral tissue of either normal or PDAPP mice. Such measurements are useful in predicting and determining effective dosages.

PDAPP or control normal mice were perfused with 0.9% NaCl. Brain regions (hippocampus or cortex) were dissected and rapidly frozen. Brain were homogenized in 0.1% triton+ protease inhibitors. Immunoglobulin was detected in the extracts by ELISA. Fab'2 Goat Anti-mouse IgG were coated onto an RIA plate as capture reagent. The serum or the brain extracts were incubated for 1 hr. The isotypes were detected with anti-mouse IgG1-HRP or IgG2a-HRP or IgG2b-HRP (Caltag). Antibodies, regardless of isotype, were present in the CNS at a concentration that is 1:1000 that found in the blood. For example, when the concentration of IgG1 was three times that of IgG2a in the blood, it was three times IgG2a in the brain as well, both being present at 0.1% of their respective levels in the blood. This result was observed in both transgenic and nontransgenic mice so the PDAPP does not have a uniquely leaky blood brain barrier.

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

---

It is claimed:

1. A method of prophylaxis of Alzheimer's disease in a mammalian subject, comprising: administering to the subject a dosage of synuclein-NAC effective to produce an immune response comprising anti-synuclein antibodies and an adjuvant that augments that immune response to the synuclein, wherein said administering further comprises administering an immunogenic Aβ fragment, thereby effecting prophylaxis of Alzheimer's disease.

2. The method of claim 1, wherein said adjuvant is selected from the group consisting of STIMULON QS21, 3 De-O-acylated-monophosphoryl lipid A, and alum.

3. The method of claim 1, wherein said immune response is characterized by a serum titer of the anti-synuclein antibodies of at least 1:1000 with respect to synuclein.

4. The method of claim 3, wherein said serum titer of the anti-synuclein antibodies is at least 1:5000 with respect to synuclein.

5. The method of claim 1, wherein said immune response is characterized by a serum titer of the anti-synuclein antibodies corresponding to greater than about four times higher than a serum titer of anti-synuclein antibodies measured in a pre-treatment control serum sample.

6. The method of claim 5, wherein said serum titer of the antibodies is measured at a serum dilution of about 1:100.

7. A method of treating Alzheimer's disease in a mammalian subject, comprising administering to the subject a dosage of synuclein-NAC effective to produce an immune response comprising anti-synuclein antibodies and an adjuvant that augments the immune response to the synuclein, wherein said administering further comprises administering an immunogenic Aβ fragment, and thereby treating the disease.

8. The method of claim 7, wherein said synuclein-NAC is linked to a carrier molecule to form a conjugate.

9. The method of claim 7, wherein said adjuvant is selected from the group consisting of STIMULON QS-21, 3 De-O-acylated-monophosphoryl lipid, and alum.

10. The method of claim 7, wherein said immune response is characterized by a serum titer of the anti-synuclein antibodies of at least 1:1000 with respect to synuclein.

11. The method of claim 10, wherein said serum titer of the anti-synuclein antibodies is at least 1:5000 with respect to synuclein.

12. The method of claim 7, wherein said immune response is characterized by a serum titer of anti-synuclein antibodies corresponding to greater than about four times higher than a serum titer of anti-synuclein antibodies of measured in a pre-treatment control serum sample.

13. The method of claim 12, wherein said serum titer of the anti-synuclein antibodies is measured at a serum dilution of about 1:100.

14. The method of claim 1, wherein said Aβ fragment is Aβ1–3.

15. The method of claim 1, wherein said Aβ fragment is Aβ1–4.

16. The method of claim 1, wherein said Aβ fragment is Aβ1–5.

17. The method of claim 1, wherein said Aβ fragment is Aβ1–6.

18. The method of claim 1, wherein said Aβ fragment is Aβ3–7.

19. The method of claim 1, wherein said Aβ fragment is Aβ1–10.

20. The method of claim 1, wherein said Aβ fragment is Aβ1–12.

21. The method of claim 1, wherein said Aβ fragment is Aβ13–28.

22. The method of claim 1, wherein said Aβ fragment is Aβ25–35.

23. The method of claim 1, wherein said Aβ fragment is Aβ33–42.

24. The method of claim 1, wherein said Aβ fragment is linked to a carrier molecule to form a conjugate.

25. The method of claim 14, wherein said Aβ fragment is linked to a carrier molecule to form a conjugate.

26. The method of claim 15, wherein said Aβ fragment is linked to a carrier molecule to form a conjugate.

27. The method of claim 16, wherein said Aβ fragment is linked to a carrier molecule to form a conjugate.

28. The method of claim 17, wherein said Aβ fragment is linked to a carrier molecule to form a conjugate.

29. The method of claim 18, wherein said Aβ fragment is linked to a carrier molecule to form a conjugate.

30. The method of claim 19, wherein said Aβ fragment is linked to a carrier molecule to form a conjugate.

31. The method of claim 20, wherein said Aβ fragment is linked to a carrier molecule to form a conjugate.

32. The method of claim 21, wherein said Aβ fragment is linked to a carrier molecule to form a conjugate.

33. The method of claim 22, wherein said Aβ fragment is linked to a carrier molecule to form a conjugate.

34. The method of claim 23, wherein said Aβ fragment is linked to a carrier molecule to form a conjugate.

35. The method of claim 7, wherein said Aβ fragment is Aβ1–3.

36. The method of claim 7, wherein said Aβ fragment is Aβ1–4.

37. The method of claim 7, wherein said Aβ fragment is Aβ1–5.

38. The method of claim 7, wherein said Aβ fragment is Aβ1–6.

39. The method of claim 7, wherein said Aβ fragment is Aβ3–7.

40. The method of claim 7, wherein said Aβ fragment is Aβ1–10.

41. The method of claim 7, wherein said Aβ fragment is Aβ1–12.

42. The method of claim 7, wherein said Aβ fragment is Aβ13–28.

43. The method of claim 7, wherein said Aβ fragment is Aβ25–35.

44. The method of claim 7, wherein said Aβ fragment is Aβ33–42.

45. The method of claim 7, wherein said Aβ fragment is linked to a carrier to form a conjugate.

46. The method of claim 35, wherein said Aβ fragment is linked to a carrier to form a conjugate.

47. The method of claim 36, wherein said Aβ fragment is linked to a carrier to form a conjugate.

48. The method of claim 37, wherein said Aβ fragment is linked to a carrier to form a conjugate.

49. The method of claim 38, wherein said Aβ fragment is linked to a carrier to form a conjugate.

50. The method of claim 39, wherein said Aβ fragment is linked to a carrier to form a conjugate.

51. The method of claim 40, wherein said Aβ fragment is linked to a carrier to form a conjugate.

52. The method of claim 41, wherein said Aβ fragment is linked to a carrier to form a conjugate.

53. The method of claim 42, wherein said Aβ fragment is linked to a carrier to form a conjugate.

54. The method of claim 43, wherein said Aβ fragment is linked to a carrier to form a conjugate.

55. The method of claim 44, wherein said Aβ fragment is linked to a carrier to form a conjugate.

56. The method of claim 1, wherein the subject has a known genetic risk of Alzheimer's disease.

57. The method of claim 7, wherein the subject has a known genetic risk of Alzheimer's disease.

\* \* \* \* \*